US005851983A

United States Patent [19]
Sugiyama et al.

[11] Patent Number: 5,851,983
[45] Date of Patent: Dec. 22, 1998

[54] ELASTASE INHIBITORY POLYPEPTIDE AND PROCESS FOR PRODUCTION THEREOF BY RECOMBINANT GENE TECHNOLOGY

[75] Inventors: Takashi Sugiyama; Takashi Kamimura, both of Hino; Kenichi Masuda, Hachioji; Masahiro Okada, Hino; Eiko Ohtsuka, Sapporo; Atsushi Imaizumi, Hino; Kunihito Watanabe, Hino; Tetsuya Suga, Hino; Yohichi Matsumoto, Musashino; Akiko Takeuchi, Hino, all of Japan

[73] Assignee: Teijin Limited, Osaka, Japan

[21] Appl. No.: 963,538

[22] Filed: Oct. 20, 1992

Related U.S. Application Data

[63] Continuation-in-part of Ser. No. 843,359, Feb. 25, 1992, abandoned, which is a continuation-in-part of Ser. No. 408,483, Aug. 22, 1989, abandoned, which is a continuation-in-part of PCT/JP88/0142 Dec. 28, 1988..

[30] Foreign Application Priority Data

| Dec. 28, 1987 | [JP] | Japan | 62-330219 |
| Dec. 24, 1991 | [JP] | Japan | 3-355553 |
| Jul. 17, 1992 | [JP] | Japan | 4-212398 |
| Jul. 17, 1992 | [JP] | Japan | 4-212399 |

[51] Int. Cl.$^6$ .......... A61K 38/16; C12N 15/41; C07K 14/81
[52] U.S. Cl. .............. 514/2; 530/324; 435/69.2
[58] Field of Search .................. 530/324, 350; 435/69.2; 514/12

[56] References Cited

U.S. PATENT DOCUMENTS

| 4,511,502 | 4/1985 | Builder et al. | 260/112 |
| 4,760,130 | 7/1988 | Thompson et al. | 530/350 |
| 4,845,076 | 7/1989 | Heinzel et al. | 514/12 |

FOREIGN PATENT DOCUMENTS

| 0346500 A1 | 12/1989 | European Pat. Off. . |
| WO 86/03519 | of 0000 | WIPO . |
| WO 89/06239 | 7/1989 | WIPO . |

OTHER PUBLICATIONS

Janoff, A., "Elastases and Emphysema", Am. Rev. Respir. Dis (1985) 132:417–433.
Fujisawa, et al., "The Neutrophil and Chronic Allergic Inflammation", Am. Rev. Respir. Dis. (1990) 141:689–697.
Stokley, et al., "Alpha$_1$–Antitrypsin and Leukocytke Elastase in Infected and Noninfected Sputum$_{1-3}$", Am. Rev. Respir. Dis (1979) 120:1081–1086.
McDonald, et al., "Degradation of Fibronectin by Human Leukocyte Elastase", J. Biol. Chem. (1980) 255:8848–8858.
Mainardi, et al., "Specific Cleavage of Human Type III Collagen by Human Polymorphonuclear Leukocyte Elastase*", J. Biol. Chem. (1980) 255:12006–12010.
Thompson, et al., "Isolation, Properties, and Complete Amino Acid Sequence of Human Secretory Leukocyte Protease Inhibitor, a Potent Inhibitor of Leukocyte Elastase", PNAS 83:6692–6696 (1986).
Stetler, et al., "Isolation and Sequence of a Human Gene Encoding a Potent Inhibitor of Leukocyte Proteases", Nucleic Acids Res. 14:7883–7896 (1986).
Stetler, et al., "Secretion of Active, Full–and Half–Length Human Secretory Leukocyte Protease Inhibitor by *Saccharomyces cerevisiae*", Biotechnology 7:55–60 (1989).
Mecklein, et al., "The Location of Inhibitory Specificities in Human Mucus Proteinase Inhibitor (MPI): Separate Expression of the COOH–Terminal Domain Yields an Active Inhibitor of Three Different Proteinases", Protein Engineering, 3:215–220 (1990).
Fujita, et al., "Evaluation of Elastase and Antielastase Balance in Patients with Chronic Bronchitis and Pulmonary Emphysema$_{1-3}$", Am. Rev. Respir. Dis. 142:57–62 (1990).
Lee, et al., "Elastolytic Activity in Pulmonary Lavage Fluid from Patients with Adult Respiratory–Distress Syndrome", N. Engl. J. Med. 304:192–196 (1981).
Barrett, A. in Methods in Enzymology vol. 80, pp. 581–588 (1981).
Abrams, et al., "Proteinase Inhibitory Function in Inflammatory Lung Disease", Am. Rev. Respir. Dis. 129:735–741 (1984).
Snider, G., "Pulmonary Disease in Alpha–1–Antitrypsin Deficiency", Annals of Int. Med., 111:957–959 (1989).
Imaizumi, et al., "Specific Cleavage of Secretory Leukoprotease Inhibitor in Saliva", Am. Rev. Respir. Dis. 145:A201 (1992).
Ohlsson et al., Structure, Genomic Organization, and Tissue Distribution of Human Secretory Leucocyte–Protease Inhibitor (SLPI): A Potent Inhibitor of Neutrophil Elastase, Pulm.Emphysema Proteolysis (Conf.), Meeting date 1986, Edited by: Taylor J.C. et al., Academic Orlando, FLA, pp.: 307–322 (1987).
Masuda, et al., "Expression of the C–Terminal Domain of Secretory Leukoprotease Inhibitor in *E. Coli* as a Thrombin–Cleavable Fusion Protein", Am. Rev. Respir. Dis., 145:A200 (1992).

*Primary Examiner*—Sally Teng
*Attorney, Agent, or Firm*—Cooley Godward LLP

[57] ABSTRACT

The present invention provides an elastase inhibitory polypeptide comprising a C-terminal half of a human secretory leukocyte protease inhibitor (SLPI) and having an elastase inhibitory activity wherein inhibitory activity of a trypsin-like serine protease does not exceed $\frac{1}{10}$ of elastase inhibitory activity, and polypeptides having the above-mentioned biological activity wherein one or more than one amino acid is added, one or more than one amino acid is deleted and/or one or more than one amino acid is replaced. The present invention also provides a process for the production of the above-mentioned protein or other protein via a corresponding fused protein.

15 Claims, 21 Drawing Sheets

Fig. 1

SGKSFKAGVCPPKKSAQCLRYKKPECQSDWQCPGKKRCCPDTCGIKCLDPVDTP

NPTRRKPGKCPVTYGQCLMLNPPNFCEMDGQCKRDLKCCMGMCGKSCVSPVKA

Fig. 2

```
              BamHI  SalI                    MluI
              GATCCGGTCGACACCCCGAACCCGACGCGTCGT
                    GCCAGCTGTGGGGCTTGGGCTGCGCAGCA
                                    AsnProThrArgArg

NdeI
AAACCGGGTAAATGTCCGGTTACATATGGTCAGTGTCTGATGCTGAACCCGCCGAACTTC
TTTGGCCCATTTACAGGCCAATGTATACCAGTCACAGACTACGACTTGGGCGGCTTGAAG
LysProGlyLysCysProValThrTyrGlyGlnCysLeuMetLeuAsnProProAsnPhe

BglII
TGTGAAATGGACGGTCAGTGTAAACGAGATCTGAAATGTTGTATGGGTATGTGTGGTAAA
ACACTTTACCTGCCAGTCACATTTGCTCTAGACTTTACAACATACCCATACACACCATTT
CysGluMetAspGlyGlnCysLysArgAspLeuLysCysCysMetGlyMetCysGlyLys

XhoI  PstI
TCTTGTGTTTCTCCGGTTAAAGCATAATAGCTCGAGCTGCA
AGAACACAAAGAGGCCAATTTCGTATTATCGAGCTCG
SerCysValSerProValLysAlastopstop
```

Fig. 3

```
           5'
      ①  GATCCGGTCGACACCCCGAACCCGACGCGTCGT
           ②  GCCAGCTGTGGGGCTTGGGCTGCGCAGCA
              3'
```

```
                                    ③
AAACCGGGTAAATGTCCGGTTACATATGGTCAGTGTCTGATGCTGAACCCGCCGAACTTC
TTTGGCCCATTTACAGGCCAATGTATACCAGTCACAGACTACGACTTGGGCGGCTTGAAG
                                            ④
```

```
                                    ⑤
TGTGAAATGGACGGTCAGTGTAAACGAGATCTGAAATGTTGTATGGGTATGTGTGGTAAA
ACACTTTACCTGCCAGTCACATTTGCTCTAGACTTTACAACATACCCATACACACCATTT
                                                    ⑥
```

```
                                          3'
TCTTGTGTTTCTCCGGTTAAAGCATAATAGCTCGAGCTGCA
AGAACACAAAGAGGCCAATTTCGTATTATCGAGCTCG
                                     5'
```

Fig. 4

```
                          THROMBIN CLEVAGE SITE
                                  │
         Gln Ile Phe Leu Val Pro Arg Asn Pro Thr
         5'
         ⑦ G-ATC-TTC-CTG-GTT-CCG-CGT-AAC-CCG-A
              ⑧ AAG-GAC-CAA-GGC-GCA-TTG-GGC-TGC-GC
                 3'
```

BglII                            MluI

```
                         HYDROXYLAMINE CLEAVAGE SITE
                                  │
         Gln Ile Phe Asn Gly Asn Pro Thr Arg
         5'
         ⑨ G-ATC-TTC-AAC-GGT-AAC-CCG-A
              ⑩ -AAG-TTG-CCA-TTG-GGC-TGC-GC
                 3'
```

BglII                       MluI

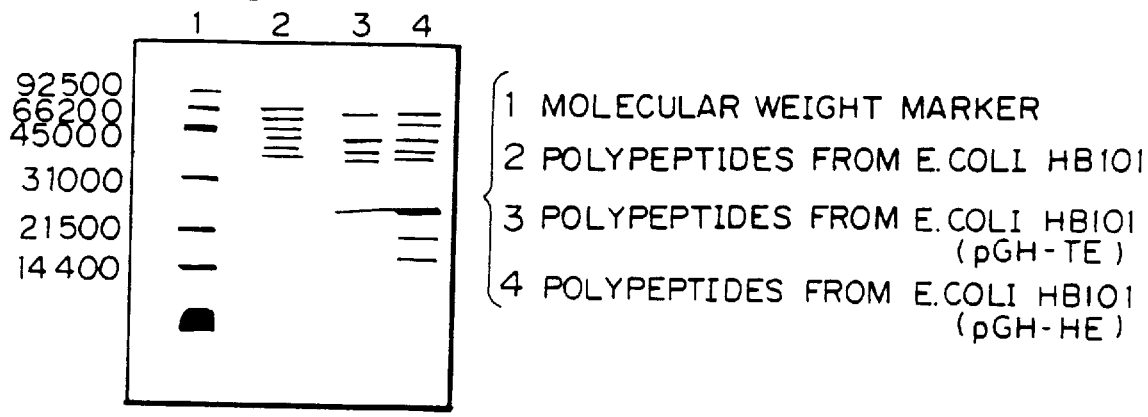

Fig. 6

1 MOLECULAR WEIGHT MARKER
2 POLYPEPTIDES FROM E. COLI HB101
3 POLYPEPTIDES FROM E. COLI HB101 (pGH-TE)
4 POLYPEPTIDES FROM E. COLI HB101 (pGH-HE)

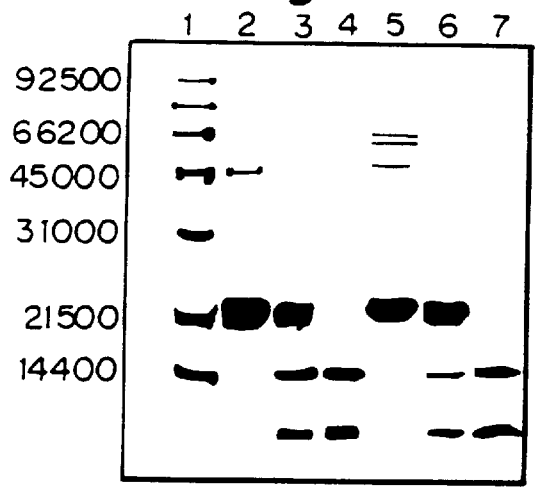

Fig. 7

1 MOLECULAR WEIGHT MARKER
2 POLYPEPTIDES FROM E.COLI HB101 (pGH-TE)
3 POLYPEPTIDES FROM E.COLI HB101 (pGH-TE) (THROMBIN 2 HOURS)
4 POLYPEPTIDES FROM E.COLI HB101 (pGH-TE) (THROMBIN 15 HOURS)
5 POLYPEPTIDES FROM E. COLI HB101 (pGH-HE)
6 POLYPEPTIDES FROM E. COLI HB101 (pGH-HE) (HYDROXYLAMINE 1 HOURS)
7 POLYPEPTIDES FROM E. COLI HB101 (pGH-HE) (HYDROXYLAMINE 4 HOURS)

LANE 1 (Mw): MOLECULAR WEIGHT MAKER

LANE 1 (Mw) : MOLECULAR WEIGHT MAKER

| LANE No. | ELASTASE CONCENTRATION | SLPI CONCENTRATION |
|---|---|---|
| 2 | 0 µM | 50 µM |
| 3 | 3.13 | 50 µM |
| 4 | 6.25 | 50 µM |
| 5 | 12.5 | 50 µM |
| 6 | 25 | 50 µM |
| 7 | 50 | 50 µM |
| 8 | 100 | 50 µM |
| 9 | 200 | 50 µM |

ELASTASE INHIBITORY POLYPEPTIDE AND PROCESS FOR PRODUCTION THEREOF BY RECOMBINANT GENE TECHNOLOGY

CROSS REFERENCE TO RELATED APPLICATION

This application is a continuation-in-part application of Ser. No. 07/843,359 filed on Feb. 25, 1992, now abandoned, which is a continuation-in-part of Ser. No. 07/408,483, filed Aug. 22, 1989, now abandoned, which is a National Stage Filing of PCT/JP88/01342 filed Dec. 28, 1988 and published as WO89/06239 on Jul. 13, 1989.

BACKGROUND OF THE INVENTION

1. Field of the Invention

The present invention relates to an elastase inhibitory polypeptide and a fused protein suitable for the production thereof, as well as a process for the production of the elastase inhibitory polypeptide from this fused protein. Moreover, the present invention relates to a fused protein gene used for the production microorganism carrying the same. The present invention further relates to a pharmaceutical preparation comprising said polypeptide.

2. Background Art

Advances in recombinant DNA techniques have made it possible to produce clinically or economically valuable proteins (hereinafter designated as desired protein) in microbial cells. When such proteins are produced by using microbial cells as host cells, first a gene coding for a desired protein is isolated from various cells or chemically synthesized, and then the gene is expressed in host cells, resulting in the production of the desired protein. Nevertheless, obstacles to or problems in the expression of the gene and production of the desired protein exist, and therefore, to produce the desired protein or a portion thereof in microbial cells efficiently and in a commercially liable scale, first the above-mentioned problems must be solved.

For example, where it is intended to produce a protein having a relatively low molecular weight, such as a peptide or protein having not more than 100 amino acid residues, the produced peptide or protein is recognized as a foreign substance in microbial cells, and tends to be hydrolyzed by various kinds of proteolytic enzymes, and this often makes it impossible to efficiently produce the desired protein. Therefore, to solve such problems, various approaches have been attempted.

As one of these approaches, it is known that a fused protein gene is constituted by linking a gene for a desired protein and a gene for a protein other than the desired protein (designated as carrier protein) followed by an expression of the fused protein gene in microbial cells to produce the desired protein.

As an embodiment thereof, a process is known wherein a gene for coding a desired protein is joined with an endogenous gene coding for a microbial cellular protein or a portion thereof, and the constructed gene is expressed in microbial cells. In this process, a fused protein comprising a desired protein fused with the entire microbial cellular protein or a portion thereof, which is not intracellularly hydrolyzed, is able to be obtained. Such microbial protein used as carrier proteins for the above-mentioned purpose include β-galactosidase (S. Tanaka et al., Nucl. Acids. Res.10, 1741–1754, 1982), β-lactamase (P. Cornelis et al., Mol. Gen. Genet. 186, 507–511, 1982), chloramphenicol acetyl transferase (A. Hobden et al., WPI 87-88509/13), alkaline phosphatase (Japanese Unexamined Patent Publication No. 58-225098). Moreover, as an example of a carrier protein which not only protects a desired protein from a proteolytic degradation but also makes a purification of the desired protein easier, Staphylococcus protein A is known (Japanese Unexamined Patent Publication No. 62-190087, T. Moks et al., Biochemistry 26, 5239–5244, 1987).

As a second embodiment thereof, a process is known wherein a gene encoding a desired protein is linked with a gene of an exogenous protein or a portion thereof, which is a foreign protein itself but is not recognized a stranger is the cells, is expressed. In this process, and exogenous protein or a portion thereof fused desired protein is obtained stable at high levels. Examples of such exogenous proteins are β-interferon (I. Ivanov et al., FEBS Lett. 210 56–60, 1987), $\alpha_1$-antitrypsin (Van der Straten A et al Bioscience Reports 6 3630373, 1986) and so on.

Fused proteins thus obtained comprising a desired protein and carrier protein sometimes completely lose the biological activity of the desired protein or the biological activity of the desired protein is reduced. Alternatively, even if fused proteins have a biological activity of the desired protein they are anxious to exhibit biological activities of the carrier protein such as antigenity, and therefore, the fused proteins as such cannot be clinically used. Accordingly, the desired protein must be cleaved from the fused protein. To this end, an amino acid sequence of a junction (hereinafter designated as a linking peptide) between a carrier protein and a desired protein is successfully designed so that the junction is site-specifically cleaved, and after the production of the fused protein in cells, the desired protein is cleaved from the fused protein.

Generally, a fused protein produced in microbial cells is designed so that a carrier protein constitutes an N-terminal portion of a fused protein. Such a structure can provide a desired protein free from both the carrier protein and N-terminal amino acid residue, therefore, is clinically advantageous.

Such site-specific cleavage methods include chemical cleavage methods using chemical reagents and biological cleavage methods using enzymes. The chemical cleavage methods include the cyanogen bromide method, hydroxylamine method, formic acid method, NBS (N-bromosuccinimide method), lithium/methylamine/NBS method, bromine/hydrochloric acid method, and the like.

The cyanogen bromide method is most often used, and Itakura et al. succeeded in generating a desired protein, somatostatin, from *Escherichia coli* β-galactosidase fused somatostatin using cyanogen bromide (K. Itakura et al., Science 198, 1056, 1977; Japanese Unexamined Patent Publication No. 54-163600). Cyanogen bromide hydrolyzes a peptide bond at methionine residue under an acidic condition. Therefore, to site-specifically cleave a fused protein, the desired protein must have a methionine residue at its N-terminus and contain no methionine residue in an amino acid sequence of the desired protein, and therefore, the application of the cyanogen bromide is necessarily limited.

Enzymatic methods include the endopeptidase method. Endopeptidase recognizes one or more than one specific amino acid in an internal amino acid sequence, and preferentially cleaved a peptide bond at a carboxyl site of a specific amino acid. Herein an amino acid or amino acid sequence which is specifically recognized by endopeptidase is designated as a "recognized amino acid" or "recognized amino acid sequence". The various endopeptidases used to cleave a fused protein produced by microbial cells to generate a desired protein include the following: trypsin used to generate human calcitonin from tryptophan synthetase (WO 84/00380); trypsin used to generate β-endorphin from a β-galactosidase fused β-endorophin; bovine enteropeptidase used to generate enkephalin from β-galactosidase fused enkephalin (V. N. Dobrynin et al., Bioory-Khim 13, 119–121, 1987); enterokinase used to generate human atrial natriuretic factor (h-ANF) from chloramphenicol acetyltransferase fused h-ANP using Val-Asp-Asp-Asp-Asp-Lys (SEQ ID NO:6) as recognized amino acid sequence (A. Hobden et al., WPI 87-088 509/13); factor Xa used to generate β-globin from λC11 fused β-globin, or human calcitonin-glycine from chloramphenicol acetyltransferase fused calcitonin-glycine using (Ile/Leu/Pro/Ala)-(Glu/Asp/Gln/Asn)-Gly-Arg as a recognized amino acid sequence (Japanese Unexamined Patent Publication No. 61-135591); and V8 protease using Glu-X as a recognized amino acid sequence, factor Xa using Glu-Gly-Arg as a recognized sequence, thrombin using Arg-Ala-Leu-Leu-Ala-Gly-Pro-Arg (SEQ ID NO:7) or Gly-Pro-Arg, all used to generate atrial natriuretic peptide (ANP) from rec A protein fused ANP (Japanese Unexamined Patent Publication No. 62-135500).

A method wherein a desired protein is produced as a fused protein with a carrier protein in microbial cells has provided a powerful means of production of the desired protein, but a method wherein a microbial cellular protein is used as a carrier protein does not provide a satisfactory economical production because this method provides a lower expression level of a fused protein. Alternatively, where an exogenous protein is used as a carrier protein, the resultant fused protein is usually present as a soluble component in microbial cytoplasm or in periplasmic space, and therefore, a complicated separation and purification process must be used to isolate the fused protein.

In addition to the above-mentioned problems, other problems arise in the fused protein approach. Namely, a desired protein itself as such produced as a fused protein is useless. Generation of a desired protein from a fused protein is necessary, and to this end, a choice of a linking peptide forming a fusion site is important. Fusion via methionine which is cleaved by cyanogen bromide is disadvantageous in that it has a limited application, and a universal linking peptide which can be cleaved by an enzyme is requested. Where an amino acid sequence which can be cleaved by an enzyme (recognized amino acid sequence) is used, according to circumstances (primary amino acid sequence, secondary and tertiary structure et al.) under which a carrier protein and a desired protein are present, it may be difficult to generate a desired protein, and therefore, the extent of cleavage and proper liberation has been difficult to expect. A choice of a fused protein having a recognized amino acid sequence which site-specifically liberates a desired protein effects not only the chemical treatment or enzymic treatment for the cleavage, but also the expression, production and accumulation of the fused protein. Currently, no fused protein systems including a carrier protein and linking peptide which satisfy all of the above-mentioned requirements are known.

As diseases wherein neutrophils increase in the sputum, the bronchus or a alveolar lavage fluid, chronic bronchitis, diffuse panbronchiolitis, alveolar ectasia, bronchietasis, bacterial pneumonia, synusitis, respiratory distress syndrome (RDS), and the like are known (Am. Rev. Respir Dis. 132, 417–433, 1985). Elastase is secreted from neutrophils which have run into the lung or bronchus (Am. Rev. Respir. Dis. 141, A357, 1990), therefore a high concentration of elastase was formed in fluid of respiratory tract or purulent sputum of inflammatory respiratory organ diseases (Ann. Int. Med. 111, 957–959, 1989; Am. Rev. Respir. Dis. 120, 1081–1088, 1979).

Although neutrophil protease is responsible for the defense mechanism of an organism against foreign materials such as bacteria, viruses and the like, an excess amount of neutrophil protease attacks that organism itself resulting in degradation of the matrix of the lung (J. Biol. Chem. 255, 8848–8858, 1980, J. Biol. Chem. 255, 12006–12010, 1980).

Although an organism produces a group of protease inhibitors, if a balance between neutrophil protease and protease inhibitors results in an excess of neutrophil protease, then the lung matrix is injured, and if such a condition continues for a long time, the diseases becomes severe (Am. Rev. Respir. Dis. 132, 417–433, 1985).

Human secretory leukoprotease inhibitor (hereinafter designated as SLPI) is a protease inhibitor that is produced by serous cells of submucosal glands of trachea and bronchi and defends the organism from an excess amount of neutrophil elastase mainly in the upper respiratory tract, but a mechanism of degradation of SLPI by an excess amount of neutrophil elastase at an inflammatory site is not known.

SLPI is also derived from human polymorphonuclear leukocytes and present in human mucos fluid such as parotid secretions, bronchial secretions, seminal plasma, cervical mucus, etc. An amino acid sequence of this protein isolated from a secretes from a parotid gland was determined (R. C. Thompson et al., Proc. Nat. Acad. Sci. USA 83, 6692–6696, 1988; PCT Japanese National Publication No. 62-501291); and a gene for this protein was isolated from a human parotid gland gene library and sequenced (R. C. Thompson et al. Nucl. Acid Res. 14, 7883–7896, 1986; PCT Japanese National Publication No. 62-501262).

The SLPI inhibits a human polymorphonuclear leukocyte elastase, and therefore, is expected to be used as a therapeutic agent to arrest the emphysema, which is believed to be caused by a hydrolysis of elastin by elastase. Nevertheless, in addition to an inhibitory activity to chymotrypsin-like proteases such as human polymorphonuclear leukocyte elastase, human neutrophil elastase, human cathepsin G, human pancreatic elastase, and human chymotrypsin, the SLPI exhibits an inhibitory activity to trypsin-like protease, and accordingly, it is feared that SLPI would inhibit a physiologically important trypsin-like serine protease such as pancreatic trypsin, plasmin, kallikrein, thrombin, and the like, and therefore, if the SLPI, per se, is administered, it would affect a blood coagulation-fibrinolysis system, etc., and it is difficult to use the same as a therapeutic agent for human.

For this reason, a SLPI carboxy terminal polypeptide, wherein an N-terminal half of SLPI has been deleted, was prepared by a gene technology, and was confirmed to maintain an elastase inhibitory activity of SLPI but substantially not to have trypsin inhibitory activity (G. L. Stetler et al., Biotechnology, 7, 55–60, 1989; Barbara et al., Protein Engineering 3, 215–220, 1990; WO 89/06239).

Although such a SLPI carboxy terminal polypeptide lacks a trypsin-like enzyme inhibitor activity, which is supposed to induce side effects, however, where it is used as a pharmaceutical another problem is expected. Since the reported SLPI carboxy terminal polypeptides are artificial and non-natural polypeptides, if they are used in humans there is a possibility that they will be antigenic and will induce antibodies.

If an antibody is generated to a polypeptide medicament, an effect of the medicament is neutralized with the antibody resulting in the disappearance of a pharmacological effect, and there is also a possibility that a severe antigen-antibody reaction will occur in the body, and it becomes impossible to continue administration of the peptide medicament to the body in which the antibody is produced. It is well known that the human body can easily produce antibodies against non-native polypeptides.

So far, a partial decomposition of a carboxymethylated linear SLPI with an enzyme was reported (Proc. Natl. Acad. Sci. USA, 83, 6692–6696, 1986). This SLPI is a non-natural SLPI not having an inhibitory activity, and therefore, the resulting fragment is non-natural, and its elastase inhibitory activity, cathepsin G inhibitory activity, trypsin inhibitory activity, and antigenity are not described. Therefore, a naturally occurring polypeptide having an inhibitory activity to elastase is desired for therapeutic purposes.

DISCLOSURE OF THE INVENTION

Accordingly, the present invention provides a novel elastase inhibitory polypeptide wherein elastase inhibitory activity (an inhibitory activity of chymotrypsin-like serine protease) of SLPI is maintained while an inhibitory activity of trypsin-like serine protease of SLPI is notably reduced, and a process for the production thereof, as a preconditional means therefor, an ideal carrier protein which simultaneously satisfies the requirement that a fused protein can be expressed at high level in microbial production of a desired protein by genetic engineering and the requirement that a downstream process including isolation and purification of the fused protein is easier, and a linking peptide which allows a reliable cleavage at the junction site and a release of the desired protein in an intact form.

Accordingly, the present invention generally provides an elastase inhibitory polypeptide comprising C-terminal half of a human secretory leukocyte protease inhibitor (SLPI) and having an elastase inhibitory activity wherein an inhibitory activity of trypsin-like serine protease is lower than an elastase inhibitory activity, and polypeptide having the above-mentioned biological activity wherein one or more than one acid is added, one or more than one amino acid is deleted and/or one or more than one amino acid is replaced.

The present invention also provides a fused protein useful as an intermediate for the production of the above-identified polypeptide represented by the formula (II$_2$):

$$Y—B—Z_2 \qquad (II_2)$$

wherein Y represents a carrier protein comprising a human growth hormone or a fragment thereof; $Z_2$ represents an elastase inhibitory polypeptide comprising C-terminal half of human secretory leukocyte protease inhibitor (SLPI) and having an elastase inhibitory activity, and inhibitory activity of trypsin-like serine protease is lower than an elastase inhibitory activity, or polypeptide having the above-mentioned biological activity wherein one or more than one amino acid is added, one or more than one amino acid is deleted and/or one or more than one amino acid is replaced; and B represents a linking peptide or homopolymer thereof having an amino acid sequence which can be chemically or biologically cleaved under the condition wherein the desired protein is not denatured; wherein B is linked to an N-terminal amino acid in $Z_2$.

The present invention moreover provides a process for the production of an elastase inhibitory polypeptide or homopolymers thereof represented inhibitory polypeptide or homopolymers thereof represented by the formula (I):X—(SEQ ID NO:1, SEQ ID NO:2, or SEQ ID NO:3 wherein X represent Gly, comprising the step of treating a fused protein represented by the formula (IV):

$$Y-(Asn-Gly)_{\overline{n}}Z \qquad (IV)$$

wherein Y and Z have meanings defined under the formula (II), n represents an integer of 1 to 10, and Gly in the formula (IV) is linked to an N-terminus Asn in Z, with hydroxylamine or an analog thereof.

The present invention also provides a process for polypeptide or homopolymers thereof represented by the formula (I) wherein X is absent, comprising the step of treating a fused protein represented by the formula (V):

$$Y—B'—Z \qquad (V)$$

wherein Y and Z have meanings defined under the formula (II), B' represents -(Val-Pro-Arg)$_{\overline{n}}$ or -(Leu-Val-Pro-Arg)$_{\overline{n}}$  (SEQ ID NO:8) wherein n represents an integer of 1 to 10, and Asn in X is linked to Arg in B' with thrombin or an analog thereof.

The present invention also provides a fused protein gene comprising a gene coding for human growth hormone or a fragment thereof as a carrier protein linked to a gene coding for a desired protein or a portion thereof via a gene coding for a peptide or polypeptide having an amino acid sequence which can be chemically or biologically cleaved under the condition wherein the desired protein is not denaturated. As an example of the desired protein, an elastase inhibitory polypeptide having an amino acid sequence represented by the formula (III) or a portion thereof exhibiting an elastase inhibitory activity or an amino acid sequence biologically equivalent thereto is mentioned.

The present invention also provides a plasmid carrying the above-mentioned gene, and microbial cells carrying the plasmid.

BRIEF DESCRIPTION OF THE DRAWINGS

FIG. 1 represents a primary amino acid sequence of SLPI (SEQ ID NO:4), expressed by a one letter abbreviation;

FIG. 2 represents a sequence of a synthetic structural gene (SEQ ID NO:5) for (Asn$^{55}$-Ala$^{107}$) SLPI polypeptide using codons preferably used in E. coli, wherein (Asn$^{55}$-Ala$^{107}$) SLPI means a polypeptide comprising an amino acid sequence from the 55th Asn to the 107th Ala of SLPI;

FIG. 3 represents chemically synthesized oligonucleotide fragments (1) to (6) (corresponding to SEQ ID NO:31, SEQ ID NO:32, SEQ ID NO:33, SEQ ID NO:34, SEQ ID NO:35 and SEQ ID NO:36);

FIG. 4 represents synthetic oligonucleotide fragments (7) to (10) (SEQ ID NO:12, SEQ ID NO:28, SEQ ID NO:13 and SEQ ID NO:29) coding for a linking peptide which links a gene coding for a (Met$^{-1}$Phe$^{1}$-Phe$^{139}$) human growth hormone fragment (a polypeptide comprising an amino acid sequence from the first Phe to the 139th Phe of a human growth hormone having an additional Met at N-terminus and a gene coding for (Asn$^{55}$-Ala$^{107}$) SLPI;

FIG. 6 represents an SDS-PAGE profile of an expressed fused protein (Example 4);

FIG. 7 represents a SDS-PAGE profile obtained by thrombin treatment of the fused protein (Example 5) or by hydroxylamine treatment (Example 6);

BEST MODE OF CARRYING OUT THE INVENTION

Figure 5:
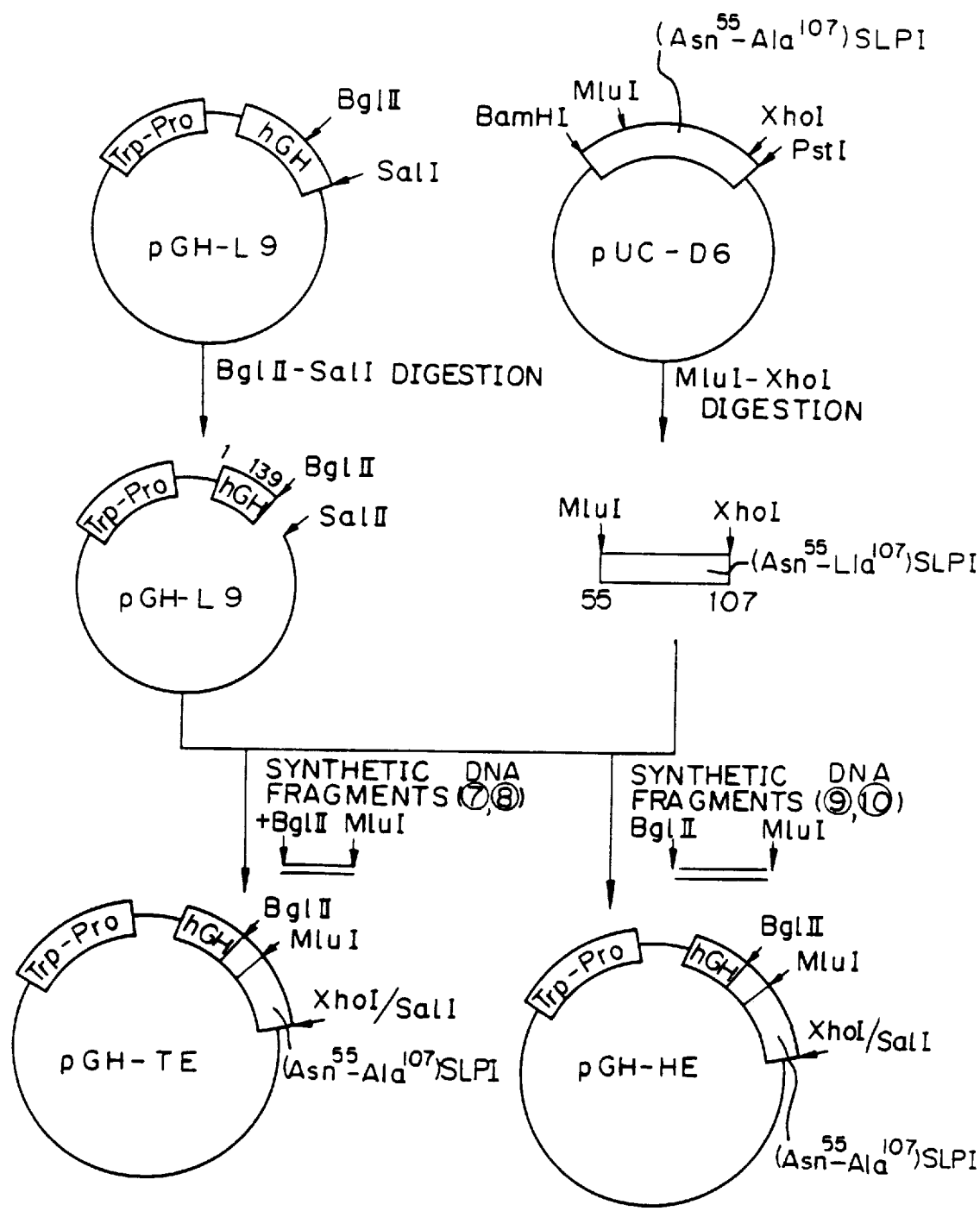
FIG. 5 represents a scheme for a construction of a plasmid for an expression of a fused protein gene (Examples 2 and 3)

The present inventors originally confirmed that a polypeptide comprising approximately a C-terminal half portion of SLPI starting from the first Ser and terminating at the 107th Ala has substantially no inhibitory activity of trypsin-like serine protease while maintaining an inhibitory activity of an elastase. An extent in SLPI forming the present polypeptide is not critical. As a preferable example of the present and terminating at the 107th Ala of SLPI is mentioned. Two to ten repeats of this polypeptide may form a homopolymer.

These polypeptide are represented by the formula (I) X-(SEQ ID NO:1-)$_n$ wherein SEQ ID NO:1 represents the polypeptide having the sequence:

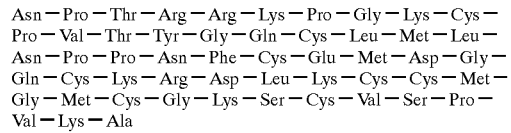

wherein X represents Gly or is absent, and n represents an integer of 1 to 10, or a part thereof exhibiting an elastase inhibitory activity or an amino acid sequence biologically equivalent thereto.

According to the methods used for cleavage of a fused protein in the production of the present polypeptide, an amino-terminus of the polypeptide is either Asn wherein X is absent or Gly attached to Asn wherein X represents Gly.

Note, the present invention includes, in addition to the polypeptide having the above-mentioned amino acid sequence, polypeptide having an amino acid sequence wherein one or more than one amino acid is deleted, one or more than one amino acid is added and/or one or more than one amino acid is replaced by the other amino acid(s) to the extent that they exhibit the abovementioned biological activity.

A preferred embodiment of the polypeptides having an amino acid sequence wherein one or more than one amino acid is deleted is a polypeptide starting from the 59th Arg and ending at 107th Ala of SLPI. Two to ten repetitions of this polypeptide may form a homopolymer. This polypeptide, and the homopolymer thereof, are represented by the following formula (I") X-(SEQ ID NO:3-)$_n$:

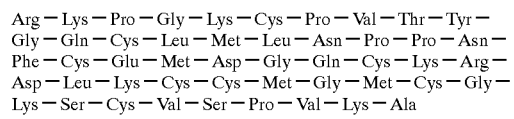

wherein X represents Gly or is absent, and n represents an integer of 1 to 10.

Another preferred embodiment of the polypeptide having an amino acid sequence wherein one or more than one amino acid is deleted is a polypeptide starting from the 58th Arg and ending at 107th Ala of SLPI. Two to ten repetitions of this polymer may form a homopolymer. This polypeptide and the homopolymer thereof are represented by the following formula (I') X–(SEQ ID NO:2)$_n$:

Arg — Arg — Lys — Pro — Gly — Lys — Cys — Pro — Val — Thr — Tyr — Gly — Gln — Cys — Leu — Met — Leu — Asn — Pro — Pro — Asn — Phe — Cys — Glu — Met — Asp — Gly — Gln — Cys — Lys — Arg — Asp — Leu — Lys — Cys — Cys — Met — Gly — Met — Cys — Gly — Lys — Ser — Cys — Val — Ser — Pro — Val — Lys — Ala wherein X represents Gly or is absent, and n represents an integer of 1 to 10.

Note, in the present invention, elastase inhibitory polypeptides of the present invention are shown by using the numbering system of the amino acid sequence of native SLPI. Namely, a polypeptide having an amino acid sequence starting with the 55th Asn and ending at the 107th Ala of SLPI is shown by (Asn$^{55}$-Ala$^{107}$) SLPI, which corresponds to the amino acid sequence in SEQ ID NO: 1. Similarly, a polypeptide having an amino acid sequence starting with the 58th Arg and ending at the 107th Ala is shown by (Arg$^{58}$-Ala$^{107}$) SLPI, which correspond to the amino acid sequence in SEQ ID NO: 2, and a polypeptide having an amino acid sequence starting with the 59th Arg and ending at the 107th Ala is shown by (Arg$^{59}$-Ala$^{107}$) SLPH, which corresponds to the amino acid sequence in SEQ ID NO: 3.

In an preferred embodiment of the present invention, the present polypeptides have 4 disulfide linkages at the positions corresponding to those in native SLPI, namely, Cys$^{64}$-Cys$^{93}$, Cys$^{72}$-Cys$^{80}$, CYS$^{71}$-Cys$^{97}$ and Cys$^{86}$-Cys$^{101}$ in native SLPI; which correspond Cys$^{10}$-Cys$^{39}$, Cys$^{38}$-Cys$^{26}$, Cys$^{17}$-Cys$^{43}$ and Cys$^{29}$-Cys$^{47}$ in SEQ ID NO: 1; Cys$^{7}$-Cys$^{36}$, Cys$^{35}$-Cys$^{23}$, Cys$^{14}$-Cys$^{40}$ and Cys$^{29}$-Cys$^{44}$ in SEQ ID NO: 2; and Cys$^{6}$-Cys$^{35}$, Cys$^{34}$-Cys$^{22}$, Cys$^{13}$-Cys$^{39}$ and Cys$^{28}$-Cys$^{43}$ in SEQ ID NO: 3.

The above-mentioned shortened polypeptide shown by (Arg$^{58}$-Ala$^{107}$) SLPI is produced by a cleavage of native SLPI with polymorphonuclear leucocyte elastase from human sputum, or by a cleavage of (Asn$^{55}$-Ala$^{107}$) SLPI with the same elastase, and therefore native to humans. The polypeptide (Arg$^{58}$-Ala$^{107}$) SLPI exhibits a high elastase inhibitory activity and cathepsin G inhibitory activity, but does not substantially exhibit a trypsin inhibitory activity. The above-mentioned properties of the (Arg$^{58}$-Ala$^{107}$) SLPI make it promising for therapeutic use.

The above-mentioned shortened polypeptide shown by (Arg$^{59}$-Ala$^{107}$) SLPI is produced by a cleavage of native SLPI produced by gene engineering with an enzyme present in healthy human saliva, and therefore, is native to humans. The polypeptide (Arg$^{59}$-Ala$^{107}$) SLPI exhibits a high elastase inhibitory activity and cathepsin G inhibitory activity, but does not substantially exhibit a trypsin inhibitory activity. The above-mentioned properties of the (Arg$^{59}$-Ala$^{107}$) SLPI make it promising for therapeutic use.

These proteins cannot be directly produced by gene expression in microbial cells by a recombinant gene technology. Namely, since the desired protein is a low molecular weight protein, it can be produced only by the present process wherein the desired protein is genetically produced in a form of a fused protein containing, for example, a human growth hormone as a carrier protein, and the fused protein is cleaved with an enzyme such as thrombin or chemicals such as hydroxylamine to generate the desired protein.

Accordingly, the present invention provides a fused protein represented by the above-mentioned formula (II') useful as an intermediate for the production of the above-mentioned elastase inhibitory polypeptide. Within the fused protein represented by the formula (II'), a fused protein wherein the desired protein comprises the (Asn$^{55}$-Ala$^{107}$) SLPI, (Arg$^{58}$-Ala$^{107}$) SLPI or (Arg$^{59}$-Ala$^{107}$) SLPI, is represented by the following formula (IIa):

Y—B—Za        (IIa)

wherein Y represents a carrier protein, for example, comprising a human growth hormone or fragment thereof;

Z represents a polypeptide which is an elastase inhibitory polypeptide or homopolymers thereof having a sequence represented by the formula (IIIa):

–(N—Lys—Pro—Gly—Lys—Cys—Pro—Val—Thr—Tyr—Gly—Gln—Cys—Leu—Met—Leu—Asn—Pro—Pro—Asn—Phe—Cys—Glu—Met—Asp—Gly—Gln—Cys—Lys—Arg—Asp—Leu—Lys—Cys—Cys—Met—Gly—Met—Cys—Gly—Lys—Ser—Cys—Val—Ser—Pro—Val—Lys—Ala)$_n$ wherein N is Arg (SEQ ID NO:3), Arg-Arg (SEQ ID NO:2), or Asn-Pro-Thr-Arg-Arg (SEQ ID NO:1); n represents an integer of 1 to 10, or a portion thereof exhibiting an inhibitory activity of elastase or an amino acid sequence biologically equivalent thereto; and B represents a linking peptide or homopolymer thereof having an amino acid sequence which can be chemically or biologically cleaved under the condition wherein the desired protein is not denaturated; wherein B is joined to an amino terminus in Z.

Note, an amino acid sequence represented by the general formula (IIIa) wherein N represents Asn-Pro-Thr-Arg-Arg is designated as formula (III), and a fused protein represented by the general formula (IIa) wherein Za represents the formula (III) is designated as formula (II); an amino acid sequence represented by the general formula (IIIa) wherein N represents Arg-Arg is designated as formula (III'), and a fused protein represented by the general formula (IIa) wherein Za represents the formula (III) is designated as formula (II'); and an amino acid sequence represented by the general formula (IIIa) wherein N represents Arg is designated as formula (III"), and a fused protein represented by the general formula (II) wherein Za represents the formula (III") is designated as formula (II").

The carrier protein in the formula (II), (II') and (II") is preferably a human growth hormone or a portion thereof which provides a higher expression level of fused protein and is present as inclusion bodies in microbial cells, and is easy to isolate and purify. The human growth hormone is a polypeptide consisting of 191 amino acid residues starting with the first Phe and terminating at the 191th Phe. Where a desired gene is expressed using a carrier protein in *E. coli*, since Met residue is essential for the initiation codon of translation, an expressed protein must be a methionyl human growth hormone. Therefore, such a protein also fall within the scope of the present carrier protein. Moreover, modified human growth hormones wherein the amino acid sequence of a native human growth hormone is partially changed, fall within the scope of the present carrier protein. An example of such a modified human growth hormone is that wherein the 53th cysteine is replaced by another amino acid. A preferable portion of a human growth hormone used as a carrier protein is a fragment from the first Phe to the 139th Phe, or a fragment from the first Phe to the 122th Gln. Another preferred carrier protein is T7 phage gene 10 protein (pGEM-EX™ Vector, Promega; Studier F. et al., J. Mol. Biol. 189, 113, 1986) or a part thereof.

A linking peptide or homopolymer thereof at a junction site includes any recognized amino acid sequence including known sequences, which can be chemically or biologically cleaved under the condition wherein the desired protein is not denaturated.

For example Asn-Gly (P. Bornstein, Meth. Enzymol. 47, 132, 1977) or a repeating sequence thereof (Asn-Gly)$_n$ wherein n represents an integer of 1 to 10 can be used as a linking peptide which can be cleaved by hydroxylamine to generate the desired protein. Moreover, as a fusion amino acid sequence which can be cleaved by thrombin, although a reported amino acid sequence Ala-Asp-Ser-Gly-Glu-Gly-Asp-Phe-Leu-Ala-Glu-Gly-Gly-Gly-Val-Arg-Glu-Gly-Val-Asn-Asp-Asn-Glu-Glu-Gly-Phe-Phe-Ser-Ala-Arg, or Asp-Asp-Pro-Pro-Thr-Val-Glu-Leu-Gln-Cly-Leu-Val-Pro-Arg (B. Blomback et al., BBA 115, 371–396, 1966; T. Takagi et al., Biochemistry 13, 750–756, 1974) (SEQ ID NO:9 and SEQ ID NO:10) can be used, a shorter amino acid sequence Val-Pro-Arg or Leu-Val-Pro-Arg (SEQ ID NO:8), or repeating sequences thereof (Val-Pro-Arg)$_n$ or (Leu-Val-Pro-Arg)$_n$ wherein n represents an integer of 1 to 10 is preferably used to reliably release and separate a desired protein without affect on a primary amino acid sequence and steric effect of the carrier protein an desired protein. Another preferred linker peptide is an amino acid sequence cleaved by enterokinase, for example (SEQ ID NO:11) (Asp-Asp-Asp-Asp-Lys)$_n$ wherein n is an integer of 1 to 10. In these cases, a C-terminus Gly, Arg or Lys in B is joined to the N-terminus in Z respectively.

To produce the present polypeptide represented by the formula (I), a fused protein represented by the formula (II) is cleaved at its junction site of B. Where this cleavage should be carried out by hydroxylamine or an analog thereof, (Asn-Gly)$_n$ is used as B. Namely, a fused protein represented by the above-mentioned formula (IV) is treated with hydroxylamine or an analog thereof such as alkyl hydroxylamine, hydrazine or the like to obtain an elastase inhibitory polypeptide or homopolymer thereof wherein X in the formula (I) is Gly. Alternatively, where cleavage at a linking peptide B should be carried out by thrombin or an analog thereof, for example, (Val-Pro-Arg)$_n$ or (Leu-Val-Pro-Arg)$_n$ is used as B. Namely, a fused protein represented by the above-mentioned formula (V) is treated with a thrombin or analog thereof such as human thrombin, bovine thrombin, equine thrombin, porcine thrombin, or the like to obtain an elastase inhibitory polypeptide or homopolymer thereof represented by the formula (I) wherein X is absent.

Moreover, enterokinase or an analog thereof can be used. As the enterokinase or analog thereof, bovine enterokinase used for liberation of enkephalin from β-galactosidase (V. N. Dobrynin et al., Bioorg-Khim 13, 119–121, 1987), enterokinase used for liberation of human atrial natriuretic factor from chloramphenicol acetyltransferase (A. Hobden et al., WP187-088509/13), and the like can be used. In these cases, as X, for example, (Asp-Asp-Asp-Asp-Lys)$_n$ wherein n represents an integer of 1 to 10 is preferably used.

A fused protein represented by the formula (II) is produced according to a recombinant gene technology known per se. In this case, the present invention is characterized by using a fused protein gene comprising a gene coding for a human growth hormone or a fragment thereof as a carrier protein linked to a gene coding for a desired protein or a portion thereof via a gene coding for a peptide or polypeptide having an amino acid sequence which can be chemically or biologically cleaved under the condition wherein the desired protein is not denaturated.

A process for the construction of plasmids pGH-TE and pGH-HE, which express a fused protein comprising (Met$^-$ $_1$Phe$^1$-Phe$^{139}$) human growth hormone fragment and (Asn$^{55}$-Ala$^{107}$) SLPI fragment polypeptide, is shown in FIG. 5.

pGH-L9, an expression plasmid of human growth hormone (Proc. Natl. Acad. Sci. USA., 81 5956, 1984) is digested with restriction enzymes BglII and SalI to eliminate a ⅓ downstream part of the human growth hormone gene. On the other hand, a plasmid pUC-D6 comprising (Asn$^{55}$-Ala$^{107}$) SLPI gene is digested with MluI and XhoI to obtain an (Asn$^{55}$-Ala$^{107}$) SLPI gene fragment.

The above-mentioned two fragments, and synthetic DNA linkers (7) and (8), or (9) and (10) (SEQ ID NO:12, 28, 13 and 39respectively), shown in FIG. 4, are ligated using T4 DNA ligase to obtain plasmids pGH-TE and pGH-HE expressing fusion proteins comprising a growth hormone fragment and (Asn$^{55}$-Ala$^{107}$) SLPI fragment. In FIG. 5, pGH-TE is a plasmid expressing a fused protein containing a thrombin-cleaved sequence, and pGH-HE is a plasmid expressing a fused protein containing a hydroxylamine-cleaved sequence.

Figure 15:
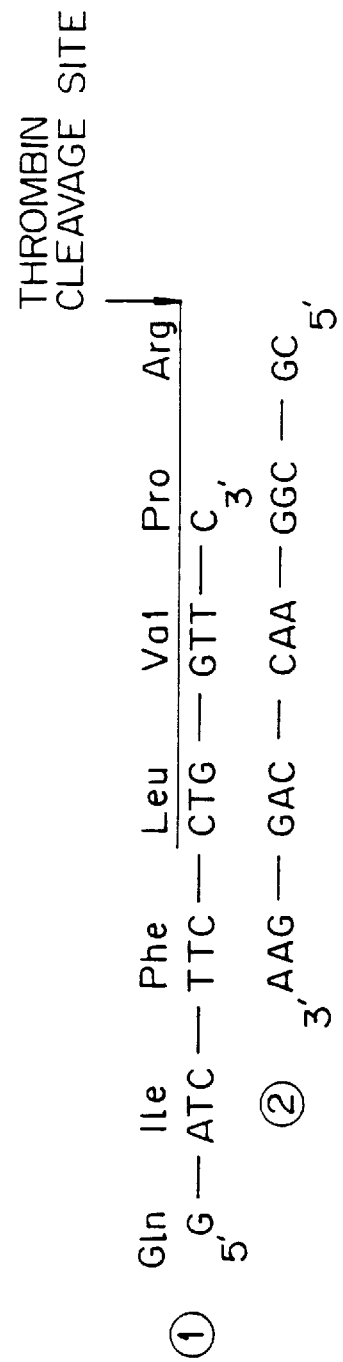
FIG. 15 represents DNA fragments (1) and (2) (SEQ ID NO:16 and SEQ ID NO:30) containing a gene for a thrombin cleavage sequence (SEQ ID NO:17) used in Example 20 (1)
Figure 16:
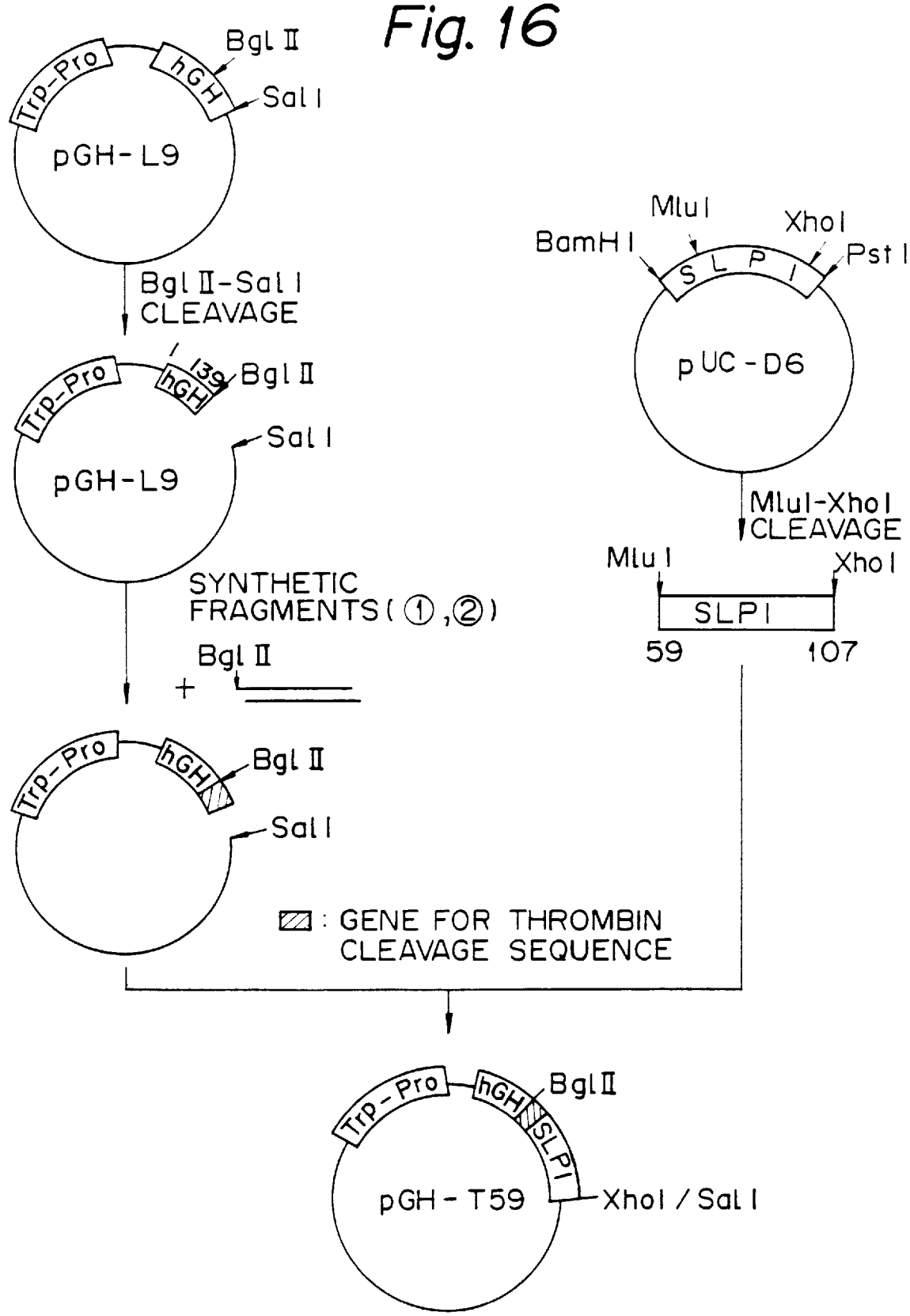
FIG. 16 represents a construction of a plasmid pGH-T59 for the expression of (Arg$^{59}$-Ala$^{107}$) SLPI polypeptide in Example 20 (1)
Figure 17:
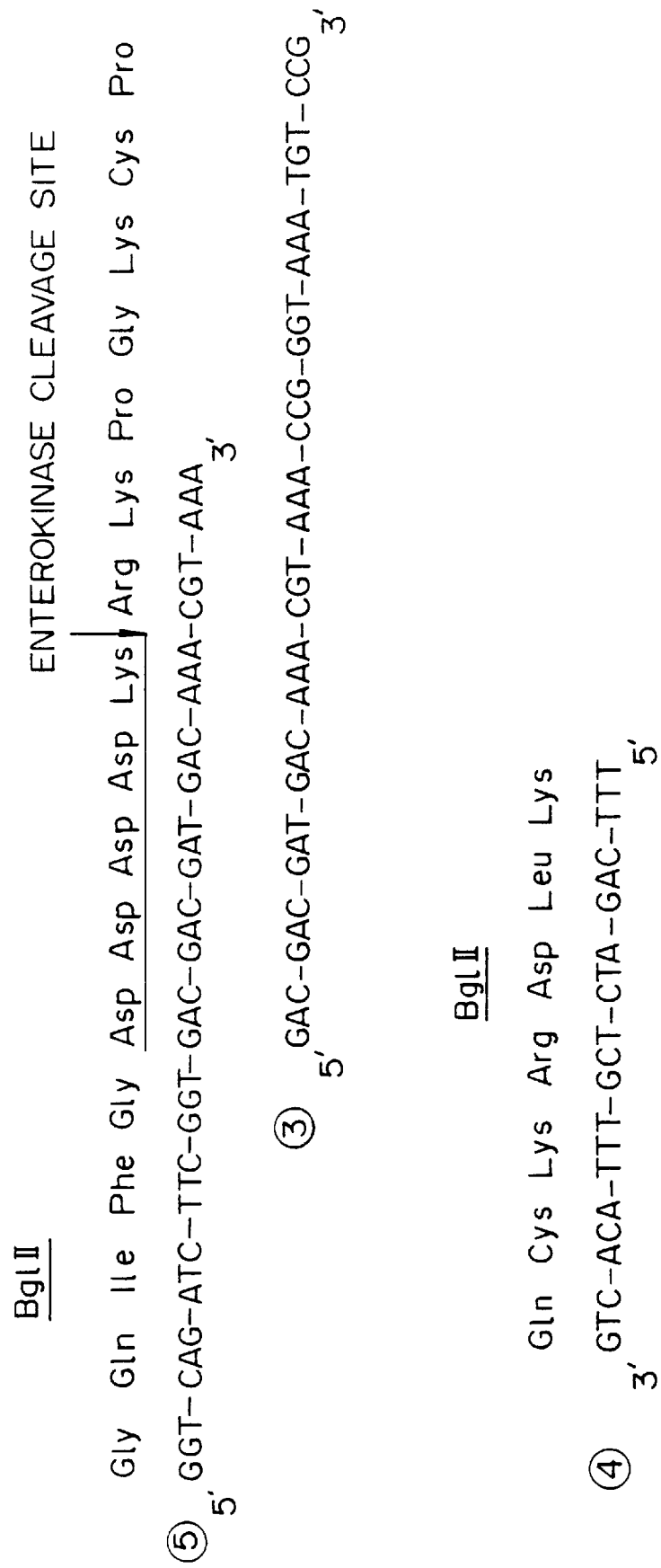
FIG. 17 represents synthetic DNA fragments (3), (4) and (5) (SEQ ID NO:18, SEQ ID NO:19, SEQ ID NO:20) used in Example 20 (2)
Figure 18:
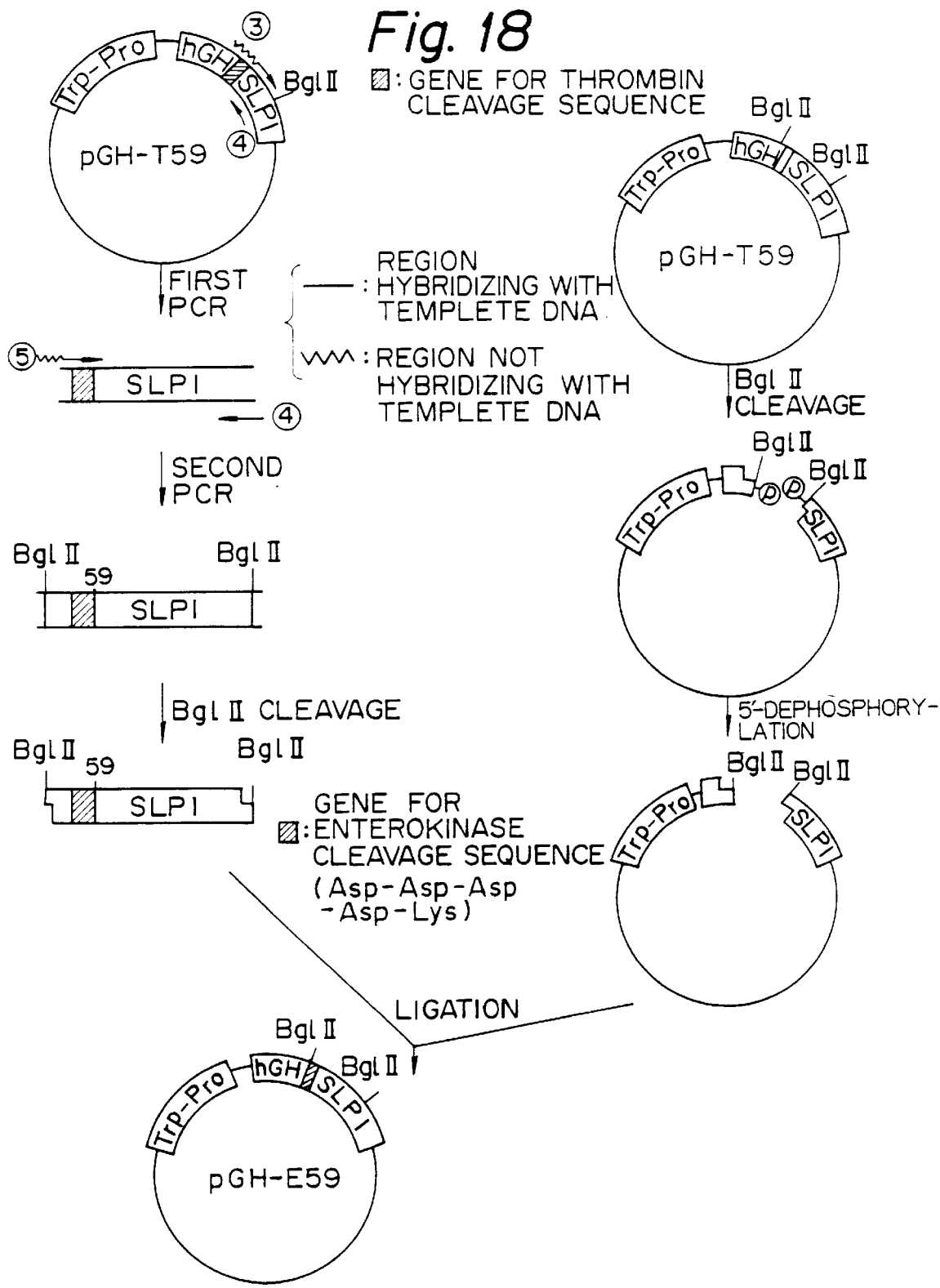
FIG. 18 represents the construction of a plasmid pGH-E59 for the expression of (Arg$^{59}$ -Ala$^{107}$) SLPI polypeptide in Example 20 (2)

Construction of expression plasmids pGH-T59 and pGH-E59 for a fusion protein comprising (Met$^{-1}$Phe$^1$-Phe$^{139}$ human growth hormone fragment and (Arg$^{59}$-Ala$^{107}$) SLPI is shown in FIGS. 16 and 18 respectively. In the expression plasmid, pGH-T59 the carrier protein and the target polypeptide is linked via thrombin-cleavable peptide shown in FIG. 15 (SEQ ID NO:17); and in the expression plasmid pGH-E59, the carrier protein and the target polypeptide is linked via an enterokinase-cleavable peptide (SEQ ID NO:21) shown in FIG. 17.

Figure 24:
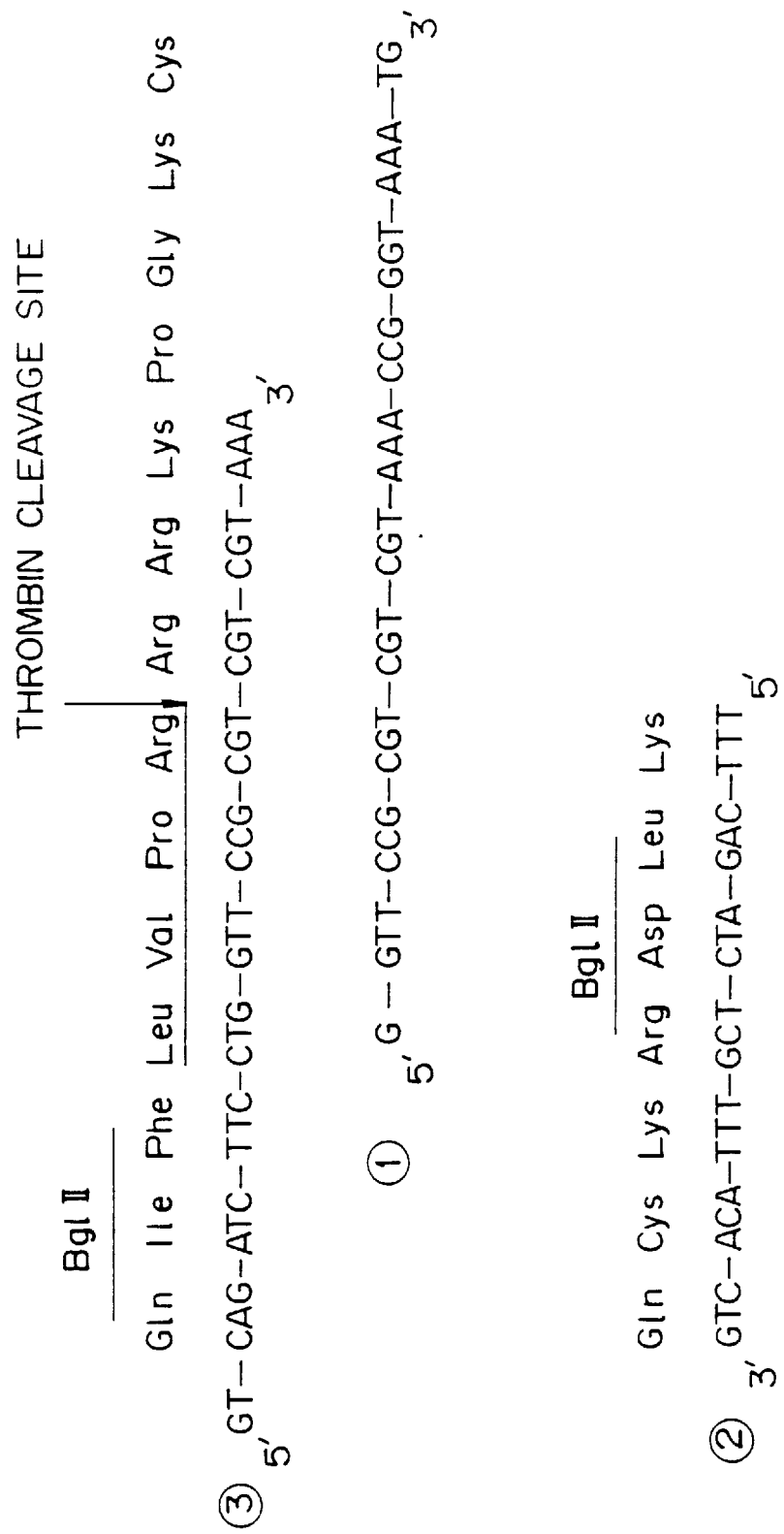
FIG. 24 represents synthetic DNA fragments (1), (2) and (3) (SEQ ID NO:18, SEQ ID NO:19, SEQ ID NO:25) used in Example 31.
Figure 25:
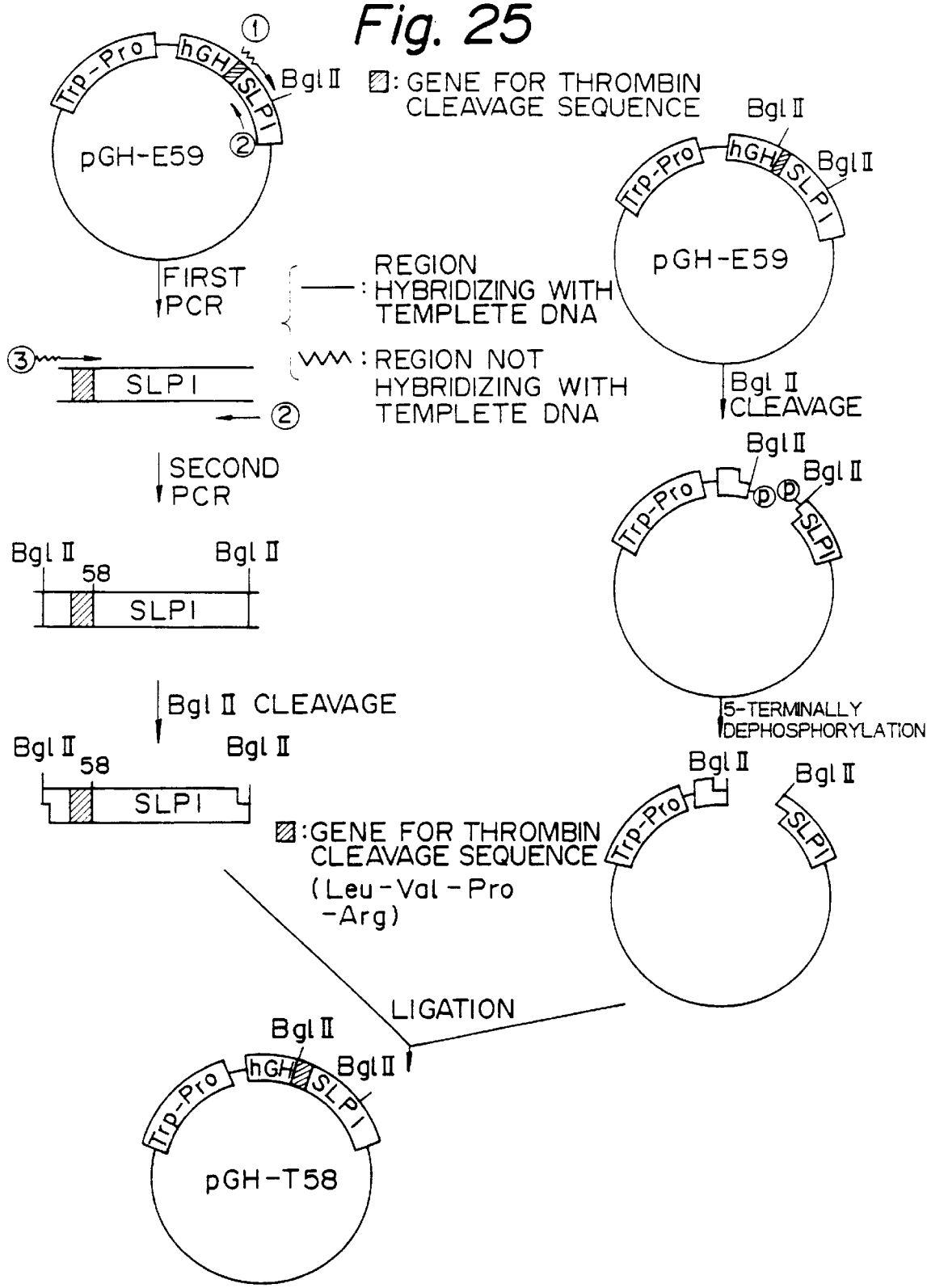
FIG. 25 represents construction of a plasmid pGH-T58 for expression of fusion protein comprising (Arg$^{58}$-Ala$^{107}$) SLPI polypeptide in Example 32.

Construction of expression plasmid pGH-T58 for a fusion protein comprising (Met$^{-1}$Phe$^1$-Phe$^{139}$) a human growth factor fragment and (Arg$^{58}$ -Ala$^{107}$) SLPI is shown in FIG. 25. In the plasmid pGH-T58, the carrier protein and the target polypeptide are linked via a thrombin-cleavable peptide (SEQ ID NO:26) shown in FIG. 24. Moreover, the expression plasmid pGH-T58 may be constructed by linking a human growth hormone gene fragment prepared from a human growth hormone expression plasmid pGH-L9 (Proc. Natl. Acad. Sci. USA., 81 5956, 1984) by deleting C-terminal ⅓ portion of the gene and (Arg$^{58}$-Ala$^{107}$) SLPI gene fragment obtained from SLPI subclone pUC-D6 (see, WO86/06239) via a thrombin-cleavable peptide.

A gene coding for a recognized amino acid sequence which links a gene coding for a desired protein and a gene coding for a human growth hormone or a portion thereof may be any generated gene in a same reading frame with the human growth hormone gene or a portion thereof coding for an amino acid sequence, preferably (Asn-Gly)$_n$ wherein n represents an integer of 1 to 10, which can be easily cleaved by a hydroxylamine treatment to generate a desired protein. Alternatively, it may be any degenerated gene coding for an amino acid sequence, preferably (Val-Pro-Arg)$_n$, (Leu-Val-Pro-Arg)$_n$, or (Asp-Asp-Asp-Asp-Lys)$_n$, wherein n represents an integer of 1 to 10, which can be easily cleaved by a thrombin or enterokinase treatment to generate a desired protein.

To ally a same reading frame between a gene coding for a carrier protein, i.e., human growth hormone or a portion thereof and a recognized amino acid sequence, a synthetic DNA linker can be inserted therebetween.

Genes coding for desired proteins include those genes which code for hormones or factors such as somatomedin, IGF-I, IGF-II, EGF (epidermal growth factor), PDGF (platelet-derived growth factor). Moreover, they are genes coding for lymphokines, enzymes, enzyme inhibitory proteins. For example, interferons, interleukins, neuropeptides, intestinal peptides, blood coagulation factors such as Factor VII, Factor VIIIC, Factor IX, Protein C and Protein S, $\alpha_1$-antitrypsin, SLPI, TIMP (tissue inhibitor of metalloproteinase, and proteins of lung surfactant. Moreover, gene coding for a desired protein include genes coding for an antibody or a portion thereof, and complement or a portion thereof.

Desired proteins may be not only native proteins, but also modified proteins or fragments thereof, and in the latter cases, a gene capable of expressing the modified proteins or fragments thereof may be used.

To prepare a modified protein wherein one or more than one amino acid residues are replaced with one or more other amino acid residues, a gene wherein codons coding for corresponding amino acids have been replaced is used. The codons can be replaced by a conventional procedure which is called "site-directed mutagenesis" (Methods in Enzymology, 154, 367, 1987).

According to the present invention, to obtain an elastase inhibitory polypeptide or homopolymers thereof, a gene coding for a carboxyl-terminal half of SLPI or a gene comprising a two to ten-times repeat of the above-mentioned gene may be used.

A fused protein gene of the present invention may be introduced into an expression plasmid by joining an appropriate promoter downstream thereof. Available promoters include a tryptophan operon promoter (trp promoter), lactose operon promoter (lac promoter), tac promoter, PL promoter, lpp promoter, T7 promoter, and the like. Especially, a 5'-flanking sequence of pGH-L9 wherein a trp promoter and a optimized space between an SD sequence and a translation initiation codon ATG are used, is preferable (Japanese Unexamined Patent Publication No. 60-234584).

For an efficient expression of a fused protein, a trp promoter, SD sequence, translation-initiation codon, gene coding for a human growth hormone or a portion thereof, a gene coding for a linking peptide, a gene coding for a desired protein or a portion thereof, and a translation termination codon, are allied in this order. Such arrived genes are inserted into an appropriate plasmid such as pBR 322 or related plasmid to construct a expression plasmid of a fused protein. Note, a plasmid pBR 322 is preferably used.

Microbial host cells for an expression of the present fused protein gene include E. coli, Bacillus Subtilis, and the like, and E. coli especially preferable. The above-mentioned expression plasmid of a fused protein can be introduced into a microbial cell such as an E. coli cell, by a known method, M. V. Norgard et al., Gene, 3, 279, 1978.

The transformed microorganism thus obtained is cultured in accordance with a method known per se. As a medium, an M9 medium (T, Maniatis ed. Molecular Cloning, p 440, Spring Harbor Laboratory, New York, 1982) containing glucose and casamino acid is mentioned, and if it is necessary to stabilize an expression plasmid in host cells, ampicillin, etc., can be added.

Cell culturing is carried out under a condition suitable for a transformed microorganism, for example, with aeration and agitation by shaking at 37° C. for 2 to 36 hours. Moreover, to stimulate an efficient action of a promoter, an inducing agent such as 3-β-indole acrylic acid (when a trp promoter is used), and isopropyl-β-D-thiogalactoside (when a tac promoter is used), etc., can be added.

After culturing, the transformed microbial cells are collected, for example, by centrifugation, resuspended, for example, in a phosphate buffer, disrupted, for example, by ultrasonication, and centrifugated to easily obtain a fused protein in a pure form. An advantage of the present invention is that the fused protein as such can be cleaved by hydroxylamine or thrombin treatment to generate a desired protein. If necessary, cysteine residues of the fused protein can be sulfonated, followed by treatment with thrombin to generate a sulfonated molecule of the desired protein.

A fused protein joined via an amino acid sequence which can be cleaved by hydroxylamine (including analogs thereof, i.e., compounds which have a structure similar to and an action the same as hydroxylamine) is treated with hydroxylamine under an alkaline condition at 45° C. for two to four hours, or a fused protein joined via an amino acid sequence which can be cleaved by thrombin (including analogs thereof, i.e., enzymes which have a structure similar to and a biological action the same as thrombin) is treated with thrombin at 37° C., for 2 to 24 hours, to generate a desired protein from the fused protein, and isolate the same.

The present polypeptides can be also produced by a conventional chemical synthesis, such as a method using an automatic peptide synthesizer.

The present ($Arg^{58}$-$Ala^{107}$) SLPI may be also produced by cleaving SLPI or derivative thereof with an elastase, and the ($Arg^{59}$-$Ala^{107}$) SLPI may be produced by cleaving SLPI or derivative thereof with saliva. As the starting material, SLPI or derivative thereof, native SLPI derived from human saliva, bronchial secretions, seminal plasma, cervical mucus, partid secretions (R. C. Thompson et al., Proc. Natl. Acad. Sci. USA, 83, 6692–6696, 1986; PCT Japanese National Publication 62-501291, recombinant human SLPI, and recombinant SLPI derivative such as ($Asn^{55}$-$Ala^{107}$) SLPI, and the like are mentioned. As the elastase, polymorphonuclear leucocyte elastase from human sputum, saliva, bronchial secretions, seminal secretions, cervical mucus and the like may be used. The reaction condition is, for example, at 20° to 40° C. for 30 minutes to 72 hours.

The ($Asn^{55}$-$Ala^{107}$) SLPI, or ($Arg^{58}$-$Ala^{107}$)SLPI or ($Arg^{59}$-$Ala^{107}$) SLPI polypeptide of the present invention, i.e., an elastase inhibitory polypeptide, can be isolated and purified from a reaction mixture by an appropriate combination of isolation and purification procedures known per se. These known isolation and purification procedures include methods of using a difference of solubility such as salting out and solvent precipitation; methods mainly using a difference of molecular weight such as dialysis, ultrafiltration, gel filtration, and SDS-polyacrylamide gel electrophoresis; methods using a difference of electric charge such as ion-exchange chromatography, and ion-exchange high performance liquid chromatography; methods using a specific affinity such as affinity chromatography; methods using a difference of hydrophobicity such as a reverse high performance liquid chromatography; and methods using a difference of an isoelectric point such as electrofocusing.

If the prepared protein has tertiary structure via disulfide bonds, it can be converted to a biologically active molecule having the same tertiary structure as a native protein by, for example, a procedure of Chance et al. (R. E. Chance et al., Peptides: Seventh U.S. Peptide Symposium Proceedings, D. H. Rich and E. Gross ed., 721–728, Pierce Chemical Co., Rockford, Ill., 1981) or a procedure described in Japanese Patent Publication No. 2-141523. In a process involving sulfonation by thrombin cleavage, a sulfonated desired protein is reduced, followed by intramolecular disulfide bond formation to prepare a biologically active protein having the same tertiary structure as a native protein.

More specifically, polypeptides of the present invention preferably have four disulfide bonds, i.e., $Cys^{64}$-$Cys^{93}$, $Cys^{92}$-$Cys^{80}$, $Cys^{71}$-$Cys^{97}$, and $Cys^{86}$-$Cys^{101}$, the same as native SLPI. The present invention, however, includes a polypeptide having at least one disulfide bond, as long as it exhibits an elastase inhibitory activity and cathepsin G inhibitory activity, and a reduced immunogenity. The formation of disulfide bonds can be carried out according to a conventional method.

As shown in Table 4, in a comparison of the inhibitory activities of the present elastase inhibitory polypeptide to various proteolytic enzymes, although an elastase inhibitory activity of SLPI is maintained, an inhibitory activities of trypsin-like serine protease such as human thrombin, human plasmin, and human kallikrein are remarkably reduced. Therefore, in comparison to SLPI, an inhibitory activity of elastase over trypsin of the present SLPI polypeptide derivative is improved, so the present polypeptide is promising as a useful clinical medicament.

Since the present protein has an excellent inhibitory activity of a polymorphonuclear leukocyte elastase, it may be used as a therapeutic agent for various diseases involving leukocyte elastase-mediated tissue destruction, such as emphysema, rheumatoid arthritis, glomerulo nephritis, periodontal disease, and amyotrophia, etc., as well as ARDS, neutrocytic allergic lung disease involved in neutrophil, and septicemia.

In particular since the present polypeptide SLPI derivatives exhibit an elastase inhibitory activity and cathepsin G inhibitory activity, and substantially does not exhibit a trypsin inhibitory activity and is expected not to be antigenic because of a native polypeptide, then it can be used as therapeutic agents for various disease, for example, diseases caused by an excess activation of neutrophil, especially diseases caused by neutrophil-released proteases such as elastase and/or cathepsin G, for example, inflammatory diseases, platelet coagulation thrombosis, or ischemia-reperfusion injury, particularly respiratory organ diseases such as chronic bronchitis, diffuse panbronchiolitis, alveolar ectasia, bronchiectasis, bacterial pneumonia, sinusitis, respiratory distress syndrome (RDS), interstitial pneumonia and the like.

The present protein, if necessary, can be lyophilized to form a powder. In this lyophilization, a stabilizer such as sorbitol, mannitol, dextrose, maltose, glycerol, human serum albumin, or the like is used.

The present protein is used for the treatment of the above-identified diseases in the form of a pharmacologically acceptable formulation. The administration routes are oral, or parenteral, for example, intravenous, intramuscular, subcutaneous, percutaneous, rectal, and perrespiratory track (intratracheal, intranasal) administrations, as well as an administration using an iontophoretic device.

For perrespiratory track administration, a liquid or powders for inhalation or spray can be used. If necessary, these formulations may contain a bactericidal agent and antioxidant.

For oral administration, tablets, dragee, granules, powders, a suspension, capsules, and the like may be mentioned. The tablets may be produced according to a conventional procedure using, for example, an excipient such as lactose, starch, crystalline cellulose or the like; binders such as carboxymethylcellulose, methylcellulose, polyvinylpyrrolidone and the like; and disintegrant such as sodium arginate, sodium bicarbonate, sodium lauryl sulfate and the like.

Dragées, powders and granules also can be prepared according to a conventional procedure, using the above-mentioned components.

The liquid and suspension formulations can be prepared according to a conventional procedure, using glycerol esters such as tricaprin, triacetin or the like, and an alcohol such as ethanol. The capsule formulation can be prepared by filling granules, powders or a liquid formulation into capsules such as gelatin capsules.

The formulations for a subcutaneous, intramuscular or intravenous administration are infective aqueous or non-aqueous solution. An aqueous formulation is, for example, a physiological saline, and a nonaqueous formulation is, for example, propylene glycol, polyethylene glycol, olive oil, ethyl oleate or the like, and if necessary, these formulations contain antiseptics and a stabilizer. The infective formulations may be sterilized, for example, by filtration through a bacteria-trapping filter or mixing with a bactericide.

As perdermal formulations, an ointment, cream and the like can be mentioned. The ointment can be prepared according to a conventional process using a fat or oil such as caster oil, olive oil or vaseline and the like. The cream formulations can be prepared according to a conventional procedure using a fatty oil, an emulsifier such as sorbitan monofatty acid ester, or diethylene glycol.

For a rectal administration, a conventional suppository such as a gelatin soft capsule can be used.

An amount of a polypeptide of the present invention to be administered depends on the administration route, and the age and sex of the patient, condition of the disease, and is usually 1 to 5000 mg/application at 1 to 3 applications per day.

Note, in the specification and the drawings, where amino acids and peptides, etc., are described by abbreviations, the symbols used are those according to IUPAC-IUB (Commission on Biological Nomenclature) or symbols conventionally used in the art.

EXAMPLES

Next, the present invention is described in more detail by way of Examples, but the invention is not limited to these Examples.

Note, the various genetic engineering techniques used in the Examples are as follows.

(1) Cleavage of DNA with restriction enzyme (Method 1)

DNA in an amount of 0.1 to 1 µg was dissolved in 10 µl of a restriction enzyme buffer (For MluI or PstI cleavage, 10 mM Tris-HCl, pH 7.5, 10 mM MgCl, 0.1 mg/ml gelatin, 60 mM NaCl, 6 mM mercaptoethanol; for BamHI, BglII, NdeI, SalI, or XhoI cleavage, 10 mM Tris-HCl, pH 7.5, 10 mM MgCl$_2$, 0.1 mg/ml gelatin, 150 mM NaCl and 6 mM mercaptoethanols, all in a final concentration in an aqueous solution), 2 to 4 units of the restriction enzyme was added to the solution, and a reaction was carried out at 37° C. for one hour.

(2) Agarose gel electrophoresis (Method 2)

After the restriction enzyme cleavage, 3 µl of a solution of 0.25% bromophenol blue in 50% aqueous glycerol was added, and an agarose gel electrophoresis (concentration 0.7 to 1%) was carried out.

As an electrophoresis buffer, 90 mM Tris-borate (pH 8.0), 2 mM EDTA aqueous solution was used.

(3) Recovery of DNA fragment from agarose gel (Method 3)

Agarose gel electrophoresis was carried out using a low melting point agarose gel, a band corresponding to a desired DNA was cut out, and the DNA was recovered by a method of L. Weislander et al., Anol. Biochem., 98, 305 (1978).

(4) Ligation using T4 DNA ligase (Method 4)

DNA fragments to be ligated were mixed, and after ethanol co-precipitation, the precipitate was dissolved in 20 µl of a ligation buffer (66 mM Tris-HCl, pH 7.6, 6.6 mM MgCl$_2$, 10 mM dithiothreitol, 1 mM ATP), and 2 to 10 units of T4 DNA ligase was added to the solution, and a reaction was carried out at 16° C. for 12 hours.

(5) Preparation of competent cells and transformation (Method 5)

E. coli was transformed according to a modification of a standard $CaCl_2$ method (M. V. Norgard et al). Namely, an 18-hour culture of E. coli HB101 was inoculated to 5 ml of L medium (1% trypton, 0.5% yeast extract, 0.5% NaCl, pH 7.2), and grown to a turbidity at 600 nm ($OD_{600}$) of 0.3. The cells were twice washed in a cold magnesium buffer (0.1M NaCl, 5 mM $MgCl_2$, 5 mM Tris-HCl, pH 7.6, 4° C.) and resuspended in 2 ml of a cold calcium buffer (100 mM $CaCl_2$, 250 mM KCl, 5 mM $MgCl_2$, 5 mM Tris-HCl, pH 7.6, 4° C.), and the suspension was allowed to stand at 4° C. for 25 minutes. After collection, the cells were suspended in 200 μl of a cold calcium buffer, and the cell suspension was mixed with the solution of the ligation reaction at a ratio of 10:1 (v/v). This mixture was maintained at 4° C. for 60 minutes, 1 ml of an LBG medium (1% trypton, 0.5% yeast extract, 1% NaCl, 0.08% glucose, pH 7.2) was added to the mixture, and cell culturing was carried out at 37° C. for one hour. The culture broth was inoculated to a selection medium (L medium plate containing 30 μg/ml ampicillin) at a ratio of 100 μl/plate. The plate was incubated at 37° C. overnight to grow transformants.

A plasmid DNA was prepared from the resultant ampicillin resistant colonies by a method of Birnboim, H. C. and J. Doly Nucleic Acids Res., 7, 1513 (1979), and digested with appropriate restriction enzymes. The digestion pattern was analyzed by agarose gel electrophoresis to obtain a desired clone.

(6) Determination of DNA nucleotide sequence (Method 6)

DNA sequencing was carried out by a method of Chen, E. Y. and Seeburg, P. H., 4, 165 (1985), using the plasmid DNA as a template and M13 primer M3, RV or pBR322 primer S2 (both from Takara Shuzo, Japan) as a primer, and an M13 sequence kit (Amersham Japan).

(7) Other procedures

All other DNA manipulations were carried out by the methods of Maniatis et al., Molecular Clonings, Cold Spring Harbor Laboratory, New York, 1982.

Example 1

Synthesis and subcloning of structure gene for ($Asn^{55}$-$Ala^{107}$)SLPI polypeptide fragment The gene for the ($Asn^{55}$-$Ala^{107}$) SLPI fragment was designed on the basis of an amino acid sequence of SLPI (SEQ ID NO:4) as shown in FIG. 1 (R. C. Thompson et al., Proc. Natl. Acad. Sci. USA, 83, 6692, 1986; V. Seemuller et al., FEBS Lett., 199, 43, 1986) by choosing codons frequently used in E. coli and providing restriction enzyme recognizing sites at appropriate positions as shown in FIG. 2 for the construction of a desired gene. Next, the designed nucleotide sequence was divided into 3 portions as shown in FIG. 3 to synthesize six oligonucleotides. The oligonucleotides were synthesized using a full automatic DNA synthesizer (Applied Biosystems, Model 381A), by the phosphoamidite method. Synthetic oligonucleotides were purified according to the Applied Biosystems protocol. Namely, synthetic oligonucleotide in an aqueous ammonia was maintained at 55° C. overnight to deprotect amino radicals of bases of DNA, and a higher molecular weight synthetic oligonucleotide fraction was separated by gel filtration using Sephadex G-50 fine gel (Pharmacia). Next, the oligonucleotide fraction was subjected to polyacrylamide electrophoresis (gel concentration 20%, containing 7M urea), and a migration pattern was observed by ultraviolet shadowing. A band corresponding to a desired oligonucleotide was cut out and cut into small pieces, and two to five ml of a DNA eluting buffer (500 mM $NH_4OAc$, 1 mM EDTA, 0.1% SDS, pH 7.5) was added to the gel pieces, and the whole was shaken at 37° C. overnight. An aqueous solution containing the desired oligonucleotide was taken by centrifugation. Finally, the solution containing a synthetic oligonucleotide was applied to a gel filtration column (Sephadex G-50) to obtain a purified synthetic oligonucleotide preparation. Note, if necessary, the polyacrylamide gel electrophoresis was repeated to improve the purity of the synthetic oligonucleotide. The synthetic oligonucleotide in an amount of 0.1 to 1.0 μg was subjected to polynucleotide kinase reaction in the presence of 1 mM ATP, to phosphorylate its 5'-terminal.

The phosphorylation was carried out in a 50 mM Tris-HCl (pH 9.5), 10 mM $MgCl_2$, 5 mM dithiothreitol aqueous solution using 5 units of polynucleotide kinase (P-L Biochemicals). Two synthetic oligonucleotides phosphorylated at the 5'-terminal thereof corresponding to the upper chain and lower chain shown in FIG. 3 were taken into aqueous solution, mixed, and were gradually cooled from 70° C. to room temperature, to anneal the two oligonucleotides.

For subcloning, 1 μg of plasmid pUC119 (Takara Shuzo, Japan) was cleaved with BamHI and PstI by the method 1, the linearized fragments were separated by agarose gel electrophoresis by the method 2, and the linear plasmid was recovered by the method 3. The recovered linear plasmic was mixed with 6 μg of the annealed synthetic fragments (1) and (2), (3) and (4), or (5) and (6), and after ethanol precipitation, were ligated, using a T4 DNA ligase, by the method 4.

The ligation mixture was added to 200 μl of the competent cells of E. coli prepared by the method 5, and transformation was carried out by the method 5. From colonies grown on a selective culture medium (method 5), plasmid DNA was prepared by the method 5. The construction of a desired subclone pUC-D6 containing a carboxy terminal half of SLPI, $Asn^{55}$-$Ala^{107}$, was confirmed by cleaving with a restriction enzyme BamHI, SalI, MluI, NdeI, XhoI or PstI by the method 1, and observing cleavage patterns by agarose gel electrophoresis, by the method 2. Also, the DNA was sequenced by the method 6 to confirm a nucleotide sequence of the subclone.

Example 2

Preparation of plasmid for expression of a fuse protein comprising ($Met^{-1}Phe^{1}$-$Phe^{139}$) human growth hormone fragment and ($Asn^{55}$-$Ala^{107}$) SLPI fragment polypeptide linked via a thrombin cleaved site, and transformant thereof As shown in FIG. 5, 1 μg of an expression plasmid for an expression of human growth hormone gene (M. Ikehara et al., Proc. Natl. Acad. Sci. USA, 81, 5956, 1984) was cleaved with BglII and SalI, and the resulting fragments were separated by agarose electrophoresis by the method 2, and recovered from the gel by the method 3.

Moreover, 2 μg of PUC-D6 obtained in Example 1 was cleaved with MluI and XhoI, the resulting fragments were separated, and a DNA fragment of about 0.15 kbp was recovered by the method 3. On the other hand, DNA fragments (7) and (8) (SEQ ID NO:12 and 28) shown in FIG. 4 coding for an amino acid sequence which can be cleaved by thrombin were chemically synthesized. Next, 1 μg of each of the two DNA fragments recovered as described above, and the annealed synthetic fragments (7) and (8), were mixed, and after an ethanol precipitation, ligation was carried out using a T4 DNA ligase by the method 4, E. coli HB101 was transformed with the ligation mixture by the same procedure as in the Example 1, and from colonies grown on a selective medium, a transformant carrying an expression plasmid pGH-TE of the desired fused protein gene was obtained. The construct of the plasmid pGH-TE was confirmed by the same procedure as in Example 1.

Note, E. coli HB101 containing the plasmid pGH-TE was designated as Escherichia coli HB101 (pGH-TE), and deposited with the Fermentation Research Institute, Agency of Industrial Science and Technology (FRI), Higashi 1-1-3, Tsukuba-shi, Ibaraki-ken, Japan as an international deposition under the Budapest Treaty, as FERM BP-2168 on Dec. 1, 1988.

Example 3

Preparation of plasmid for expression of a fused protein comprising ($Met^{-1}Phe^{1}$-$Phe^{139}$) human growth hormone peptide and ($Asn^{55}$-$Ala^{107}$) SLPI fragment polypeptide linked via a hydroxylamine cleaved site and transformant thereof As shown in FIG. 5, the same procedure as described in Example 2 was repeated except that synthetic DNA fragments (9) and (10) (SEQ ID NO:13 and 29) shown in FIG. 4 coding an amino acid sequence which can be cleaved by hydroxylamine instead of the synthetic DNA fragments (7) and (8) were used to obtain a fused protein expression plasmid pGH-HE, and an E. coli HB101 transformant carrying the plasmid.

Note, E. coli HB101 containing the plasmid pGH-HE was designated as Escherichia coli HB101 (pGH-HE), and deposited with the FRI as an International Deposition under the Budapest Treaty, as FERM BP-2167 on Dec. 1, 1988.

Example 4

Expression of a fused protein gene

E. coli HB101 carrying the fused protein gene expression plasmid pGH-TE and E. coli HB101 carrying the fused protein gene expression plasmid pGH-HE, prepared in Example 2 and 3, respectively, were separately inoculated in an L medium (1% trypton, 0.5% yeast extract, 1% NaCl, pH 7.5, autoclaved) containing 50 to 100 μg/ml ampicillin, and cultured overnight.

M9 medium (0.6% $Na_2HPO_4$, 0.3% $KH_2PO_4$, 0.05% NaCl, 0.1% $NH_4Cl$ aqueous solution, Ph 7.4) containing 0.2% glucose and 5 mg/ml casamino acid was autoclaved, and to the medium were added a separately autoclaved MgSO4 aqueous solution and $CaCl_2$ aqueous solution, to a final concentration of 2 mM and 0.1 mM respectively. To this medium was added the above-mentioned overnight cell culture to 0.1 of $OD_{660}$, and culturing was carried out at 37° C. When the $OD_{660}$ reached 0.5, 3-β-indoleacrylic acid was added to the culture to a final concentration of 40 μg/ml, and culturing was continued with shaking until the $OD_{660}$ reached 1.0 at 37° C. Then, the cells were collected by centrifugation, and washed with a TE buffer (50 mM Tris-HCl, 4 mM EDTA, pH 7.5).

The washed cells were suspended in a 1/10 volume of the TE buffer and disrupted with an ultrasonicator (Kubota Shoji, Type 200M). The disruptant was centrifuged to obtain a precipitate containing a desired fused protein in the form of inclusion bodies. The precipitate was washed with a 0.5% Triton X-100, 1 mM EDTA aqueous solution, washed again with a TE buffer, and dissolved in a 7M urea, 20 mM Tris-HCl (pH 8.0) aqueous solution or 6M guanidine hydrochloride, 20 mM Tris-HCl (pH 8.0). The solution was dialyzed against 20 mM Tris-HCl (pH 8.0) to obtain a fused protein aqueous solution, and to the resulting aqueous solution were added a Tris-HCl buffer (pH 6.8), SDS, and 2-mercapto-ethanol, ethanol, and glycerol to final concentrations of 60 mM, 2%, 4%, and 10%, respectively, and the mixture was subjected to SDS-polyacrylamide gel electrophoresis (O. K. Laemmli, Nature, 227, 650 (1970). The results are shown in FIG. 6. In FIG. 6, lane 1 represents the following molecular weight size maker, lane 2 represents proteins derived from E. coli HB101, lane 3 represents proteins obtained from E. coli HB101/pGH-TE, and lane 4 represents proteins obtained from E. coli HB101 (pGH-HE), all showing electrophoresis profiles.

Note, subsequently the fused proteins were purified by ion exchange chromatography and reverse chromatography.

TABLE 1

| Protein | Molecular Weight |
| --- | --- |
| Lysozyme | 14,400 |
| Soybean trypsin inhibitor | 21,500 |
| Carbonic anhydrase | 31,000 |
| Ovalbumin | 45,000 |
| Bovine serum albumin | 66,200 |
| Phosphorylase B | 92,500 |

Example 5

Cleavage of fused protein with thrombin

To the protein solution obtained in Example 4 by culturing E. coli HB101 containing pGH-TH, thrombin (Sigma) was added in an amount of 1/200 by weight relative to the total protein, and a reaction was carried out at 37° C. for 15 hours. The reaction mixture was treated by the same procedure as in Example 4, and subjected to SDS-polyacrylamide gel electrophoresis. The results are shown in FIG. 7, in lanes 2 to 4. It was confirmed that a fused protein having a molecular weight of about 20,000 was cleaved with thrombin, showing two bands corresponding to a peptide having a molecular weight of about 14,000 derived from a human growth hormone and a desired ($Asn^{55}$-$Ala^{107}$) SLPI fragment polypeptide having a molecular weight of about 6,000. Note, in FIG. 7, lane 1 represents the same molecular weight makers as in FIG. 6.

Example 6

Cleavage of fused protein with hydroxylamine

The protein solution obtained in Example 4 by culturing E. coli HB101 containing pGH-HE was adjusted to final concentrations of 2M hydroxylamine and 0.2M Tris (pH 9.0), and a reaction was carried out at 45° C. for 4 hours. The reaction mixture was treated by the same procedure as in Example 4, and subjected to SDS-polyacrylamide gel electrophoresis. The results are shown in FIG. 7, in lanes 5 to 7. A fusion protein having a molecular weight of about 20,000 was cleaved with hydroxylamine showing two bands corresponding to a polypeptide, having a molecular weight of about 14,000, derived from a human growth hormone and a desired N-terminal glycyl ($Asn^{55}$-$Ala^{107}$) SLPI fragment polypeptide having a molecular weight of about 6,000.

Example 7

From the SDS-polyacrylamide gel obtained in Examples 5 and 6, a band containing the desired SLPI polypeptide fragment was cut out, the polypeptide was extracted with 70% formic acid from the gel, and the extract was filtered, and after filtration, the filtrate was dried under a reduced pressure. The dried sample was dissolved in trifluoroacetic acid, immobilized on a polybrene coated filter according to the protocol of Applied Biosystems, and an amino acid sequence from the N-terminal was determined by cleaving PTH-amino acids from the N-terminal by a protein sequencer (Applied Biosystems 740A) and analyzing the result by a PTH analyzer (Applied Biosystems 120A). The results of the amino acid sequence from the N-terminal are shown in Table 2.

TABLE 2

| Cycle No. | ($Asn^{55}$—$Ala^{107}$) SLPI fragment | Experimental result | |
|---|---|---|---|
| | | Thrombin treatment | Hydroxylamine treatment |
| 1 | Asn | Asn | Gly |
| 2 | Pro | Pro | Asn |
| 3 | Thr | Thr | Pro |
| 4 | Arg | Arg | Thr |
| 5 | Arg | Arg | Arg |

From these results, it is confirmed that an amino acid sequence at an N-terminal of each polypeptide obtained as above conformed to an amino acid sequence of the desired ($Asn^{55}$-$Ala^{107}$) SLPI fragment. That is, it was confirmed that a ($Asn^{55}$-$Ala^{107}$) SLPI fragment polypeptide was correctly liberated by thrombin or hydroxylamine.

Example 8

The elastase inhibitory activities of the above-mentioned expressed fused protein, thrombin-cleaved product, and hydroxylamine-cleaved product were evaluated as follows.

Reagent solution
Buffer: 0.1M HEPES, 1.0M NaCl, 0.1% PEG-600 (pH 7.5)
Elastase (polymorphonuclear leukocyte elastase from human sputum): elastase (EPC Co., Funakoshi Yakuhin) 2 mg/ml of elastase in the buffer (stock solution) was diluted 30,000-fold in said buffer ($1.0 \times 10^{-8}$M).
Substrate solution: 18 mg/ml of MeO-Suc-Ala-Ala-Pro-Val-pNA (Backem) in DMSO (stock solution) was diluted 10-fold in said buffer ($3 \times 10^{-3}$M).

To each well of a 96-well ELISA microplate, were added 140 μl of the above-mentioned buffer, 20 μl of the test sample solution, and 20 μl of the elastase solution. This mixture was stirred at 37° C. for one hour, 20 μl of the substrate solution was added to each well, and a reaction was carried out at 37° C. for one hour to develop same. The absorption at 405 nm was measured and the results are shown in Table 3.

TABLE 3

| Sample | (treatment) | Elastase inhibitory activity |
|---|---|---|
| pGH-L9 | (−) | − |
| /HB101 | (+) | − |
| pGH-TE | (−) | + |
| /HB101 | (+) | + |
| pGH-HE | (−) | + |
| /HB101 | (+) | + |

Fusion protein exhibited an elastase inhibitory activity regardless of the thrombin treatment or hydroxylamine treatment.

Example 9
Sulfonation of cysteine residue of fused protein 250 mg of the fused protein obtained in Example 5 was dissolved in 100 ml of 7M urea, 0.5M Tris-HCl (pH 8.2), and sodium sulfite (Wako Junyaku) was added to the resulting solution to a final concentration of 0.3 mM, and reacted at 45° C. for 30 minutes. Next, sodium tetrathionate (Sigma) was added to a final concentration of 0.05 mM to react at 45° C. for 30 minutes. The reaction mixture was put into a dialysis tube (10K) and dialyzed once against 10 l of water, and twice against 10 l of a 50 mM Tris-HCl buffer (pH 8.5).

Example 10
Cleavage of sulfonated fused protein with thrombin

Figure 8:
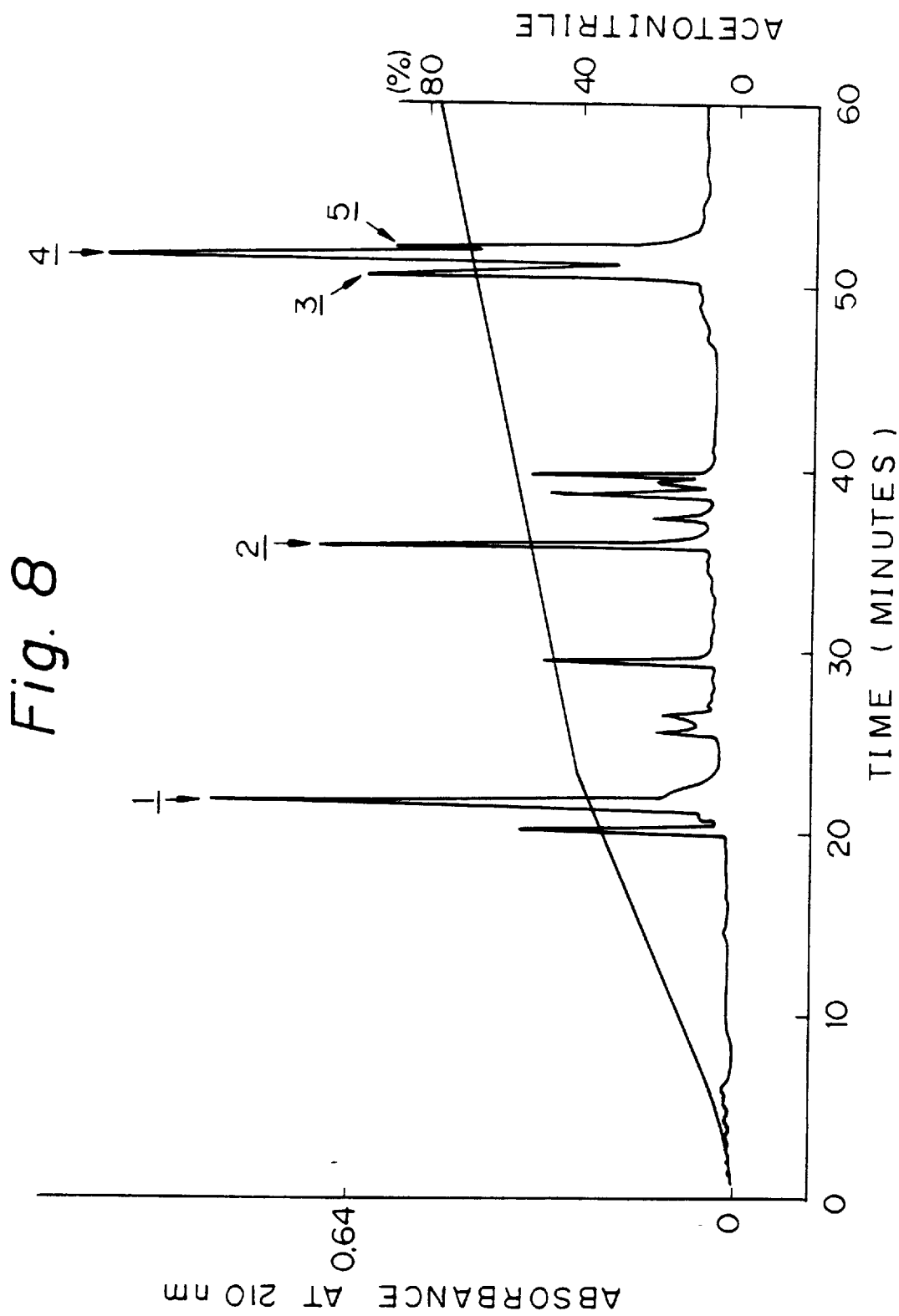
FIG. 8 represents a result of an analysis of a mixture prepared by thrombin treatment of an S-sulfonated fused protein: The main peaks are designated as peaks 1 to 5 in the order of elution.
Figure 9:
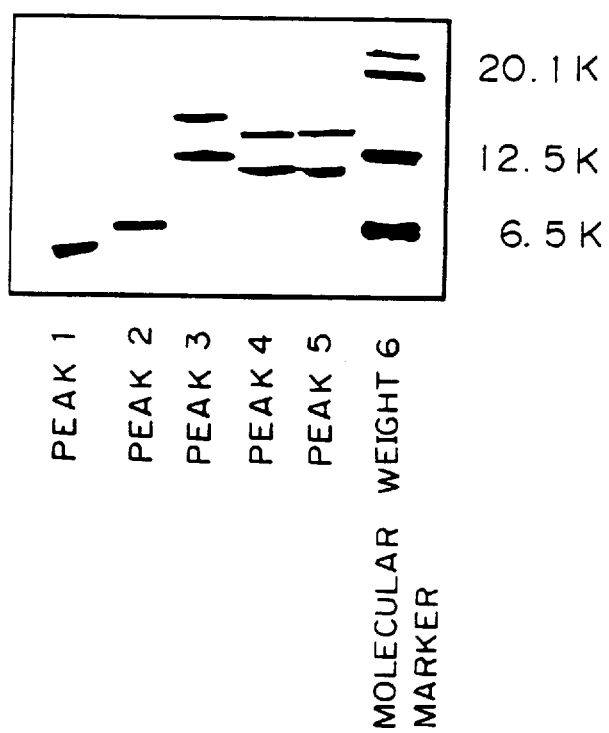
FIG. 9 represents SPS-PAGE profile of the peaks 1 to 5 in FIG. 8.

To the solution of sulfonated fused protein obtained in Example 9, was added calf thrombin (Sigma) in an amount of 1/2000 by weight/weight relative to the total protein, and a reaction was carried out at 37° C. for 12 hours. The results of the reverse HPLC analysis for an aliquot of the reaction mixture are shown in FIG. 8. Moreover, a fraction of each peak was obtained and analyzed by SDS-PAGE. The results are shown in FIG. 9. The N-terminal amino acid sequence for each fraction was determined using a protein sequencer (Applied Biosystems 470A) and a PTH analyzer (Applied Biosystems 470A). The results are shown in Table 4.

TABLE 4

| Peak Number | Cycle Number | | | | | | | | | |
|---|---|---|---|---|---|---|---|---|---|---|
| | 1 | 2 | 3 | 4 | 5 | 6 | 7 | 8 | 9 | 10 |
| 1 | Asn | Pro | Thr | Arg | Arg | Lys | Pro | Gly | Lys | — |
| 2 | Ala | His | Arg | Leu | His | | | | | |
| 3 | | | | | | | | | | |
| 4 | Met | Phe | Pro | Thr | Ile | | | | | |
| 5 | Ala | His | Arg | Leu | His | | | | | |
| ($Asn^{55}$–$Ala^{107}$) SLPI | Asn | Pro | Thr | Arg | Arg | Lys | Pro | Gly | Lys | Cys |

It was found from the above results that the desired sulfonated derivative of the ($Asn^{55}$-$Ala^{107}$) SLPI fragment polypeptide corresponds to peak 1. The peak 1 was obtained using a preparative column (Vydac-214 TP1010), and lyophilized to obtain 2 mg of a sulfonated derivative of the ($Asn^{55}$-$Ala^{107}$) SLPI polypeptide fragment.

Figure 10:
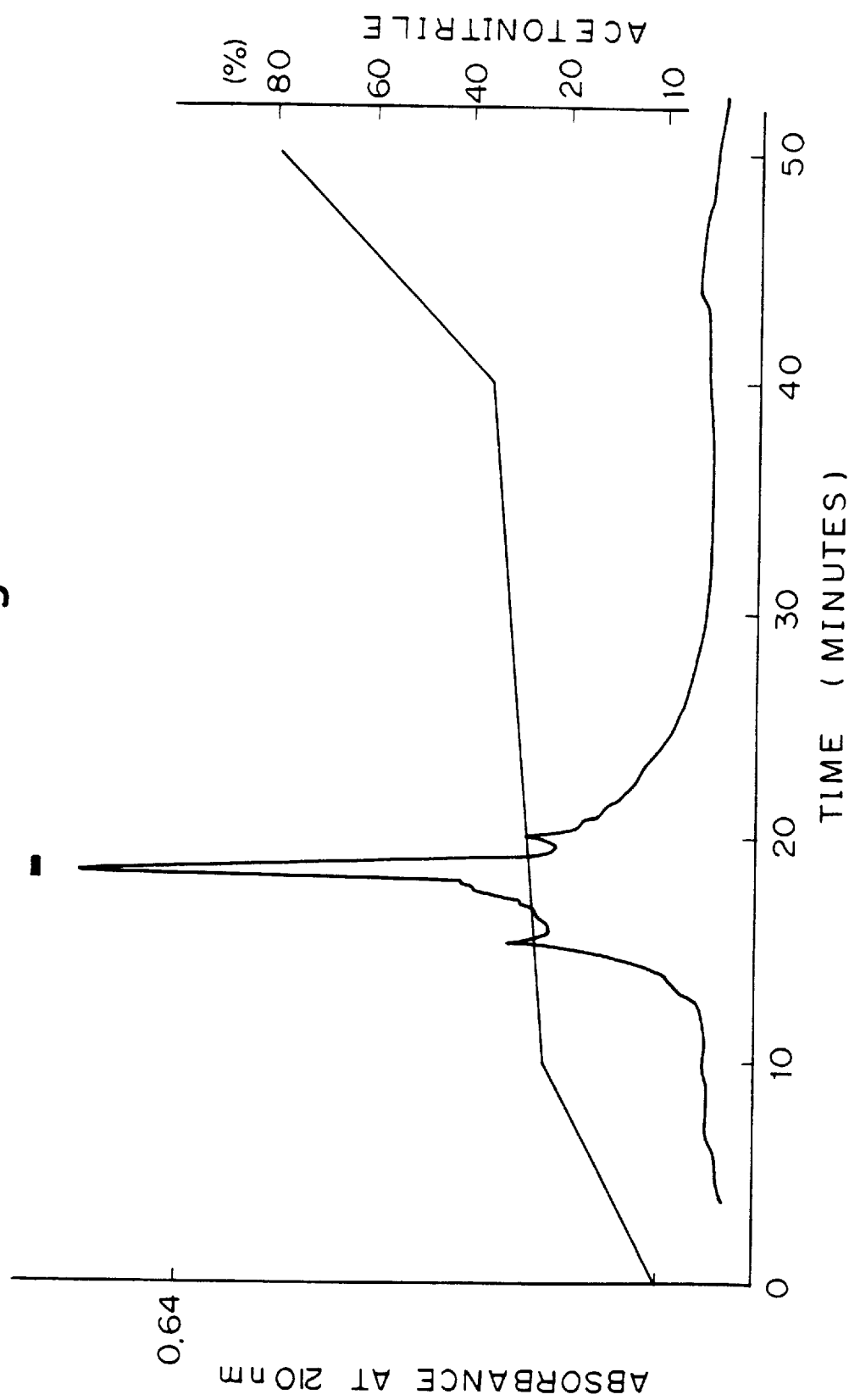
FIG. 10 represents a reverse HPLC elution profile of a refolded (Asn$^{55}$-Ala$^{107}$) SLPI prepared in Example 11.
Figure 11:
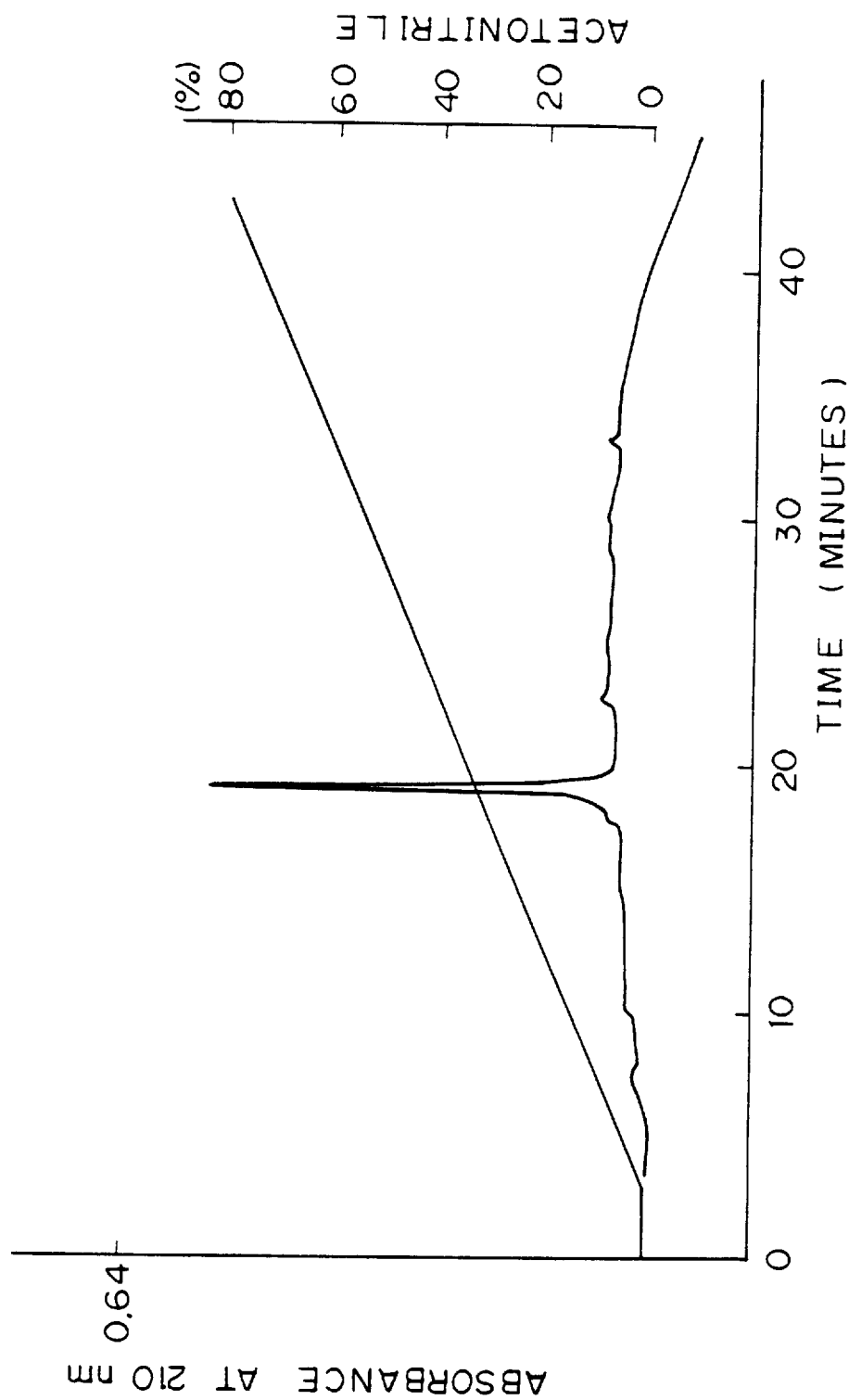
FIG. 11 represents a reverse HPLC analysis of a main peak in FIG. 10 using the same HPLC condition as shown in FIG. 10.

Example 11
Refolding of sulfonated derivative of ($Asn^{55}$-$Ala^{107}$) SLPI polypeptide fragment into active molecule Two mg of a sulfonated derivative of the ($Asn^{55}$-$Ala^{107}$) SLPI polypeptide fragment obtained in Example 10 was dissolved in 1 ml of 50 mM Tris-HCl (pH 8.0), 2-mercaptoethanol was added to the solution to a final concentration of 1%, and a reaction was carried out at 45° C. for two hours. To this solution was added 1 ml of 3M sodium acetate (pH 5.0), and the mixture was put into a dialysis tube and dialyzed against 10 l of a solution containing 50 mM sodium acetate (pH 5.0), 10 μM oxidized glutathione, and 20 μM reduced glutathione, and then dialyzed twice against 10 l of a 50 mM Tris-HCl buffer (pH 8.5). The resulting solution was then subjected to reverse HPLC separation to obtain 1 mg of active-type ($Asn^{55}$-$Ala^{107}$) SLPI fragment polypeptide. The HPLC separation pattern is shown in FIG. 10.

Example 12
Assay of serine protease inhibitory activity of active-type ($Asn^{55}$-$Ala^{107}$) SLPI fragment polypeptide The active-type ($Asn^{55}$-$Ala^{107}$) SLPI fragment polypeptide obtained by refolding by the procedure shown in Example 11 as measured to determine its inhibitory activity to various serine proteases. The assay result thereof is shown as follows.

Buffer: 0.1M HEPES, 1.0M NaCl, 0.1% PEG-6000 (pH 7.5)

Enzyme solution: The following enzymes were dissolved in the above-mentioned buffer solutions at a concentration ten-times higher than the concentration shown in Table 4.
(1) Polymorphonuclear leukocyte elastase from human sputum (EPC Co.; Funakoshi Yakuhin)
(2) Calf pancreatic trypsin (Sigma)
(3) Calf pancreatic chymotrypsin (Sigma)
(4) Porcine pancreatic elastase (Sigma)
(5) Human plasma thrombin (Kabi, Daiichi Kagaku Yakuhin)
(6) Human plasma plasmin (Kabi, Daiichi Kagaku Yakuhin)
(7) Human plasma kallikrein (Kabi, Daiichi Kagaku Yakuhin)

Substrate solution: For the above-mentioned enzymes (1) to (7), the following substrates (1) to (7), respectively, were dissolved in dimethyl sulfoxide to a concentration of 10 mM to prepare stock solutions, which were then dissolved in the above-mentioned buffer solution to concentration ten-times higher than final concentrations, to prepare substrate solutions.

TABLE 5

| Substrate | Final concentration in reaction mixture |
| --- | --- |
| (1) MeO—Suc—Ala—Ala—Pro—Val—pNA$^1$) | 0.3 mM |
| (2) Bz—Arg—pNA$^1$) | 1.0 mM |
| (3) Suc—Ala—Ala—Pro—Phe—pNA$^1$) | 0.1 mM |
| (4) Suc—Ala—Ala—Ala—pNA$^1$) | 0.1 mM |
| (5) H—D—Phe—Pip—Arg—pNA$^2$) | 0.1 mM |
| (6) H—D—Val—Leu—Lys—pNA$^2$) | 0.1 mM |
| (7) H—D—Pro—Phe—Arg—pNA$^2$) | 0.1 mM |

$^{1)}$Backem
$^{2)}$Kabi; Daiichi Kagaku Yakuhin

To each well of a 96-well ELISA microplate were added 140 μl of the above-mentioned buffer, 20 μl of a test solution, and 20 μl of the enzyme solution, and the mixture was stirred at 37° C. for 30 minutes. Next, 20 μl of the substrate solution was added to the well, the mixture was stirred at 37° C. for one hour to develop same, and the absorbance at 405 nm was measured. As inhibitory proteins, an active-type ($Asn^{55}$-$Ala^{107}$) SLPI fragment polypeptide, as well as $\alpha_1$-AT (Sigma), and aprotinin (Boehringer) as a positive control, were used. The inhibitory activities were measured for various concentrations of these proteins to calculate a concentration of inhibitory protein which exhibits a 50% inhibition. The results are shown in Table 6.

TABLE 6

| Enzyme (concentration) | ($Asn^{55}$—$Ala^{107}$) SLPI | $\alpha_1$-PI | Aprotinin |
| --- | --- | --- | --- |
| Polymorphonuclear leucocyte elastase from human sputum ($10^{-9}$ M) | $1 \times 10^{-9}$ M | $3 \times 10^{-9}$ M | $3 \times 10^{-7}$ M |
| Calf pancreatic trypsin ($10^{-7}$ M) | $1.3 \times 10^{-7}$ M | $2 \times 10^{-7}$ M | $1 \times 10^{-7}$ M |
| Calf pancreatic chymotrypsin ($10^{-8}$ M) | $1 \times 10^{-8}$ M | $2 \times 10^{-6}$ M | $5 \times 10^{-8}$ M |
| Porcine pancreatic elastase ($6 \times 10^{-9}$ M) | $2 \times 10^{-7}$ M | $3 \times 10^{-7}$ M | >$2 \times 10^{-6}$ M |
| Human plasma thrombin ($10^{-11}$ M) | >$2 \times 10^{-6}$ M | >$2 \times 10^{-6}$ M | >$2 \times 10^{-6}$ M |
| Human plasma plasmin ($10^{-8}$ M) | >$2 \times 10^{-6}$ M | >$2 \times 10^{-6}$ M | $5 \times 10^{-9}$ M |
| Human plasma kallikrein ($10^{-8}$ M) | >$2 \times 10^{-6}$ M | >$2 \times 10^{-6}$ M | $7 \times 10^{-8}$ M |

Moreover, an inhibitory constant Ki of the present ($Asn^{55}$-$Ala^{107}$) SLPI was calculated on the basis of the above data by a method of Dixon, M. and Webb, E. C. (1979), Enzyme, Longman or a method of Henderson, P. J. F. (1972) Biochem. J., 127, 321–333. The results are shown in Table 7.

TABLE 7

| Enzyme | Dixon method | Henderson method |
| --- | --- | --- |
| Polymorphonuclear leucocyte elastase from human sputum | $3 \times 10^{-11}$ M | $2 \times 10^{-10}$ M |
| Bovine pancreatic trypsin | $6 \times 10^{-8}$ M | $2 \times 10^{-8}$ M |

As seen from Table 7, a ratio of inhibitory constant to polymorphonuclear leucocyte elastase from human sputum [Ki(E)] and inhibitory constant to calf pancreatic trypsin [Ki(T)], i.e., [Ki(T)/Ki(E)] is 1/100 to 1/1000, revealing that a specificity to elastase is increased in comparison to a native SLPI. Note, in a native SLPI, it is known that Ki(E) is roughly equivalent to Ki(T), R. C. Thompson et al., Proc. Natl. Acad. Sci. USA, 83, 6692 (1980).

Example 13
Effect of serum albumin on inhibitory activity

The inhibitory activity of a active-form ($Asn^{55}$-$Ala^{107}$) SLPI fragment polypeptide on polymorphonuclear leucocyte elastase from human sputum was measured by the same procedure as in Example 12 in the presence of 0.8% or 8% calf serum albumin. The calf serum albumin had no effect on its activity and equivalent inhibitory activities were exhibited.

Example 14
Thermal stability

After a solution of an active-type ($Asn^{55}$-$Ala^{107}$) SLPI fragment polypeptide in 50 mM Tris-HCl (pH 7.8) was treated at 50° C. for 2 hours, the inhibitory activity on polymorphonuclear leukocyte elastase from human sputum was measured. The activity was maintained at the same level.

Reference Example 1

Production of SLPI

A DNA segment coding for the amino acid sequence of SLPI was chemically synthesized. Then according to the same procedure as described in W089/06239, the DNA segment was joined to a human growth hormone gene via a DNA coding for Leu-Val-Pro-Arg (SEQ ID NO:8), which can be cleaved with thrombin to prepare an expression vector (plasmid pGH-SLPI), which was then used to transform E. coli HB101. The transformant E. coli 101 (pGH-SLPI) was cultured to obtain inclusion bodies, which were then treated with thrombin, subjected to S—S reconstruction, and purified by chromatography to yield SLPI. The inhibitory constant (Ki) of the resulting SLPI to elastase was $2.5 \times 10^{-10}$M, which was comparable with that of SLPI isolated from a natural source (PCT National Publication in Japan No. 62-501291).

Example 15

Partial Hydrolysis of SLPI with Healthy Human Saliva

Healthy human saliva was filtered through a 0.22 μm filter (Milex GS, Milipore), and in the filtrate was dissolved 1 mg/ml of the SLPI prepared in Reference Example 1. The mixture was then incubated at 37° C. for 30 days. As a control, the SLPI was dissolved in physiological saline (Physisalz; Fuso Yakuhin Kogyo), and the mixture was incubated at 37° C. for 30 days.

Figure 12:
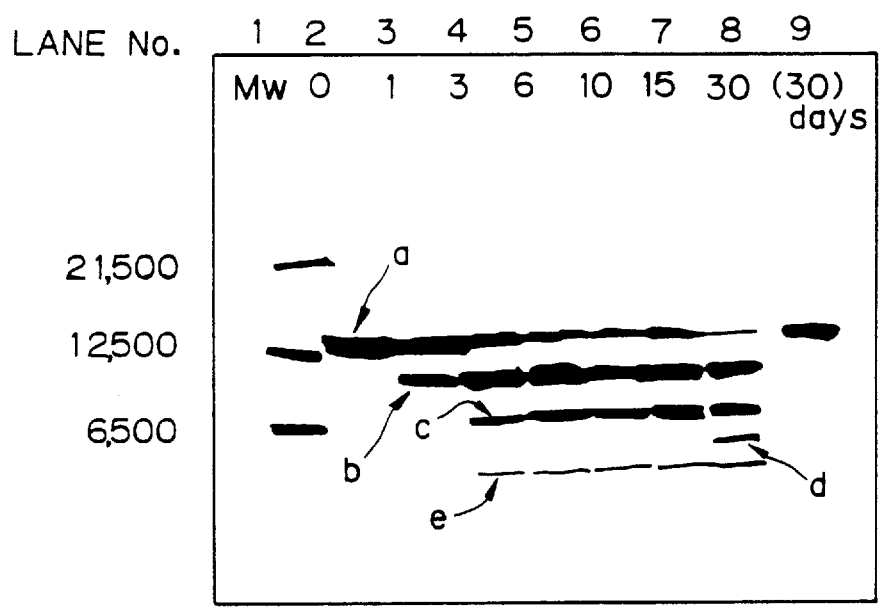
FIG. 12 represents a result of SDS-polyacrylamide gel electrophoresis (PAGE) for treatment of SLPI (MW. about 13,000) with healthy human saliva.

With an elapse of time, samples were taken and to each sample were added a Tris-HCl buffer (pH 6.8), SDS, 2-mercaptoethamel and glycerol, to final concentration of 60 mM, 2% by weight, 4% by weight and 10% by weight, respectively, and the mixture was subjected to an SDS-PAGE (U.K. Laemmli, Nature, 227, 680, 1970). The gel after electrophoresis was stained with Coomussie Brilliant Blue. The results are shown in FIG. 12.

In the Figure, lane 1 shows molecular weight makers, and in Lane No. 2, the band a (MW about 13,000) is of SLPI. As seen from FIG. 12, after one day of incubation at 37° C., a new band b having an MW of about 10,000 appeared, and after 3 days, a band c having an MW of about 7,000 and a band e having an MW about 3,000 were observed. The bank a corresponding to the SLPI having an MW of about 13,000 decreased as time elapid, but bands b,c and e increased. Note, the control, SLPI in physiological saline maintained a band having an MW of about 13,000 during the incubation (lane 9). After incubation at 37° C. for 30 days, the SDS-PAGE showed a band d having an MW of about 5,500.

Next, polypeptides in the polyacrylamide gel thus obtained were electrically transferred to a membrane (Immobilon; Milipore) using a Milli Blot-SDE apparatus. After the transfer, the membrane was stained with 0.1% by weight of Coomassie Blue in 40% by weight methanol/1% by weight acetic acid, and washed with water. Then, after air drying, the bands b, c, d and e were excised, and for each band, the PTH-amino acids were cleaved from the N-terminus with an Applied Biosystems Protein Sequences (Applied Biosystems; 470A) and analysed with a PTH analyser (Applied Biosystems, 120A) to determine an amino acid sequence for 10 amino acids from the N-terminus. The results are shown in Table 8.

TABLE 8

N-Terminal amino acid sequence of products from partially hydrolyzed SLPI

| Amino acid No. from N-terminus | Band | | | |
|---|---|---|---|---|
| | b | c | d | e |
| 1 | Tyr | Tyr | Arg | Met  Leu |
| 2 | Lys | Lys | Lys | Leu  Asn |
| 3 | Lys | Lys | Pro | Asn  Pro |
| 4 | Pro | Pro | Gly | Pro  Pro |
| 5 | Glu | Glu | Lys | Pro  Asn |
| 6 | — | — | — | Asn  Phe |
| 7 | Gln | Gln | Pro | Phe |
| 8 | Ser | Ser | Val | |
| 9 | Asp | Asp | | |
| 10 | Trp | Trp | | |

Note: —: Amino acid could not be identified.
Blank: Amino acid was not identified.

As seen from Table 8, the bands b and c correspond to an amino acid sequence from $Tyr^{21}$ of SLPI; the band d corresponds an amino acid sequence from $Arg^{59}$ of SLPI; and the band e corresponds to amino acid sequences from $Leu^{72}$ or $Met^{73}$ of SLPI. Therefore, it was confirmed that the cleavage sites of SLPI in healthy human saliva are between $Arg^{20}$-$Try^{21}$, $Arg^{58}$-$Arg^{59}$, $Leu^{72}$-$Met^{73}$, and $Met^{73}$-$Leu^{74}$.

Moreover, from the N-terminal amino acid sequences (Table 8) and molecular weights (FIG. 12) of the bands b, c, d and e, it was confirmed that the resulting polypeptides are as follows.

TABLE 9

Identification of Bands b to e

| Band | Amino acid sequence | Molecular weight | |
|---|---|---|---|
| b | ($Tyr^{21}$—$Ala^{107}$) SLPI | about | 10,000 |
| c | ($Tyr^{21}$—$Leu^{72}$) or ($Tyr^{21}$—$Met^{73}$) SLPI | about | 7,000 |
| d | ($Arg^{59}$—$Ala^{107}$) SLPI | about | 5,500 |
| e | ($Met^{73}$—$Ala^{107}$) or ($Leu^{74}$—$Ala^{107}$) SLPI | about | 3,000 |

Example 16

Partial Hydrolysis of ($Asn^{55}$-$Ala^{107}$) SLPI with Healthy Human Saliva

Figure 13:
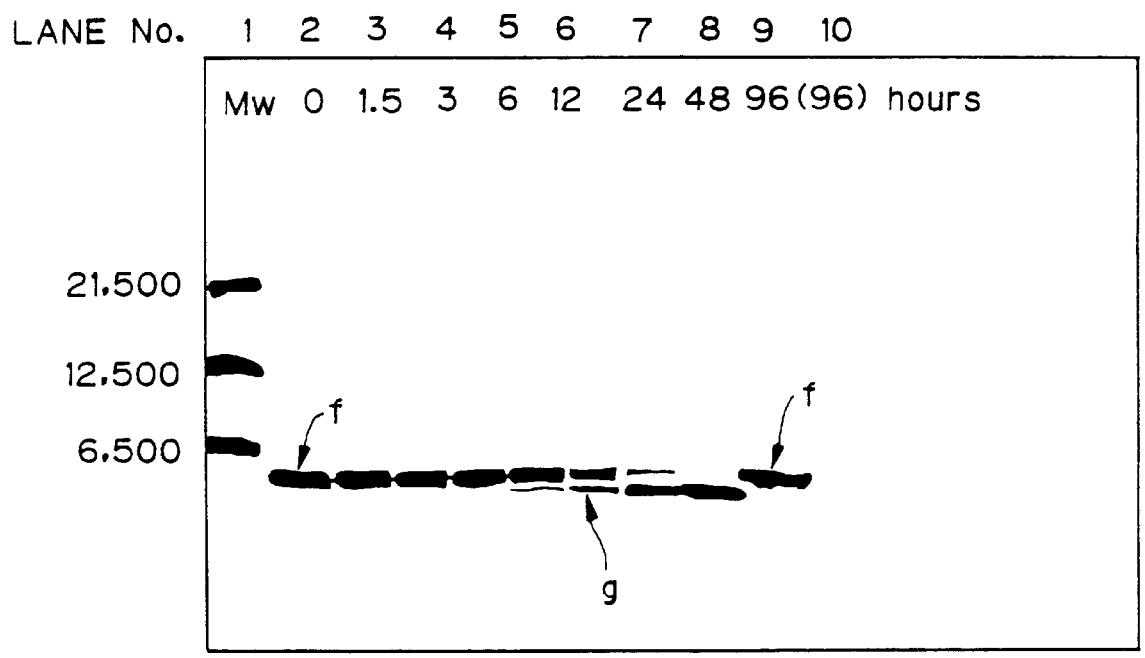
FIG. 13 represents a result of SDS-PAGE treatment of (Asn$^{55}$-Aln$^{17}$) SLPI with healthy human saliva.

According to the same procedure as described in Example 15, ($Asn^{55}$-$Ala^{107}$) SLPI prepared in Example 11 was treated with healthy human saliva at 37° C., and a result is shown in FIG. 13. As seen from FIG. 13. After 12 hours, a new band g (MW about 5,500) appeared. During the incubation of the band f disappeared, and only the band g remained after 96 hours of incubation. Note, after ($Asn^{55}$-$Ala^{107}$) SLPI was incubated in physiological saline without saliva at 37° C. for 96 hours, only the band f having an MW of about 5,800 remained.

Next, according to the same procedure as described in Example 15, the band g was electrically transferred to a membrane and N-terminal amino acid sequence was analyzed. As a result, the N-terminal amino acid sequence was found to be as follow: Arg(1)-Lys(2)-Pro(3)-Gly(4)-Lys(5)-(6)-Pro(7)-Val(8)-Thr(9)-Tyr(10). The 6th amino acid could not be determined. The N-terminal amino acid sequence of the band g corresponds to an amino acid sequence starting from $Arg^{59}$ of SLPI.

As seen from the above, ($Asn^{55}$-$Ala^{107}$) SLPI was cleaved at a site between $Arg^{58}$-$Arg^{59}$, to provide ($Arg^{59}$-$Ala^{107}$) SLPI.

Example 17

Production of )Arg$^{59}$-Ala$^{107}$) SLPI

The polypeptide (Arg$^{59}$-Ala$^{107}$) SLPI was synthesized using an automatic peptide synthesizer (Applied Biosystems 431A), and purified by a reverse chromatography (YMC-PackQDS-AP; YMC). Since the polypeptide thus prepared had non-natural intermolecular disulfide linkages, it was converted to sulfonated (Arg$^{59}$-Ala$^{107}$) SLPI to cleave all disulfide linkages, and subjected to refolding to obtain (Arg$^{59}$-Ala$^{107}$) SLPI having native intramolecular disulfide linkages. The refolding reaction and purification were carried out according to the same procedure as described in Japanese Patent Application No. 2-141523.

Figure 14:
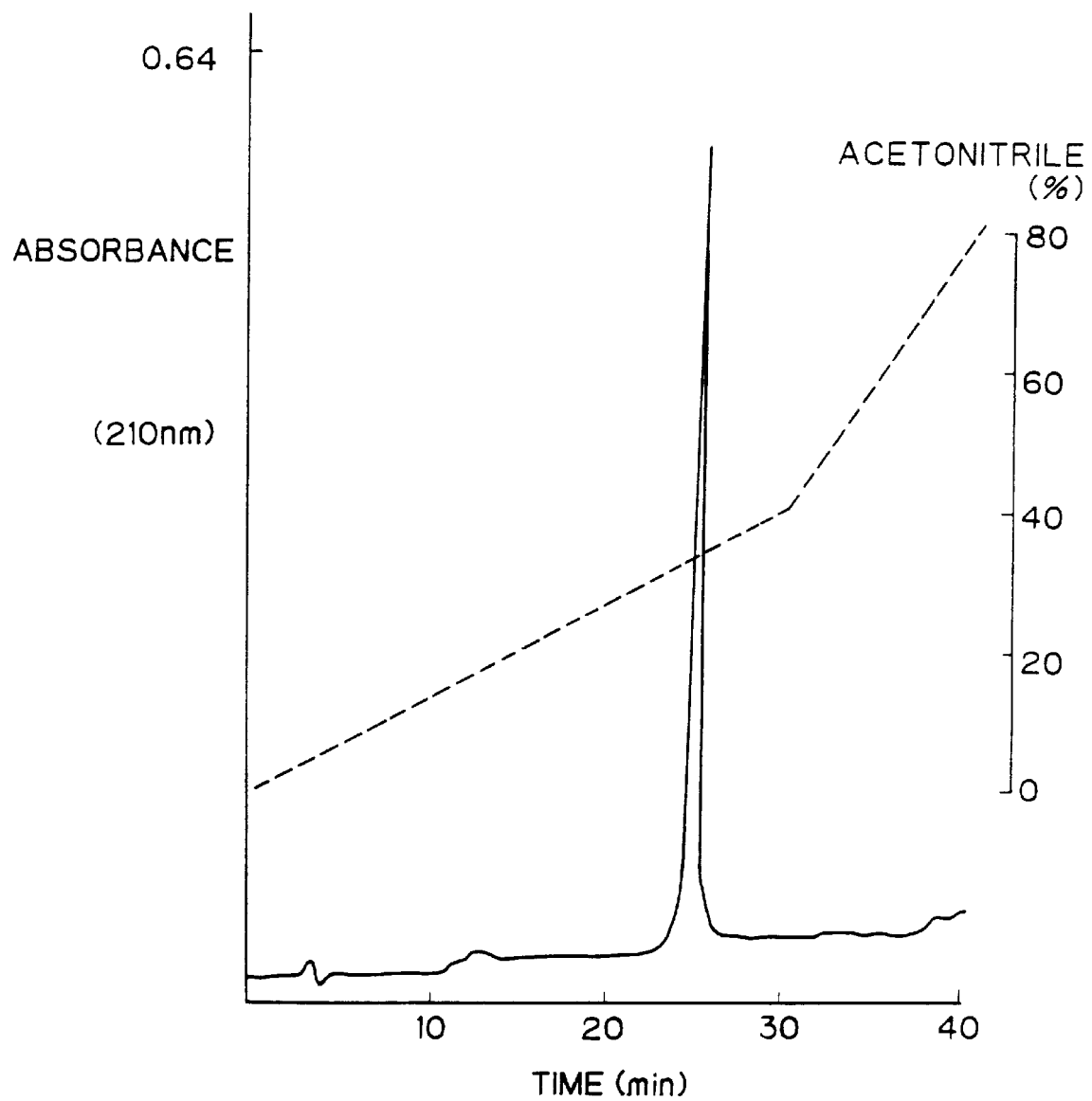
FIG. 14 represents an elution pattern in a reverse chromatography for the peptide (Arg$^{59}$-Aln$^{107}$) SLPI of the present invention, prepared in Example 17.

Namely, 20 mg of the polypeptide synthesized by the automatic peptide synthesizer was dissolved in 20 ml of 0.25M Tris buffer (pH 8.2) containing 3.5M urea, 0.35M Na$_2$SO$_3$ and 0.06M sodium tetrathionate, and reacted at a room temperature. The reaction mixture was purified by reverse chromatography (Protein C$_4$, VYDAC), and lyophilized to obtain 18 mg of sulfonated (Arg$^{59}$-Ala$^{107}$) SLPI. Then, 10 mg of the sulfonated product was dissolved in 50 ml of 0.1M Tris buffer (pH 8.5) containing 0.3 mM oxidated glutathione and 1.5 mM reduced glutathione, and reacted at 4° C. for 7 days. Next, the reduced product was purified by an ion exchange chromatography (S-Sepharose; Pharmacia) and reverse chromatography (Protein C$_4$; VYDAC) to eliminate by-product oligomers formed during the refolding. The purified product was then lyophilized to obtain 7.8 mg of (Arg$^{59}$-Ala$^{107}$) SLPI. The resulting polypeptide was analyzed by reverse chromatography (Protein C$_4$; VYDAC), and as a result, a single peak was eluted, revealing that a single compound was prepared. The elution profile is shown in FIG. 14.

Example 18

Elastase and trypsin inhibitory activities of (Arg$^{59}$-Ala$^{107}$) SLPI (1) Reagent solution Buffer: 0.1M N-(2-hydroxyethyl)piperazine-N'-2-ethansulfonic acid (HEPES), 1.0M NaCl, 0.1% PEG 6000 (pH 7.5)

Enzyme solution: The following enzyme was dissolved in the above buffer to a concentration of 9 hold the concentration shown in Table 10.

(a) Polymorphonuclear leukocyte elastase from human sputum (EPC Co., Funakoshi Yakuhin)

(b) Bovine spleen trypsin (Sigma) Substrate solution: Substrate (c) for the enzyme (a), and substrate (d) for the enzyme (b) were dissolved to a concentration of 9 hold the concentration shown in Table 10. The substrate (c) was dissolved in a mixture of DMSO and the above-mentioned buffer (1:9), and the substrate (d) was dissolved in DMSO.

(c) MeO-Suc-Ala-Ala-Pro-Val-pNA (Bachem)

(d) Bz-Arg-pNA (Bachem)

TABLE 10

| Final concentration of enzyme and substrate for enzyme inhibitory assay | | |
|---|---|---|
| | Enzyme concentration (M) | Substrate concentration (M) |
| For elastase inhibitory assay | (a) 2. 2 × 10$^{-8}$ | (c) 3. 0 × 10$^{-4}$ |

TABLE 10-continued

| Final concentration of enzyme and substrate for enzyme inhibitory assay | | |
|---|---|---|
| | Enzyme concentration (M) | Substrate concentration (M) |
| For trypsin inhibitory assay | (b) 2. 3 × 10$^{-7}$ | (d) 1. 0 × 10$^{-3}$ |

(2) Method

First, 120 μl of buffer solution was put into wells of a 96-well-ELISA microplate, next 20 μl of sample of (Arg$^{59}$-Ala$^{107}$) SLPI obtained in Example 17 was added, followed by 20 μl of enzyme solution. The reaction mixture was stirred at 37° C. for one hour. Next, after an addition of 20 μl of substrate solution, the reaction mixture was stirred at 37° C. for 15 minutes, to be developed, and the absorbance at 405 nm was measured. For reference, SLPI was used. The concentration of (Arg$^{55}$-Ala$^{107}$) SLPI and reference SLPI was varied, and the enzyme inhibitory activities at each concentration were measured to determine which polypeptide concentration exhibits a 50% inhibition (IC$_{50}$ value). The results are shown in Table 11.

TABLE 11

| Elastase and hypsin inhibition of the present polypeptide | | |
|---|---|---|
| | IC$_{50}$ Value (M) | |
| | (Arg$^{59}$—Ala$^{107}$) SLPI | SLPI |
| Elastase | 1. 4 × 10$^{-8}$ | 1. 6 × 10$^{-8}$ |
| Trypsin | 2. 5 × 10$^{-6}$ | 2. 4 × 10$^{-7}$ |

Note, the IC$_{50}$ to elastase of the by-product oligomer formed in Example 17 was 3.0×10$^{-7}$M.

Example 19

Cathepsin G inhibitory activity of (Arg$^{59}$-Ala$^{107}$) SLPI

The cathepsin G inhibitory activity was measured according to Example 18. Namely, 120 μl of buffer solution (0.1M HEPES, 1.0M NaCl, 0.1% PEG 6000, pH 7.5) was added to wells of a 96-well-ELISA microplate, and then 20 μl of a sample of (Arg$^{59}$-Ala$^{107}$) SLPI prepared in Example 17 were added. After the addition of 20 μl of the cathepsin G solution (final concentration 1×10$^{-8}$M), the reaction mixture was stirred at 37° C. for one hour. Next, 20 μl of a substrate solution (Suc-Phe-Pro-Phe-pNA; final concentration 1.1 mM) was added, to be developed, and the absorbance at 405 nm was measured. The concentration of test sample was varied, and the enzyme inhibitory activities were measured to obtain a polypeptide concentration which exhibits a 50% inhibition (IC$_{50}$ value). It was found that the IC$_{50}$ value of (Arg$^{59}$-Ala$^{107}$) SLPI to cathepsin G was 1.1×10$^{-8}$M, revealing a high inhibiting activity to cathepsin G.

Example 20

Construction of expression plasmid for fused protein comprising human growth hormone fragment polypeptide and (Arg$^{59}$-Ala$^{107}$) SLPI polypeptide, and preparation of transformant thereof (1) Expression plasmid wherein a linking peptide comprises a thrombin cleavage sequence (Met$^{-1}$Phe$^{1}$-Phe$^{139}$) human growth hormone expression plasmid pGH-L9 (M. Ikehara et al., Pro. Natl. Acad. Sci.

USA. 81 5956, 1984) was cleaved with BglII and SalI (Takara Shuzo), the resulting fragments were separated by agarose electrophoresis, and a DNA fragment of about 4.75 kbp was recovered by GENECLEAN II KIT (from BIO 101).

Moreover, SLPI subclone PUC-D6 (W089/06239) was cleaved with restriction enzymes MluI and XhoI (Takara Shuzo), the resulting fragments were separated by agarose electrophoresis, and a DNA fragment of about 0.15 kbp was recovered by MERmaid™ kit (from BIO 101).

On the other hand, DNA fragments ((1) and (2) in FIG. 15 (SEQ ID NO: 16 and 30)) were synthesized using a full automatic synthesizer (Applied biosystems Model 392). The synthetic DNA fragments were phosphorylated in the presence of 1 mM ATP using MEGALABEL™ (Takara Shuzo), and the DNA fragments were annealed by heating at 90° C. for 5 minutes and allowed to cool to room temperature, to obtain a double stranded DNA.

For construction of an expression plasmid for a fusion protein, the BglII-SalI DNA fragment of about 4.7 kbp from pGH-L9 and the synthetic double stranded DNA comprising a thrombin cleavage site were ligated at a molar ration of 1:10 using a ligation kit (Takara Shuzo), and the reaction mixture was concentrated in an ultrafree C3HK equipped with a UF filter (Millipore). Next, the ligation product was further ligated with the MluI-XhoI DNA fragment of about 0.15 kbp from PUC-D6, and the ligation product was introduced into E. coli HB101 competent cells, which were then cultured overnight on an LB agar medium containing ampicillin to obtain a transformant (HB/GH-T59) containing a desired fused protein expression plasmid. Plasmid DNA was extracted from the transformant to obtain an expression plasmid pGH-T59 for a fusion protein comprising a human growth hormone fragment and ($Arg^{59}$-$Ala^{107}$) SLPI fragment (FIG. 16). Nucleotide sequence of the DNA was directly confirmed by a Dye Termination kit (Hitachi) using the plasmid DNA as a template and using a Hitachi fluorescent automatic DNA sequencer SQ 3000.

(2) Expression plasmid wherein linking peptide comprises an enterokinase cleavage sequence A polymerase chain reaction (PCR) (Saiki et al. Science, 239 487–491, 1985) was carried out using pGH-T59 (FIG. 16) as a template and synthetic DNA fragments (3) and (4) (SEQ ID NO:19 and 20) (FIG. 17) as primers, and the amplified product was subjected to PCR using synthetic DNA fragments (4) and (5) (SEQ ID NO:20 and 18) (FIG. 17), and the amplified product was cleaved with BglII (Takara Shuzo) to obtain a fragment of about 115 bp. Note, the PCR condition was as follows: after denaturation at 93° C. for 5 minutes, one cycle comprises 93° C., 1.5 minutes; 57° C., 2 minutes; 72° C., 2 minutes; total 30 cycles, followed by 72° C. 7 minutes for termination of reaction.

On the other hand, pGH-T59 was cleaved with BglII (Takara Shuzo), and a BglII-BglII fragment of about 4.6 kbp was separated by agarose gel electrophoresis and recovered by a GENECLEAN II (BIO 101). This BglII-BglII fragment of about 4.6 kbp was dephosphorylated at its 5'-terminus with bacterial alkaline phosphatase (Takara Shuzo) according to a Takara Shuzo protocol.

The dephosphorylated BglII-BglII fragment of about 4.6 kbp was ligated with the PCR-amplified BglII-BglII fragment of about 115 bp using a ligation kit (Takara Shuzo), and the ligated DNA was introduced into E. coli HB101 competent cells (Takara Shuzo), which were then cultured of an LB agar medium containing ampicillin to obtain a transformant (HB/GH-E59) containing a desired fusion protein expression plasmid.

Plasmid DNA was extracted from the transformant, and purified with a QIAGEN (from BIO 101) to obtain an expression plasmid pGH-E59 for a fused protein comprising a human growth hormone fragment peptide, a linker sequence comprising an enterokinase cleavage site, and ($Arg^{59}$-$Ala^{107}$) SLPI polypeptide (FIG. 18). The nucleotide sequence of the plasmid DNA was directly confirmed by Hitachi fluorescent automatic DNA sequencer SQ 3000 using Dye Terminator kit (Hitachi).

Example 21

Expression of fused protein gene

E. coli HB101 containing a fused protein expression plasmid pGH-T59 obtained in Example 20 was cultured overnight in 500 ml of a modified M9 medium (1% ($NH_4$)$_2HPO_4$, 0.3% $K_2SO_4$, 0.3% NaCl) containing 0.25% glucose, 3 mg/ml yeast extract (Difco) and 20 mg/ml casamino acid (Difco) to which, after autoclave sterilization, $MgSO_4$ and $CaCl_2$ were aseptically added to a final concentration of 1 mM. The overnight culture was added to 10 liters of a medium having the same composition to adjust OD660 value to 0.2, and culturing was carried out in a jar fermenter at 37° C. When OD660 reached 20, 3-β-indoleacrylate was added to the culture medium to a final concentration of 150 μg/ml, culturing was further continued at 37° C. for 4 hours. After that E. coli cells were collected by centrifugation, and washed with 0.5M Tris buffer (pH 8.0).

The washed cells were suspended in 0.5M Tris buffer containing lysozyme (1/200 of wet cell weight) and EDTA·3Na (1/20 of wet cell weight), sonicated with a ultrasonicator (Branson, CELL DISRUPTER 900) to disrupt the cells. The sonicated cells were centrifuged to obtain a precipitate containing the desired fused protein as inclusion bodies.

Note, E. coli HB101 containing the plasmid pGH-T59 was designated as a HB/GH-T59, and deposited with the fermentation Research Institute, Agency of Industrial Science and Technology (FRI), under the Budapest Treaty as FERM BP-3863 on May 20, 1992; and E. coli HB101 containing the plasmid pGH-E59 was designated as HB/GH-E59, and deposited with FRI under the Budapest Treaty as FERM BP-3861 on May 20, 1992.

Example 22

Sulfonation of cysteine residues in fused protein and cleavage of sulfonated fused protein with thrombin 25 g of the fused protein obtained in Example 21 was suspended in 200 ml of 0.5M Tris buffer (pH 8.0), and to the suspension were added 240 g of urea to solubilize the fused protein and sodium sulfite (Wako Pure Chemical) to a final concentration 0.7M, and the mixture was reacted at 45° C. for 20 minutes. In addition, sodium 4-thionate (Sigma) was added thereon to a final concentration 0.1M, and reaction was carried out 45° C. for 20 minutes. The reaction mixture was made to 1 liter by adding 10 mM Tris buffer (pH 8.0), and ultrafiltrated (Fuji filter: FILTRON) to make a volume of the mixture to 200 ml. This procedure was repeated 5 times. To the sulfonated fused protein solution thus obtained (the fraction which did not pass through the ultrafiltration membrane) was added 3000 U bovine thrombin (Mochida Seiyaku), and the mixture was reacted at 37° C. for 3 hours. Next, the reaction mixture was ultrafiltrated through a 300K filter, and ($Arg^{59}$-$Ala^{107}$) SLPI sulfonated derivative contained in the filtrate was purified by reverse HPLC (Protein C4, from Vydac), and lyophilized. The N-terminal amino acid sequence of the ($Arg^{59}$-$Ala^{107}$) SLPI sulphonated derivative thus obtained was determined using a protein sequencer (Applied Biosystems 477A).

Example 23
Refolding of (Arg$^{59}$-Ala$^{107}$) SLPI sulfonated derivative to active molecule (disulfide formation)

Figure 19:
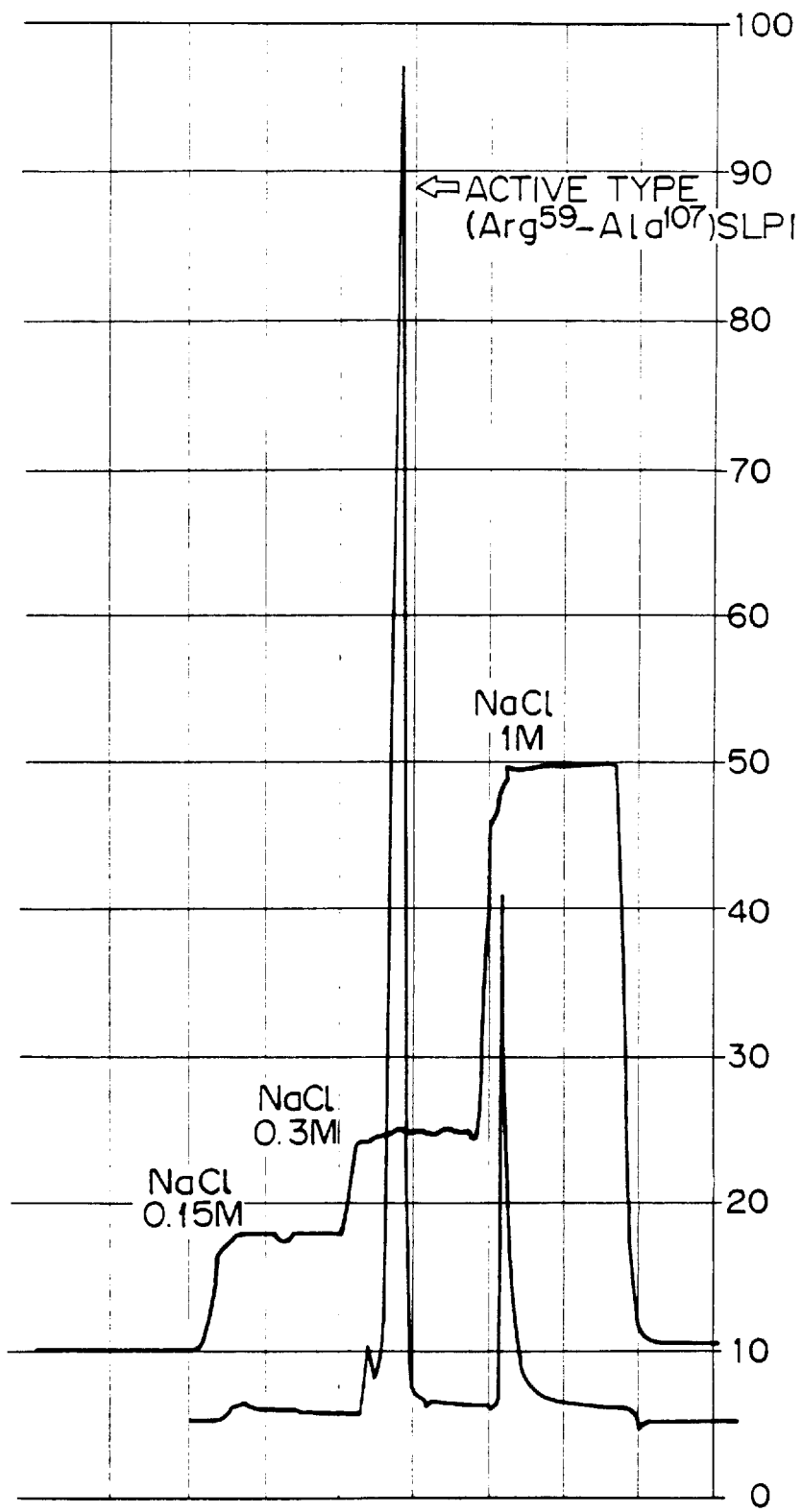
FIG. 19 represents an elution pattern in S-Sepharose ion exchange chromatography for an active type (Arg$^{59}$-Ala$^{107}$) SLPI.

1 g of the (Arg$^{59}$-Ala$^{107}$) SLPI sulfonated derivative obtained in Example 22 was dissolved in 5 liters of a refolding buffer (0.05M Tris-HCl, pH 8.5, 0.3 mM oxidated glutathione, 1.5 mM reduced glutathione), and after reaction of 4° C. for 2 days, the reaction mixture was subjected to S-Sepharose (Pharmacia) ion exchange chromatography. An elution profile is shown in FIG. 19. A desired fraction eluted with 0.3M NaCl was purified by a reverse HPLC (Vydac, Protein C4), and lyophilized to obtain active (Arg$^{59}$-Ala$^{107}$) SLPI.

Example 24
Assay of serine protease inhibitory activity of (Arg$^{59}$-Ala$^{107}$) SLPI (1)

The following assay method was used.

(1) Reagent solution

Buffer: 0.1M (2-hydroxyethyl)piperazine-N'-2-ethansulfonic acid (HEPES), 0.5M NaCl, pH 7.5.

Enzyme concentration: the following enzyme was dissolved in the above-mentioned buffer to a concentration 9 times that shown in Table 12.
- A. Polymorphonuclear leucocyte elastase from human sputum (EPC Co., Funakoshi Yakuhin)
- B. Bovine spleen trypsin (Sigma)
- C. Bovine spleen chymotrypsin (Sigma)
- D. Porcine spleen elastase (Sigma)
- E. Human cathepsin G (EPC Co., Funakoshi Yakuhin)

Substrate solution: for the enzymes A, B, C, D and E, the following substrate a, b, c, d or e, respectively, was dissolved in a solution of DMSO+the above-mentioned buffer (1:9) (note, final concentration of DMSO was 10% in the buffer) to a concentration of 9 times that shown in Table 12.
- a. MeO-Suc-Ala-Ala-Pro-Val-pNA (Bachem)
- b. Bz-Arg-pNA (Bachem)
- c. Suc-Ala-Ala-Pro-Phe-pNA (Bachem)
- d. Suc-Ala-Ala-Ala-pNA (Nakarai Kagaku)
- e. Suc-Phe-Pro-Phe-pNA (Bachem)

TABLE 12

Final concentrations of enzymes and substrates in enzyme inhibitory assay

|  | Enzyme concentration (M) |  | Substrate concentration (M) |  |
|---|---|---|---|---|
| Assay for elastase inhibitor activity | A. | $2 \times 10^{-8}$ | a. | $3.0 \times 10^{-4}$ |
| Assay for trypsin inhibitor activity | B. | $2 \times 10^{-7}$ | b. | $1.0 \times 10^{-3}$ |
| Assay for chymotrypsin inhibitory activity | C. | $1 \times 10^{-8}$ | c. | $1.0 \times 10^{-3}$ |
| Assay for porcine elastase inhibitory activity | D. | $1 \times 10^{-6}$ | d. | $1.0 \times 10^{-3}$ |
| Assay for cathepsin G inhibitory activity | E. | $2 \times 10^{-8}$ | e. | $1.0 \times 10^{-3}$ |

(2) Method

To wells of an ELISA 96-well microtiter plate, were added 120 μl of the buffer and the 20 μl of a sample solution of (Arg$^{59}$-Ala$^{107}$) SLPI obtained in Example 23, followed by 20 μl of the enzyme solution. The mixture was reacted at 37° C. for 10 minutes. Next, 20 μl of the substrate was added, and developed at 37° C. The developed color was measured by absorption at 405 nm.

As a control the same procedure was carried out using SLPI.

An inhibitory activity was expressed by a concentration of inhibitor to be tested which provides 50% inhibition (IC$_{50}$ value). The result is shown in Table 13.

TABLE 13

Serine protease inhibitory activity of the present polypeptide

| | IC$_{50}$ (M) | |
|---|---|---|
| | (Arg$^{59}$-Ala$^{107}$) SLPI | SLPI |
| Human elastase | $1.2 \times 10^{-8}$ | $1.3 \times 10^{-8}$ |
| Trypsin | $2.0 \times 10^{-6}$ | $3.3 \times 10^{-7}$ |
| Chymotrypsin | $5.8 \times 10^{-9}$ | $7.0 \times 10^{-9}$ |
| Porcine elastase | $1.1 \times 10^{-5}$ | $1.3 \times 10^{-5}$ |
| Cathepsin G | $8.0 \times 10^{-9}$ | $5.5 \times 10^{-9}$ |

Example 25

Assay of serine protease inhibitory activity of (Arg$^{59}$-Ala$^{107}$) SLPI (2)

Protein concentration providing 50% inhibitory activity (IC$_{50}$) for (Arg$^{59}$-Ala$^{107}$) SLPI and control SLPI on the following 4 enzymes was determined.

- F. Human plasma thrombin (Sigma)
- G. Human plasma plasmin (sigma)
- H. Human plasma kallikrein (Protogene, Funakoshi Yakuhin)
- I. Porcine FXa (Daichi Seiyaku)

Method for assay was follow.

(1) Reagent solution

Buffer: Buffer solution for each enzyme is as follow.
Thrombin and FXa: 50 mM Tris-HCl, 7.5 mM EDTA-2Na, 175 mM NaCl (pH 8.4)

Plasmin: 50 mM Tris-HCl, 100 mM NaCl (pH 7.4)

Kallikrein: 50 mM Tris-HCl, 361 mM NaCl, 0.01 mg/ml polybrene (pH 7.8)

Enzyme concentration: concentration of each enzyme is shown in Table 14.

TABLE 14

| | Enzyme concentration (M) | Substrate concentration (M) |
|---|---|---|
| Assay for thrombin inhibitory activity | $3 \times 10^{-9}$ | $1.9 \times 10^{-4}$ |
| Assay for plasmin inhibitory activity | $1.0 \times 10^{-7}$ | $8.2 \times 10^{-4}$ |
| Assay for kallikrein inhibitory activity | $1.0 \times 10^{-7}$ | $2.0 \times 10^{-3}$ |
| Assay for Fxa inhibitory activity | $1.0 \times 10^{-8}$ | $4.0 \times 10^{-4}$ |

Substrate solution: for the enzymes F, G, H and I, the following substrate f, g, h or i, respectively, was dissolved to a final concentration shown in Table 14.
- f. H.D-Phe-Pip-Arg-pNA (Kabi Vitrum)
- g. H.D-Val-Leu-Lys-pNA (Kabi Vitrum)
- h. H.D-Pro-Phe-Arg-pNA (Kabi Vitram)

i. Ratio 1:1 mixture of the following compounds:

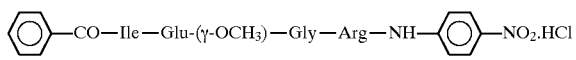

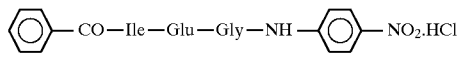

(2) Method

To wells of an ELISA 96-well microtiter plate, were added a solution of $(Arg^{59}\text{-}Ala^{107})$ SLPI obtained in Example 23 and then the enzyme solution, and the mixture was incubated at 37° C. for 10 minutes. Next, the substrate solution was added to develop the color, whose absorption was then measured at 405 nm. As a control, SLPI was used.

(3) Result

Both $(Arg^{59}\text{-}Ala^{107})$ SLPI and SLPI did not exhibit inhibitory activity to all of 4 enzymes at a final concentration up to $\times 10^{-5}$M.

Example 26

Inhibitory constant (Ki) of $(Arg^{59}\text{-}Ala^{107})$ SLPI

Method for assay is as follow.

(1) Reagent solution

Buffer: 0.1M N-(2-hydroxyethyl)piperazine-N'-2-ethanesulfonic acid (HEPES), 1.0M NaCl, 0.1% polyethylene glycol (pH 7.5)

Enzyme solution: the following enzyme was dissolved in the above-mentioned buffer to a concentration 9 times that shown in Table 15.

A. Polymorphonuclear leucocyte elastase from human sputum (EPC Co., Funakoshi Yakuhin)

B. Bovine spleen trypsin (Sigma)

Substrate solution: for the enzymes A and B, the following substrate a or b was dissolved in a solution of DMSO+the above-mentioned buffer (1:9), or in DMSO, respectively.

a. MeO-Suc-Ala-Ala-Pro-Val-pNA (Bachem)
b. Bz-Arg-pNA (Bachem)

TABLE 15

Final concentration of enzyme
and substrate in assay of inhibitory constant

|  | Enzyme concentration (M) | Substrate concentration (M) |
|---|---|---|
| Elastase | $2.0 \times 10^{-8}$ | $3.0 \times 10^{-4}$ |
| Trypsin | $2.0 \times 10^{-7}$ | $1.1 \times 10^{-3}$ |

(2) Method

To wells of an ELISA 96-well microtiter plate, were added 120 μl of the buffer, 20 μl of a sample solution of $(Arg^{59}\text{-}Ala^{107})$ SLPI obtained in Example 23, and 20 μl of the enzyme solution in this order, an the mixture was reacted at 37° C. for 1 hour. Next, 20 μl of the substrate was added to develop at 25° C. Absorption of the developed color was measured at 405 nm. As a control, SLPI was used.

On the basis of the result thus obtained, an inhibitory constant (Ki) of $(Arg^{59}\text{-}Ala^{107})$ SLPI of the present invention was calculated according to the method of Henderson (Henderson, P. J. F. (1972), Biochem. J. 127, 321–333). The result is shown in Table 16.

TABLE 16

Inhibitory constant (Ki) to serine protease

| | Inhibitory constant (Ki) (M) | |
|---|---|---|
| | $(Arg^{59}\text{-}Ala^{107})$ SLPI | SLPI |
| Elastase Ki (E) | $0.8 \times 10^{-10}$ | $0.8 \times 10^{-10}$ |
| Trypsin Ki (T) | $1.1 \times 10^{-6}$ | $3.3 \times 10^{-8}$ |

As seen from Table 16, a relative ratio of an inhibitory activity of the present $(Arg^{59}\text{-}Ala^{107})$ SLPI on trypsin to that on elastase (Ki(T)/Ki(E)) is about 14,000. This means that $(Arg^{59}\text{-}Ala^{107})$ SLPI substantially does not exhibit inhibitory activity to trypsin.

Example 27

Treatment of SLPI with Polymorphonuclear leucocyte elastase from human sputum

Polymorphonuclear leucocyte elastase from human sputum (EPC, Funakoshi Yakuhin) and SLPI were separately dissolved in a buffer (0.1M HEPES, 0.1M NaCl, 0.1% PEG 6000, pH 7.5) and the elastase solution was added to the SLPI solution, and the mixture was incubated at 37° C. Samples were taken as time elapsed, and to each sample were added Tris-HCl buffer (pH 6.8), SDS, 2-mercaptolethanol, glycerol, and Coomassie Brilliant Blue to final concentrations of 50 mM, 4 w/v %, 2 v/v %, 12 v/v % and 0.01 w/v % respectively. The mixture was subjected to SDS-polyacrylamide gel electrophoresis using Tricine (Sigma) as a polar buffer (Schagger, H., Anal. Biochem. 166, 368, 1987). After the electrophoresis, the gel was stained with Coomassie Brilliant Blue G-250, and decoloured with 50% (v/v) methanol/10% (v/v) acetic acid.

Figure 20:
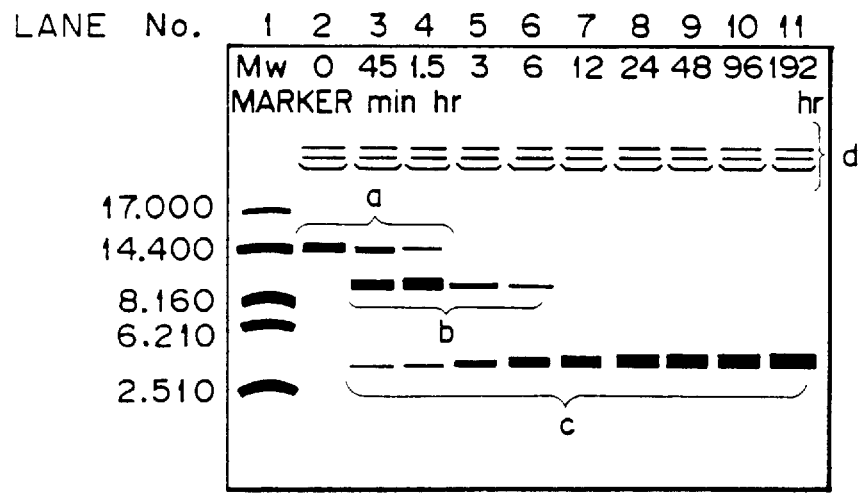
FIG. 20 represents the result of SDS-PAGE of a partial decomposition product formed by treatment of SLPI with twice the amount of human polymorphonuclear leucocyte elastase as in Example 27; in the Figure, the bands indicated by (a) are a bands of SLPI (MW. about 14,000), the bands (b) are a partial decomposition product (Ala$^{16}$-Ala$^{107}$) SLPI, the bands (c) are bands of the present polypeptide (Arg$^{58}$-Ala$^{107}$) SLPI (MW. about 5,500), and a series of bands (d) represent elastase.

(1) A result of a test, wherein elastase was added to 100 μM SLPI to an elastase final concentration of 200 μM, and the mixture was incubated at 37° C. up to 192 hours taking samples as time elapsed, is shown in FIG. 20. In FIG. 20, the band a of SLPI (showing a molecular weight of about 14,000 on an SDS-PAGE) in lane 2 rapidly disappeared after 45 minute incubation, while the band b (molecular weight of about 11,000) appeared from 45 minutes, and was observed up to 6 hours. Moreover the band c corresponding to a molecular weight of about 5,000 gradually increased from 45 minutes, and maintained an approximately similar band concentration from 6 hours to 8 days at 37° C.

Figure 21:
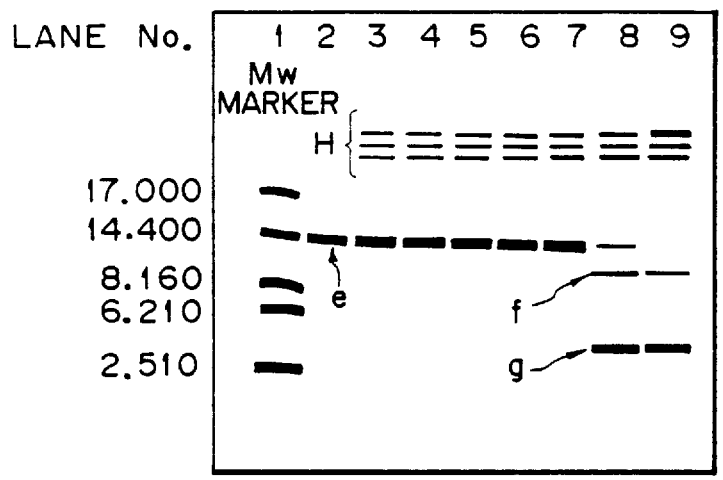
FIG. 21 represents the result of SDS-PAGE of a partial decomposition product formed by treatment of SLPI with different concentrations of human polymorphonuclear leucocyte elastase, wherein lanes 3 to 9 show results wherein elastase in concentration between 13 μM and 200 μM was added to 50 μM SLPI, and for each lane, a 5 μl sample was analyzed; in the Figure, the line (e) of bands shows bands of SLPI (MW. about 14,000), the line (f) of bands shows bands of a partial decomposition product (Ala$^{16}$-Ala$^{107}$) SLPI, the line (g) of bands shows bands of the present polypeptide (Arg$^{58}$-Ala$^{107}$) SLPI, and the group of bands H shows bands of elastase.

(2) A result of a test, wherein to 50 μM SLPI was added elastase sequentially diluted by 2 fold from 200 μM, and each mixture was incubated at 37° C. for one hour, as shown in FIG. 21. As seen from FIG. 21, in tests wherein not less than 100 μM final concentration of elastase was added to 50 μM SLPI, the band e of SLPI disappeared significantly. It is clear that the band f (molecular weight about 11,000) and the band a (molecular weight about 5,000) were new bands, and appeared as the band e disappeared. Therefore, it is considered that the bands f and a were degradation products of SLPI.

(3) Next, polypeptides thus generated were electrically transferred to a membrane (Immobilon-p$^{SQ}$ Millipore) using a Milli Blot-SDE apparatus (Millipore). After the transfer, the membrane was stained with 0.1 (w/v) % Coomassie Blue/40 (v/v) % methanol/(1 v/v) % acetic acid, and washed with water. After drying, relevant bands were cut out, and the peptide was cleaved from the N-terminal using an Applied Biosystems Protein-Sequencer (Applied Biosystems; 477A), and after PTH-conversion, the resulting amino acid derivatives were analyzed by a PTH-Amino acid analyzer (Applied Biosystems, 120A) to determine the N-terminal amino acid sequence. A result is shown in Table 17.

TABLE 17

N-terminal amino acid sequence partial decomposition products of SLPI with elastase

| Position from N-terminal | Bands | | | |
|---|---|---|---|---|
| | b | c | f | g |
| 1 | Ala | Arg | Ala | Arg |
| 2 | Glu | Arg | Glu | Arg |
| 3 | — | Lys | — | Lys |
| 4 | Leu | Pro | Leu | Pro |
| 5 | Arg | Gly | Arg | Gly |

From Table 17, the bands b and f conform to an amino acid sequence starting from $Ala^{16}$ of SLPI, and the band c and a conform to an amino acid sequence starting from Arg of SLPI. Accordingly, it was confirmed that selective cleavage sites of SLPI with an elastase from human sputum were the sites between $Ser^{15}$-$Ala^{16}$, and $Thr^{57}$-$Arg^{58}$.

Moreover, from the N-terminal amino acid sequences of the bands c and g (Table 17) as well as the decomposition pattern and molecular weight (FIGS. 20 and 21), it was confirmed that these polypeptides were those shown in Table 18.

TABLE 18

Identification of partial decomposition product of SLPI with elastase

| Bands | Amino acid sequence | Molecular weight |
|---|---|---|
| b and f | ($Ala^{16}$-$Ala^{107}$) SLPI | About 11,000 |
| c and g | ($Arg^{58}$-$Ala^{107}$) SLPI | About 5,500 |

Example 28

Figure 22:
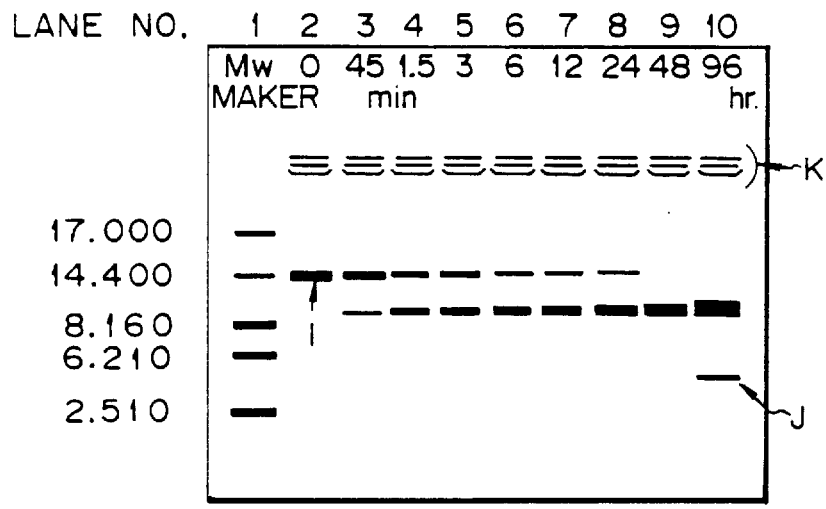
FIG. 22 represents a result of SDS-PAGE of a partial decomposition product formed by simultaneous treatment of SLPI with healthy human saliva and polymorphonuclear leucocyte elastase from human sputum in Example 28; in the Figure, the line I of bands are bands of SLPI (MW. about 14,000), the band J is a band of the present polypeptide (Arg$^{58}$-Ala$^{107}$) SLPI (MW. about 5,500), and the group K of bands shows elastase.

Simultaneous treatment of SLPI with healthy human saliva and polymorphonuclear leucocyte elastase from human sputum (1) Healthy human saliva was ultra-filtered through a 0.22 $\mu$m filter (Millex GS, Millipore), and to the filtered saliva were added SLPI and polymorphonuclear leucocyte elastase from human sputum (EPC, Funakoshi Yakuhin) to a final concentration of 50 $\mu$M respectively. The mixture was incubated at 37° C., samples were taken as time elapsed, and analyzed by SDS-PAGE as described in Example 27. The result is shown in FIG. 22. As seen from FIG. 22, in the case where SLPI (molecular weight, about 14,000) shown as band I in lane 2 was incubated in saliva in the presence of the same concentration of elastase at 37° C., after 96 hours, a new band J with a molecular weight of about 5,500 appeared.

(2) Next, the band J was transferred to a membrane as described in Example 27, and N-terminal amino acid sequence was analyzed. The result is shown in Table 19. From this result, the N-terminal sequence of the band J completely conformed to an amino acid sequence of SLPI starting from $Arg^{58}$.

Therefore, it was confirmed that SLPI was cleaved at the site between $Thr^{57}$-$Arg^{58}$ of SLPI in healthy human saliva which is fluid of exocrine gland and in the presence of elastase at the same concentration as that of SLPI. Moreover, from the molecular weight (about 5,500) of the band J in FIG. 22 and the N-terminal sequence in Table 19, it was confirmed that the band J is a ($Arg^{58}$-$Ala^{107}$) SLPI polypeptide.

TABLE 19

Amino acid sequence of a partial decomposition product of SLPI with saliva and elastase

| Position of N-terminal amino acid | Band J |
|---|---|
| 1 | Arg |
| 2 | Arg |
| 3 | Lys |
| 4 | Pro |
| 5 | Gly |

Example 29

Simultaneous treatment of ($Asn^{55}$-$Ala^{107}$) SLPI with healthy human saliva and polymorphonuclear leucocyte elastase from human sputum (1) According to the same procedure as described in Example 28, to healthy human saliva were dissolved SLPI and polymorphonuclear leucocyte elastase from human sputum to final concentrations of 50 $\mu$M and 100 $\mu$M respectively, and the mixture was incubated at 37° C. Samples were taken as time elapsed, and analyzed by SDS-PAGE.

Figure 23:
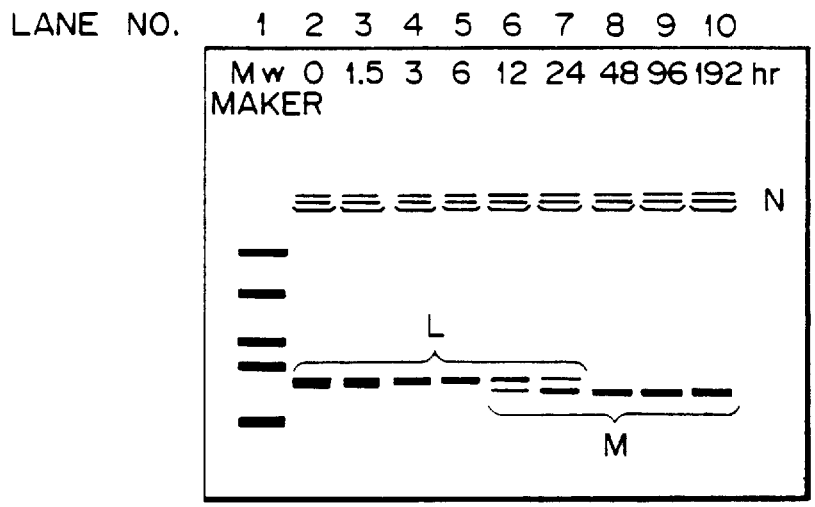
FIG. 23 represents the result of SDS-PAGE of a partial decomposition product formed by simultaneous treatment of (Asn$^{55}$-Ala$^{107}$) SLPI with healthy human saliva and polymorphonuclear leucocyte elastase from human sputum in Example 29; in the Figure, the line L of bands are bands of (Asn$^{55}$-Ala$^{107}$) SLPI (MW. about 5,800), the line M of bands are bands of the present polypeptide (Arg$^{58}$-Ala$^{107}$) SLPI, and the group N of bands shows elastase.

The result is shown in FIG. 23. Simultaneous treatment of ($Asn^{55}$-$Ala^{107}$) SLPI (molecular weight about 5,800, band L) with healthy human saliva and elastase provided band M having a molecular weight slightly lower than that of band L after 12 hours at 37° C. An amount of the band L gradually decreased, and after 48 hours, almost only band M was observed.

(2) Next, N-terminal amino acid sequence of the band M was analyzed as described in Example 27. The result is shown in Table 20.

From this result, N-terminal amino acid sequence of the band M was an amino acid sequence of SLPI starting from $Arg^{58}$. Accordingly, ($Asn^{55}$-$Ala^{107}$) SLPI was cleaved at the site between $Thr^{57}$-$Arg^{58}$ by a simultaneous treatment with healthy human saliva and elastase, and converted to ($Arg^{58}$-$Ala^{107}$) SLPI.

TABLE 20

Amino acid sequence of partial decomposition product of ($Asn^{55}$-$Ala^{107}$) SLPI by simultaneous treatment with saliva and elastase

| Position of N-terminal amino acid | Band M |
|---|---|
| 1 | Arg |
| 2 | Arg |
| 3 | Lys |
| 4 | Pro |
| 5 | Gly |

Example 30

Treatment of ($Asn^{55}$-$Ala^{107}$) SLPI with Polymorphonuclear leucocyte elastase from human sputum According to the same procedure as described in Example 27, ($Asn^{55}$-$Ala^{107}$) SLPI (final concentration 100 $\mu$M) was treated with elastase (final concentration 200 $\mu$M) at 37° C. for 48 hours. The sample was separated by SDS-PAGE, and electrically transferred to a filter as described in Example 27, a band corresponding to a molecular weight of about 5,500 was cut out, and an N-terminal amino acid sequence was analyzed. A result is shown in Table 21.

As seen from this result, (Asn$^{55}$-Ala$^{107}$) SLPI amino acid sequence treated with elastase at 37° C. for 48 hours was converted to an amino acid of SLPI starting from Arg$^{58}$. Namely, (Asn$^{55}$-Ala$^{107}$) SLPI was cleaved at the site between Thr$^{57}$-Arg$^{58}$ with elastase from human sputum, and converted to (Arg$^{58}$-Ala$^{107}$) SLPI.

TABLE 21

N-terminal amino acid sequence of a partial decomposition product of (Asn$^{55}$-Ala$^{107}$) SLPI with elastase from human sputum

| Position of N-terminal amino acid | Identified amino acid |
|---|---|
| 1 | Arg |
| 2 | Arg |
| 3 | Lys |
| 4 | Pro |
| 5 | Gly |

From the results of Examples 27 to 30, it is clear that the (Arg$^{58}$-Ala$^{107}$) SLPI is a C-terminal polypeptide of native SLPI.

Example 31
Construction of expression plasmid for a fused protein comprising a human growth hormone fragment polypeptide and (Arg$^{58}$-Ala$^{107}$) SLPI polypeptide, and preparation of transformant thereof A polymerase chain reaction (PCR) (Saiki, R. K. et al., Science 239, 487–491, 1985) was carried out using as a template DNA an expression plasmid pGH-E59 comprising a gene for (Met$^{-1}$Phe$^{1}$-Phe$^{139}$) human growth hormone fragment polypeptide and a gene for an enterokinase cleavage sequence and as primers synthetic DNA fragments (1) and (2) (SEQ ID NO:24 and 25) (FIG. 24), and the amplified product was again subjected to PCR using synthetic DNA fragments (2) and (3) (SEQ ID NO:25 and 23) (FIG. 24), and the amplified product was cleaved with BglII (Takara Shuzo) to obtain a fragment of about 120 bp. Note, the PCR condition was as follows: after denaturation at 93° C. for 5 minutes, one cycle comprises 93° C., 1.5 minutes; 57° C., 2 minutes; 72° C., 2 minutes total 30 cycles, followed by 72° C. 7 minutes for termination of reaction.

On the other hand, pGH-E59 was cleaved with BglII (Takara Shuzo), and a BglII-BglII fragment of about 4.6 kbp was separated by agarose gel electrophoresis and recovered by a GENECLEAN II (BIO 101). This BglII-BglII fragment of about 4.6 kbp was dephosphorylated at its 5'-terminus with bacterial alkaline phosphatase (Takara Shuzo) according to a Takara Shuzo protocol.

The dephosphorylated BglII-BglII fragment of about 4.6 kbp was ligated with the PCR-amplified BglII-BglII fragment of about 120 bp using a ligation kit (Takara Shuzo), and the ligated DNA was introduced into E. coli HB101 competent cells (Takara Shuzo), which were then cultured in an LB agar medium containing ampicillin to obtain a transformant (HB/GH-T58) containing a desired fused protein expression plasmid.

Plasmid DNA was extracted from the transformant, and purified with a QIAGEN (from BIO 101) to obtain an expression plasmid pGH-T58 for a fused protein comprising a human growth hormone fragment peptide, a linker sequence comprising an thrombin cleavage site, and (Arg$^{58}$-Ala$^{107}$) SLPI polypeptide (FIG. 25). The nucleotide sequence of the plasmid DNA was directly confirmed by Hitachi fluorescent automatic DNA sequencer SQ 3000 using Dye Terminator kit (Hitachi).

Example 32
Expression of fused protein gene
E. coli HB101 containing a fused protein expression plasmid pGH-T58 obtained in Example 31 was cultured overnight in 500 ml of a modified M9 medium (1% (NH$_4$)$_2$HPO$_4$, 0.3% K$_2$SO$_4$, 0.3% NaCl) containing 0.25% glucose, 3 mg/ml yeast extract (Difco) and 20 mg/ml casamino acid (Difco) to which, after autoclave sterilization, MgSO$_4$ and CaCl$_2$ were aseptically added to a final concentration of 1 mM. The overnight culture was added to 10 liters of a medium having the same composition to adjust OD660 value to 0.2, and culturing was carried out in a jar fermenter at 37° C. When OD660 reached 20, 3-β-indoleacrylate was added to the culture medium to a final concentration of 150 μg/ml, culturing was further continued at 37° C. for 4 hours. After that E. coli cells were collected by centrifugation, and washed with 0.5M of Tris buffer (pH 8.0).

The washed cells were suspended in 0.5M Tris buffer containing lysozyme (1/200 of wet cell weight) and EDTA-3Na (1/20 of wet cell weight), sonicated with a ultrasonicator (Branson, CELL DISRUPTER 900) to disrupt the cells. The sonicated cells were centrifuged to obtain a precipitate containing the desired fused protein as inclusion bodies.

Note, E. coli HB101 containing the plasmid pGH-T58 was designated as a HB/GH-T58, and deposited with the fermentation Research Institute, Agency of Industrial Science and Technology (FRI), under the Budapest Treaty as FERM BP-3862 on May 20, 1992.

Example 33
Sulfonation of cysteine residues in fused protein and cleavage of sulfonated fused protein with thrombin 25 g of the fused protein obtained in Example 32 was suspended in 200 ml of 0.5M Tris buffer (pH 8.0), and to the suspension were added 240 g of urea to solubilize the fused protein and sodium sulfite (Wako Pure chemical) to a final concentration 0.7M, and the mixture was reacted at 45° C. for 20 minutes. In addition, sodium 4-thionate (Sigma) was added thereon to a final concentration 0.1M, and reaction was carried out 45° C. for 20 minutes. The reaction mixture was made to 1 liter by adding 10 mM Tris buffer (pH 8.0), and ultrafiltrated (Fuji filter: FILTRON) to make a volume of the mixture to 200 ml. This procedure was repeated 5 times. To the sulfonated fused protein solution thus obtained (the fraction which did not pass through the ultrafiltration membrane) was added 3000 U bovine thrombin (Mochida Seiyaku), and the mixture was reacted at 37° C. for 3 hours. Next, the reaction mixture was ultrafiltrated through a 300K filter, and (Arg$^{58}$-Ala$^{107}$) SLPI sulfonated derivative contained in the filtrate was purified by reverse HPLC (Protein C4, from Vydac), and lyophilized. The N-terminal amino acid sequence of the (Arg$^{58}$-Ala$^{107}$) SLPI sulphonated derivative thus obtained was determined using a protein sequencer (Applied Biosystems 477A).

Example 34
Refolding of (Arg$^{58}$-Ala$^{107}$) SLPI sulfonated derivative to active molecule (disulfide formation)

Figure 26:
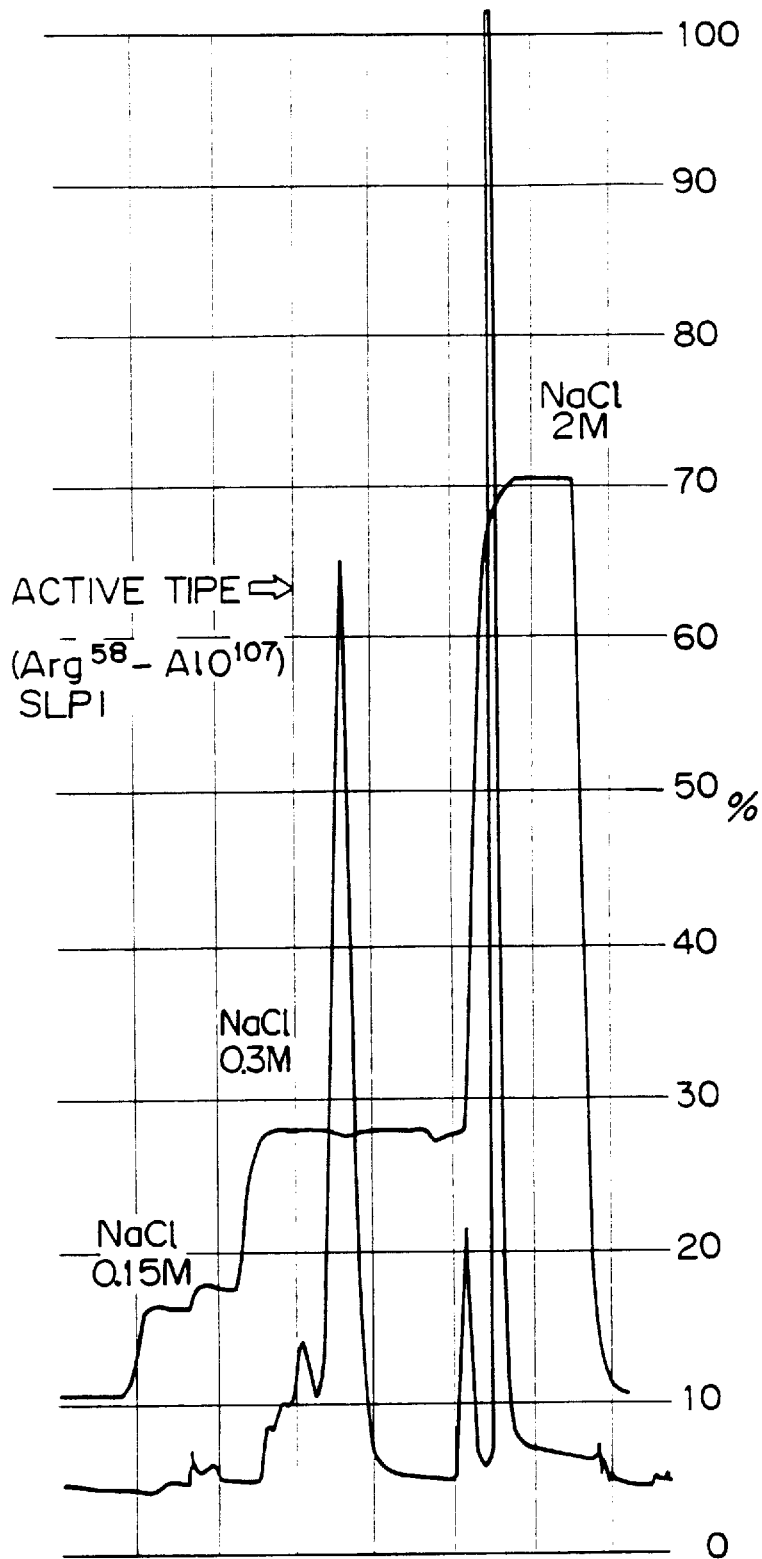
FIG. 26 represents an elution pattern of S-Sepharose ion exchange chromatography for an active type (Arg$^{58}$-Ala$^{107}$) SLPI in Example 34.

1 g of the (Arg$^{58}$-Ala$^{107}$) SLPI sulfonated derivative obtained in Example 33 was dissolved in 5 liters of a refolding buffer (0.05M Tris-HCl, pH 8.5, 0.3 mM oxidated glutathione, 1.5 mM reduced glutathione), and after reaction at 4° C. for 2 days, the reaction mixture was subjected to S-Sepharose (Pharmacia) ion exchange chromatography. An elution profile is shown in FIG. 26. A desired fraction eluted with 0.3M NaCl was purified by a reverse HPLC (Vydac, Protein C4), and lyophilized to obtain active (Arg$^{58}$-Ala$^{107}$) SLPI.

Example 35

Assay of serine protease inhibitory activity of ($Arg^{58}$-$Ala^{107}$) SLPI (1)

Assay method used was as follows.

(1) Reagent solution

Buffer: 0.1M (2-hydroxyethyl)piperazine-N'-2-ethansulfonic acid (HEPES), 0.5M NaCl, pH 7.5.

Enzyme concentration: the following enzyme was dissolved in the above-mentioned buffer to a concentration 9 times that shown in Table 22.

A. Polymorphonuclear leucocyte elastase from human sputum (EPC Co., Funakoshi Yakuhin)

B. Bovine spleen trypsin (Sigma)

C. Bovine spleen chymotrypsin (Sigma)

D. Porcine spleen elastase (Sigma)

E. Human cathepsin G (EPC Co., Funakoshi Yakuhin)

Substrate solution: for the enzymes A, B, C, D and E, the following substrate a, b, c, d or e, respectively, was dissolved in a solution of DMSO +the above-mentioned buffer (1:9) (note, final concentration of DMSO was 10% in the buffer) to a concentration of 9 times that shown in Table 22.

a. MeO-Suc-Ala-Ala-Pro-Val-pNA (Bachem)
b. Bz-Arg-pNA (Bachem)
c. Suc-Ala-Ala-Pro-Phe-pNA (Bachem)
d. Suc-Ala-Ala-Ala-pNA (Nakarai Kagaku)
e. Suc-Phe-Pro-Phe-pNA (Bachem)

TABLE 22

Final concentrations of enzymes and substrates in enzyme inhibitory assay

| | Enzyme concentration (M) | Substrate concentration (M) |
|---|---|---|
| Assay for elastase inhibitory activity | A. $2 \times 10^{-8}$ | a. $3.0 \times 10^{-4}$ |
| Assay for trypsin inhibitory activity | B. $2 \times 10^{-7}$ | b. $1.0 \times 10^{-3}$ |
| Assay for chymotrypsin inhibitory activity | C. $1 \times 10^{-8}$ | c. $1.0 \times 10^{-3}$ |
| Assay for porcine elastase inhibitory activity | D. $1 \times 10^{-6}$ | d. $1.0 \times 10^{-3}$ |
| Assay for cathepsin G inhibitory activity | E. $2 \times 10^{-8}$ | e. $1.0 \times 10^{-3}$ |

(2) Method

To wells of an ELISA 96-well microtiter plate, were added 120 μl of the buffer and the 20 μl of a sample solution of ($Arg^{58}$-$Ala^{107}$) SLPI obtained in Example 34, followed by 20 μl of the enzyme solution. The mixture was reacted at 37° C. for 10 minutes. Next, 20 μl of the substrate was added, and developed at 37° C. The developed color was measured by absorption at 405 nm.

As a control the same procedure was carried out using SLPI.

An inhibitory activity was expressed by a concentration of an inhibitor to be tested that provides 50% inhibition ($IC_{50}$ value). The result is shown in Table 23.

TABLE 23

Serine protease inhibitory activity of the present polypeptide

| | $IC_{50}$ (M) | |
|---|---|---|
| | ($Arg^{58}$-$Ala^{107}$) SLPI | SLPI |
| Human elastase | $1.2 \times 10^{-8}$ | $1.3 \times 10^{-8}$ |
| Trypsin | $2.0 \times 10^{-6}$ | $3.3 \times 10^{-7}$ |
| Chymotrypsin | $6.8 \times 10^{-9}$ | $7.0 \times 10^{-9}$ |
| Porcine elastase | $2.3 \times 10^{-5}$ | $1.3 \times 10^{-5}$ |
| Cathepsin G | $8.0 \times 10^{-9}$ | $5.5 \times 10^{-9}$ |

Example 36

Assay of serine protease inhibitory activity of ($Arg^{58}$-$Ala^{107}$) SLPI (2)

Protein concentration providing a 50% inhibitory activity (IC50) for ($Arg^{55}$-$Ala^{107}$) SLPI and control SLPI on the following 4 enzymes was determined.

F. Human plasma thrombin (Sigma)
G. Human plasma plasmin (sigma)
H. Human plasma kallikrein (Protogene, Funakoshi Yakuhin)
I. Porcine FXa (Daichi Seiyaku)

Method for assay was follows.

(1) Reagent solution

Buffer: Buffer solution for each enzyme is as follows.

Thrombin and FXa: 50 mM Tris-HCl, 7.5 mM EDTA-2Na, 175 mM NaCl (pH 8.4)

Plasmin: 50 mM Tris-HCl, 100 mM NaCl (pH 7.4)

Kallikrein: 50 mM Tris-HCl, 361 mM NaCl, 0.01 mg/ml Polybrene (pH 7.8)

Enzyme concentration: concentration of each enzyme is shown in Table 24.

TABLE 24

| | Enzyme concentration (M) | Substrate concentration (M) |
|---|---|---|
| Assay for thrombin inhibitory activity | $3 \times 10^{-9}$ | $1.9 \times 10^{-4}$ |
| Assay for plasmin inhibitory activity | $1.0 \times 10^{-7}$ | $8.2 \times 10^{-4}$ |
| Assay for kallikrein inhibitory activity | $1.0 \times 10^{-7}$ | $2.0 \times 10^{-3}$ |
| Assay for Fxa inhibitory activity | $1.0 \times 10^{-8}$ | $4.0 \times 10^{-4}$ |

Substrate solution: for the enzymes F, G, H and I, the following substrate f, g, h or i, respectively, was dissolved to a final concentration shown in Table 24.

f. H.D-Phe-Pip-Arg-pNA (Kabi Vitrum)
g. H.D-Val-Leu-Lys-pNA (Kabi Vitrum)
h. H.D-Pro-Phe-Arg-pNA (Kabi Vitram)
i. Ratio 1:1 mixture of the following compounds:

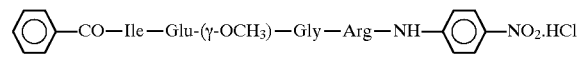

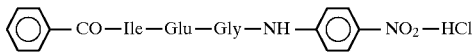

(2) Method

To wells of an ELISA 96-well microtiter plate, were added a solution of ($Arg^{58}$-$Ala^{107}$) SLPI obtained in Example 34 and then the enzyme solution, and the mixture was incubated at 37° C. for 10 minutes. Next, the substrate solution was added to develop the color, whose absorption was then measured at 405 nm. As a control, SLPI was used.

(3) Result

Both (Arg$^{58}$-Ala$^{107}$) SLPI and SLPI did not exhibit inhibitory activity to all of 4 enzymes at a final concentration up to ×10$^{-5}$M.

Example 37

Inhibitory constant (Ki) of (Arg$^{58}$-Ala$^{107}$)

Method for assay is as follow.

(1) Reagent solution

Buffer: 0.1M N-(2-hydroxyethyl)piperazine-N'-2-ethanesulfonic acid (HEPES), 1.0M NaCl, 0.1% polyethylene glycol (pH 7.5)

Enzyme solution: the following enzyme was dissolved in the above-mentioned buffer to a concentration 9 times that shown in Table 25.

A. Polymorphonuclear leucocyte elastase from human sputum (EPC Co., Funakoshi Yakuhin)

B. Bovine spleen trypsin (Sigma)

Substrate solution: for the enzymes A and B, the following substrate a or b was dissolved in a solution of DMSO+ the above-mentioned buffer (1:9), or in DMSO, respectively.

a. MeO-Suc-Ala-Ala-Pro-Val-pNA (Bachem)
b. Bz-Arg-pNA (Bachem)

TABLE 25

Final concentration of enxyme and substrate in an assay of inhibitory constant

| | Enzyme concentration (M) | Substrate concentration (M) |
|---|---|---|
| Elastase | 2.0 × 10$^{-8}$ | 3.0 × 10$^{-4}$ |
| Trypsin | 2.0 × 10$^{-7}$ | 1.1 × 10$^{-3}$ |

(2) Method

To wells of an ELISA 96-well microtiter plate, were added 120 μl of the buffer, 20 μl of a sample solution of (Arg$^{55}$-Ala$^{107}$) SLPI obtained in Example 25, and 20 μl of the enzyme solution in this order, an the mixture was reacted at 37° C. for 1 hour. Next, 20 μl of the substrate was added to develop at 25° C. Absorption of the developed color was measured at 405 nm. As a control, SLPI was used.

On the basis of the result thus obtained, an inhibitory constant (Ki) of (Arg$^{58}$-Ala$^{107}$) SLPI of the present invention was calculated according to the method of Henderson (Henderson, P. J. F. (1972), Biochem. J. 127, 321–333). The result is shown in Table 26.

TABLE 26

| Inhibitory constant (Ki) to serine protease | | |
|---|---|---|
| | Inhibitory constant (Ki) (M) | |
| | (Arg$^{58}$–Ala$^{107}$) SLPI | SLPI |
| Elastase Ki (E) | 0.9 × 10$^{-10}$ | 0.8 × 10$^{-10}$ |
| Trypsin Ki (T) | 1.1 × 10$^{-6}$ | 3.3 × 10$^{-8}$ |

As seen from Table 26, a relative ratio of an inhibitory activity of the present (Arg$^{58}$-Ala$^{107}$) SLPI on trypsin to that on elastase (Ki(T)/Ki(E)) is about 12,000, which means that (Arg$^{58}$-Ala$^{107}$) SLPI substantially does not exhibit inhibitory activity to trypsin. Since the present elastase inhibitory polypeptide exhibits a high elastase inhibitory activity, but a low inhibitory activity to other serine proteases, in particular trypsin-like serine protease, it is promising as a useful therapeutic agent for the suppression of the progress of emphysema.

Further, the present fused protein expression system using a human growth hormone or a portion thereof is highly efficient and can be universally used to produce a relatively low molecular peptide by gene recombination.

We claim:

1. An isolated and purified elastase inhibitory polypeptide consisting of an amino acid sequence represented by SEQ ID NO:2, wherein the polypeptide has a trypsin-inhibitory activity, the polypeptide trypsin-inhibitory activity being less than trypsin-inhibitory activity exhibited by SLPI.

2. A pharmaceutical composition comprising a polypeptide according to claim 1, and a pharmaceutically acceptable carrier.

3. A pharmaceutical composition according to claim 2 for treatment of diseases caused by an excess activation of neutrophil.

4. A pharmaceutical composition according to claim 2, wherein said diseases are those caused by neutrophil-released protease.

5. A pharmaceutical composition according to claim 4, wherein said diseases are inflammatory diseases, platelet coagulation thrombosis or ischemia reperfusion injury.

6. An isolated and purified elastase inhibitory polypeptide consisting of an amino acid sequence represented by SEQ ID NO:1, wherein the polypeptide has a trypsin-inhibitory activity, the polypeptide trypsin-inhibitory activity being less than trypsin-inhibitory activity exhibited by SLPI.

7. A pharmaceutical composition comprising a polypeptide according to claim 6, and a pharmaceutically acceptable carrier.

8. A pharmaceutical composition according to claim 7 for treatment of diseases caused by an excess activation of neutrophil.

9. A pharmaceutical composition according to claim 7, wherein said diseases are those caused by neutrophil-released protease.

10. A pharmaceutical composition according to claim 9, wherein said diseases are inflammatory diseases, platelet coagulation thrombosis or ischemia reperfusion injury.

11. An isolated and purified elastase inhibitory polypeptide consisting of an amino acid sequence represented by SEQ ID NO:3, wherein the polypeptide has a trypsin-inhibitory activity, the polypeptide trypsin-inhibitory activity being less than trypsin-inhibitory activity exhibited by SLPI.

12. A pharmaceutical composition comprising a polypeptide according to claim 11, and a pharmaceutically acceptable carrier.

13. A pharmaceutical composition according to claim 12 for treatment of diseases caused by an excess activation of neutrophil.

14. A pharmaceutical composition according to claim 12, wherein said diseases are those caused by neutrophil-released protease.

15. A pharmaceutical composition according to claim 14, wherein said diseases are inflammatory diseases, platelet coagulation thrombosis or ischemia reperfusion injury.

* * * * *

SEQUENCE LISTING ( 1 ) GENERAL INFORMATION:

( i i i ) NUMBER OF SEQUENCES: 36

( 2 ) INFORMATION FOR SEQ ID NO:1:

( i ) SEQUENCE CHARACTERISTICS:
        ( A ) LENGTH: 53 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Asn  Pro  Thr  Arg  Arg  Lys  Pro  Gly  Lys  Cys  Pro  Val  Thr  Tyr  Gly  Gln
 1                    5                        10                            15

Cys  Leu  Met  Leu  Asn  Pro  Pro  Asn  Phe  Cys  Glu  Met  Asp  Gly  Gln  Cys
                20                        25                        30

Lys  Arg  Asp  Leu  Lys  Cys  Cys  Met  Gly  Met  Cys  Gly  Lys  Ser  Cys  Val
           35                        40                        45

Ser  Pro  Val  Lys  Ala
```

50

(2) INFORMATION FOR SEQ ID NO:2:

(i) SEQUENCE CHARACTERISTICS:
        (A) LENGTH: 50 amino acids
        (B) TYPE: amino acid
        (D) TOPOLOGY: linear (ii) MOLECULE TYPE: peptide (xi) SEQUENCE DESCRIPTION: SEQ ID NO:2:

```
Arg Arg Lys Pro Gly Lys Cys Pro Val Thr Tyr Gly Gln Cys Leu Met
 1               5                   10                  15

Leu Asn Pro Pro Asn Phe Cys Glu Met Asp Gly Gln Cys Lys Arg Asp
             20                  25                  30

Leu Lys Cys Cys Met Gly Met Cys Gly Lys Ser Cys Val Ser Pro Val
         35                  40                  45

Lys Ala
    50
```

(2) INFORMATION FOR SEQ ID NO:3:

(i) SEQUENCE CHARACTERISTICS:
        (A) LENGTH: 49 amino acids
        (B) TYPE: amino acid
        (D) TOPOLOGY: linear (ii) MOLECULE TYPE: peptide (xi) SEQUENCE DESCRIPTION: SEQ ID NO:3:

```
Arg Lys Pro Gly Lys Cys Pro Val Thr Tyr Gly Gln Cys Leu Met Leu
 1               5                   10                  15

Asn Pro Pro Asn Phe Cys Glu Met Asp Gly Gln Cys Lys Arg Asp Leu
             20                  25                  30

Lys Cys Cys Met Gly Met Cys Gly Lys Ser Cys Val Ser Pro Val Lys
         35                  40                  45

Ala
```

(2) INFORMATION FOR SEQ ID NO:4:

(i) SEQUENCE CHARACTERISTICS:
        (A) LENGTH: 107 amino acids
        (B) TYPE: amino acid
        (D) TOPOLOGY: linear (ii) MOLECULE TYPE: peptide (xi) SEQUENCE DESCRIPTION: SEQ ID NO:4:

```
Ser Gly Lys Ser Phe Lys Ala Gly Val Cys Pro Pro Lys Lys Ser Ala
 1               5                   10                  15

Gln Cys Leu Arg Tyr Lys Lys Pro Glu Cys Gln Ser Asp Trp Gln Cys
             20                  25                  30

Pro Gly Lys Lys Arg Cys Cys Pro Asp Thr Cys Gly Ile Lys Cys Leu
         35                  40                  45

Asp Pro Val Asp Thr Pro Asn Pro Thr Arg Arg Lys Pro Gly Lys Cys
     50                  55                  60

Pro Val Thr Tyr Gly Gln Cys Leu Met Leu Asn Pro Pro Asn Phe Cys
65                   70                  75                  80

Glu Met Asp Gly Gln Cys Lys Arg Asp Leu Lys Cys Cys Met Gly Met
             85                  90                  95

Cys Gly Lys Ser Cys Val Ser Pro Val Lys Ala
```

( 2 ) INFORMATION FOR SEQ ID NO:5:

( i ) SEQUENCE CHARACTERISTICS:
      ( A ) LENGTH: 194 base pairs
      ( B ) TYPE: nucleic acid
      ( C ) STRANDEDNESS: double
      ( D ) TOPOLOGY: linear ( i i ) MOLECULE TYPE: DNA (synthetic)

( x i ) SEQUENCE DESCRIPTION: SEQ ID NO:5:

```
GATCCGGTCG ACACCCCGAA CCCGACGCGT CGTAAACCGG GTAAATGTCC GGTTACATAT      60
GGTCAGTGTC TGATGCTGAA CCCGCCGAAC TTCTGTGAAA TGGACGGTCA GTGTAAACGA     120
GATCTGAAAT GTTGTATGGG TATGTGTGGT AAATCTTGTG TTTCTCCGGT TAAAGCATAA     180
TAGCTCGAGC TGCA                                                      194
```

( 2 ) INFORMATION FOR SEQ ID NO:6:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:6:

```
Val  Asp  Asp  Asp  Asp  Lys
 1                  5
```

( 2 ) INFORMATION FOR SEQ ID NO:7:

( i ) SEQUENCE CHARACTERISTICS:
      ( A ) LENGTH: 8 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:7:

```
Arg  Ala  Leu  Leu  Ala  Gly  Pro  Arg
 1                  5
```

( 2 ) INFORMATION FOR SEQ ID NO:8:

( i ) SEQUENCE CHARACTERISTICS:
      ( A ) LENGTH: 4 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:8:

```
Leu  Val  Pro  Arg
 1
```

( 2 ) INFORMATION FOR SEQ ID NO:9:

( i ) SEQUENCE CHARACTERISTICS:
      ( A ) LENGTH: 30 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:9:

```
Ala  Asp  Ser  Gly  Glu  Gly  Asp  Phe  Leu  Ala  Glu  Gly  Gly  Gly  Val  Arg
 1              5                        10                            15

Glu  Gly  Val  Asn  Asp  Asn  Glu  Glu  Gly  Phe  Phe  Ser  Ala  Arg
               20                       25                      30
```

(2) INFORMATION FOR SEQ ID NO:10:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:10:

```
Asp  Asp  Pro  Pro  Thr  Val  Glu  Leu  Gln  Gly  Leu  Val  Pro  Arg
 1              5                        10
```

(2) INFORMATION FOR SEQ ID NO:11:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:11:

```
Asp  Asp  Asp  Asp  Lys
 1                    5
```

(2) INFORMATION FOR SEQ ID NO:12:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:12:

GATCTTCCTG GTTCCGCGTA ACCCGA                    26

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:13:

GATCTTCAAC GGTAACCCGA                      20

(2) INFORMATION FOR SEQ ID NO:14:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:14:

```
Gln  Ile  Phe  Leu  Val  Pro  Arg  Asn  Pro  Thr
 1              5                        10
```

( 2 ) INFORMATION FOR SEQ ID NO:15:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:15:

```
Gln  Ile  Phe  Asn  Gly  Asn  Pro  Thr  Arg
 1                    5
```

( 2 ) INFORMATION FOR SEQ ID NO:16:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:16:

```
GATCTTCCTG GTTC                                                              14
```

( 2 ) INFORMATION FOR SEQ ID NO:17:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:17:

```
Gln  Ile  Phe  Leu  Val  Pro  Arg
 1                    5
```

( 2 ) INFORMATION FOR SEQ ID NO:18:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:18:

```
GGTCAGATCT TCGGTGACGA CGATGACAAA CGTAAA                                      36
```

( 2 ) INFORMATION FOR SEQ ID NO:19:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:19:

```
GACGACGATG ACAAACGTAA ACCGGGTAAA TGTCCG                                      36
```

( 2 ) INFORMATION FOR SEQ ID NO:20:

( i ) SEQUENCE CHARACTERISTICS:

(A) LENGTH: 21 base pairs
                    (B) TYPE: nucleic acid
                    (C) STRANDEDNESS: single
                    (D) TOPOLOGY: linear (ii) MOLECULE TYPE: DNA (synthetic)

(xi) SEQUENCE DESCRIPTION: SEQ ID NO:20:

TTTCAGATCT CGTTTACACT G                                                                           21

(2) INFORMATION FOR SEQ ID NO:21:

(i) SEQUENCE CHARACTERISTICS:
                    (A) LENGTH: 17 amino acids
                    (B) TYPE: amino acid
                    (D) TOPOLOGY: linear (ii) MOLECULE TYPE: peptide (xi) SEQUENCE DESCRIPTION: SEQ ID NO:21:

Gly Gln Ile Phe Gly Asp Asp Asp Lys Arg Lys Pro Gly Lys Cys
      1               5                  10                  15
     Pro (2) INFORMATION FOR SEQ ID NO:22:

(i) SEQUENCE CHARACTERISTICS:
                    (A) LENGTH: 7 amino acids
                    (B) TYPE: amino acid
                    (D) TOPOLOGY: linear (ii) MOLECULE TYPE: peptide (xi) SEQUENCE DESCRIPTION: SEQ ID NO:22:

Gln Cys Lys Arg Asp Leu Lys
      1               5

(2) INFORMATION FOR SEQ ID NO:23:

(i) SEQUENCE CHARACTERISTICS:
                    (A) LENGTH: 32 base pairs
                    (B) TYPE: nucleic acid
                    (C) STRANDEDNESS: single
                    (D) TOPOLOGY: linear (ii) MOLECULE TYPE: DNA (synthetic)

(xi) SEQUENCE DESCRIPTION: SEQ ID NO:23:

GTCAGATCTT CCTGGTTCCG CGTCGTCGTA AA                                                               32

(2) INFORMATION FOR SEQ ID NO:24:

(i) SEQUENCE CHARACTERISTICS:
                    (A) LENGTH: 30 base pairs
                    (B) TYPE: nucleic acid
                    (C) STRANDEDNESS: single
                    (D) TOPOLOGY: linear (ii) MOLECULE TYPE: DNA (synthetic)

(xi) SEQUENCE DESCRIPTION: SEQ ID NO:24:

GGTTCCGCGT CGTCGTAAAC CGGGTAAATG                                                                  30

(2) INFORMATION FOR SEQ ID NO:25:

(i) SEQUENCE CHARACTERISTICS:
                    (A) LENGTH: 21 base pairs
                    (B) TYPE: nucleic acid
                    (C) STRANDEDNESS: single (D) TOPOLOGY: linear (i i) MOLECULE TYPE: DNA (synthetic)

(x i) SEQUENCE DESCRIPTION: SEQ ID NO:25:

TTTCAGATCT CGTTTACACT G    21

(2) INFORMATION FOR SEQ ID NO:26:

(i) SEQUENCE CHARACTERISTICS:
        (A) LENGTH: 14 amino acids
        (B) TYPE: amino acid
        (D) TOPOLOGY: linear (i i) MOLECULE TYPE: peptide (x i) SEQUENCE DESCRIPTION: SEQ ID NO:26:

Gln Ile Phe Leu Val Pro Arg Arg Arg Lys Pro Gly Lys Cys
1               5                   10

(2) INFORMATION FOR SEQ ID NO:27:

(i) SEQUENCE CHARACTERISTICS:
        (A) LENGTH: 7 amino acids
        (B) TYPE: amino acid
        (D) TOPOLOGY: linear (i i) MOLECULE TYPE: peptide (x i) SEQUENCE DESCRIPTION: SEQ ID NO:27:

Gln Cys Lys Arg Asp Leu Lys
1               5

(2) INFORMATION FOR SEQ ID NO:28:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (i i) MOLECULE TYPE: DNA (synthetic)

(x i) SEQUENCE DESCRIPTION: SEQ ID NO:28:

CGCGTCGGGT TACGCGGAAC CAGGAA    26

(2) INFORMATION FOR SEQ ID NO:29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (synthetic)

(x i) SEQUENCE DESCRIPTION: SEQ ID NO:29:

CGCGTCGGGT TACCGTTGAA    20

(2) INFORMATION FOR SEQ ID NO:30:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (i i) MOLECULE TYPE: DNA (synthetic)

(x i) SEQUENCE DESCRIPTION: SEQ ID NO:30:

```
CGCGGAACCA GGAA                                                                                       14

( 2 ) INFORMATION FOR SEQ ID NO:31:

( i ) SEQUENCE CHARACTERISTICS:
                  ( A ) LENGTH: 63 base pairs
                  ( B ) TYPE: nucleic acid
                  ( C ) STRANDEDNESS: single stranded
                  ( D ) TOPOLOGY: linear ( i i ) MOLECULE TYPE: DNA (synthetic)

( x i ) SEQUENCE DESCRIPTION: SEQ ID NO:31:

GATCCGGTCG ACACCCCGAA CCCGACGCGT CGTAAACCGG GTAAATGTCC GGTTACATAT           60

GGT                                                                        63

( 2 ) INFORMATION FOR SEQ ID NO:32:

( i ) SEQUENCE CHARACTERISTICS:
                  ( A ) LENGTH: 66 base pairs
                  ( B ) TYPE: nucleic acid
                  ( C ) STRANDEDNESS: single stranded
                  ( D ) TOPOLOGY: linear ( i i ) MOLECULE TYPE: DNA (synthetic)

( x i ) SEQUENCE DESCRIPTION: SEQ ID NO:32:

GACACTGACC ATATGTAACC GGACATTTAC CCGGTTTACG ACGCGTCGGG TTCGGGGTGT           60

CGACCG                                                                     66

( 2 ) INFORMATION FOR SEQ ID NO:33:

( i ) SEQUENCE CHARACTERISTICS:
                  ( A ) LENGTH: 67 base pairs
                  ( B ) TYPE: nucleic acid
                  ( C ) STRANDEDNESS: single stranded
                  ( D ) TOPOLOGY: linear ( i i ) MOLECULE TYPE: DNA (synthetic)

( x i ) SEQUENCE DESCRIPTION: SEQ ID NO:33:

CAGTGTCTGA TGCTGAACCC GCCGAACTTC TGTGAAATGG ACGGTCAGTG TAAACGAGAT           60

CTGAAAT                                                                    67

( 2 ) INFORMATION FOR SEQ ID NO:34:

( i ) SEQUENCE CHARACTERISTICS:
                  ( A ) LENGTH: 68 base pairs
                  ( B ) TYPE: nucleic acid
                  ( C ) STRANDEDNESS: single stranded
                  ( D ) TOPOLOGY: linear ( i i ) MOLECULE TYPE: DNA (synthetic)

( x i ) SEQUENCE DESCRIPTION: SEQ ID NO:34:

CATACAACAT TTCAGATCTC GTTTACACTG ACCGTCCATT TCACAGAAGT TCGGCGGGTT           60

CAGCATCA                                                                   68

( 2 ) INFORMATION FOR SEQ ID NO:35:

( i ) SEQUENCE CHARACTERISTICS:
                  ( A ) LENGTH: 64 base pairs
                  ( B ) TYPE: nucleic acid
                  ( C ) STRANDEDNESS: single stranded
                  ( D ) TOPOLOGY: linear
```

-continued (i i) MOLECULE TYPE: DNA (synthetic)

(x i) SEQUENCE DESCRIPTION: SEQ ID NO:35:

GTTGTATGGG TATGTGTGGT AAATCTTGTG TTTCTCCGGT TAAAGCATAA TAGCTCGAGC    60

TGCA    64

(2) INFORMATION FOR SEQ ID NO:36:

(i) SEQUENCE CHARACTERISTICS:
(A) LENGTH: 52 base pairs
(B) TYPE: nucleic acid
(C) STRANDEDNESS: single stranded
(D) TOPOLOGY: linear (i i) MOLECULE TYPE: DNA (synthetic)

(x i) SEQUENCE DESCRIPTION: SEQ ID NO:36:

GCTCGAGCTA TTATGCTTTA ACCGGAGAAA CACAAGATTT ACCACACATA CC    52